(12) United States Patent
Langenfeld et al.

(10) Patent No.: US 10,345,208 B2
(45) Date of Patent: Jul. 9, 2019

(54) SYSTEM AND METHOD FOR APPLYING FORCE TO A DEVICE

(71) Applicant: DEKA Products Limited Partnership, Manchester, NH (US)

(72) Inventors: Christopher C. Langenfeld, Nashua, NH (US); Dirk A. van der Merwe, Canterbury, NH (US); Grant A. Peret, Bedford, NH (US); John C. Anastasiou, New Boston, NH (US); Jonathan Parker, Henniker, NH (US); Michael A. Baker, Manchester, NH (US)

(73) Assignee: DEKA Products Limited Partnership, Manchester, NH (US)

( * ) Notice: Subject to any disclaimer, the term of this patent is extended or adjusted under 35 U.S.C. 154(b) by 0 days.

(21) Appl. No.: 15/648,378

(22) Filed: Jul. 12, 2017

(65) Prior Publication Data

US 2018/0017474 A1     Jan. 18, 2018

Related U.S. Application Data

(60) Provisional application No. 62/361,204, filed on Jul. 12, 2016, provisional application No. 62/361,209, filed on Jul. 12, 2016.

(51) Int. Cl.
| | |
|---|---|
| *G01N 3/00* | (2006.01) |
| *G01N 3/08* | (2006.01) |
| *G01N 3/20* | (2006.01) |
| *G01N 3/42* | (2006.01) |

(52) U.S. Cl.
CPC ............. *G01N 3/08* (2013.01); *G01N 3/20* (2013.01); *G01N 3/42* (2013.01)

(58) Field of Classification Search
CPC ............. G01N 3/08; G01N 3/20; G01N 3/42
USPC .......................................................... 73/818
See application file for complete search history.

(56) References Cited

U.S. PATENT DOCUMENTS

| | | | | |
|---|---|---|---|---|
| 5,059,365 | A | * | 10/1991 | Hertzer .............. B29C 45/1751 264/40.5 |
| 5,156,053 | A | | 10/1992 | Shiraishi et al. |
| 6,053,052 | A | | 4/2000 | Starostovic |
| 6,512,387 | B1 | * | 1/2003 | Bohn ................... G01R 31/046 324/762.02 |
| 2005/0079620 | A1 | | 4/2005 | Eberhard et al. |

(Continued)

OTHER PUBLICATIONS

Notification of Transmittal of the International Search Report and the Written Opinion of the International Searching Authority, International application # PCT/US2017/041776, dated Oct. 26, 2017.

(Continued)

*Primary Examiner* — Max H Noori
(74) *Attorney, Agent, or Firm* — Kathleen Chapman

(57) ABSTRACT

A system and method for applying force to at least one device by setting a target position of a pin with respect to the device, setting a target force that the pin will apply to the device, moving the pin towards the device, stopping the movement of the pin when the first of a force exerted on the device by the pin substantially equals the target force, or a position of the pin substantially equals the target position happens, and modifying the position of the pin to maintain the force of the pin on the device at substantially constant.

20 Claims, 45 Drawing Sheets

(56) References Cited

U.S. PATENT DOCUMENTS

| | | |
|---|---|---|
| 2008/0281533 A1 | 11/2008 | Galliot et al. |
| 2012/0022441 A1 | 1/2012 | Kelly et al. |
| 2012/0136477 A1* | 5/2012 | Merrow ............... G11B 17/225 |
| | | 700/218 |
| 2013/0238257 A1 | 9/2013 | Rajamani et al. |
| 2017/0370799 A1* | 12/2017 | Jones ................. B81C 99/0035 |

OTHER PUBLICATIONS

Leak Testing Case Studies: Small Medical Device Leak Test Machine, http://tqc.co.uk/leak-testing/leak-testing-small-medical-device-leak-test-machine.php, Jun. 29, 2017.

PCT/US2017/041776, Notification Concerning Transmittal of International Preliminary Report of Patentability (Chapter I of the Patent Cooperation Treaty), dated Jan. 24, 2019.

* cited by examiner

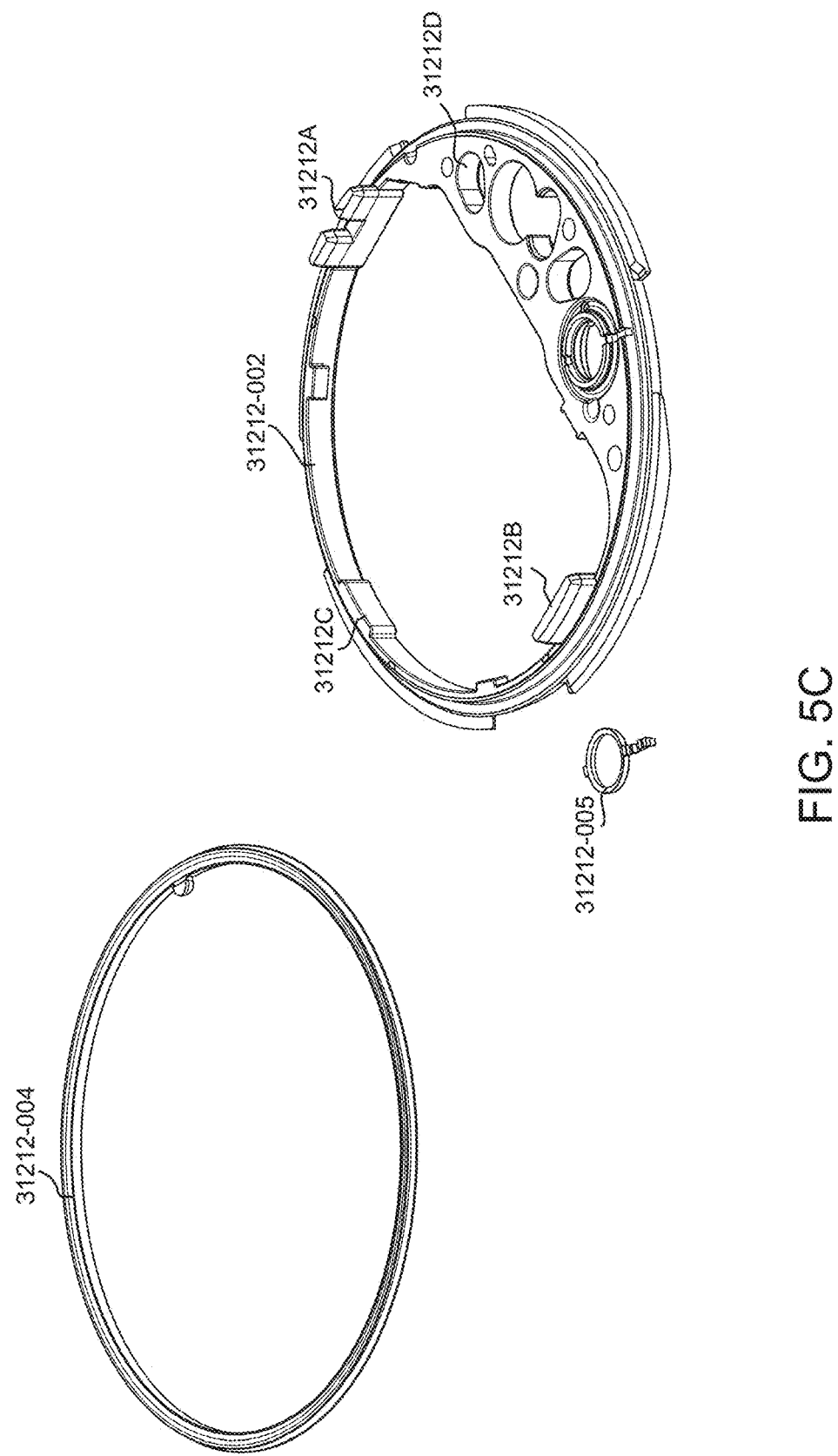

SYSTEM AND METHOD FOR APPLYING FORCE TO A DEVICE

CROSS REFERENCE TO RELATED APPLICATIONS

This utility patent application claims the benefit of U.S. Provisional Patent Application Ser. No. 62/361,204 filed Jul. 12, 2016, entitled System and Method for Applying Force to a Device, and U.S. Provisional Patent Application Ser. No. 62/361,209 filed Jul. 12, 2016, entitled System and Method for Controlling Motion, which are incorporated herein by reference in their entirety.

BACKGROUND

The present teachings relate generally to applying force to a device, and more specifically to actuating systems and methods that can apply force to devices to, for example, test devices.

Quality, performance, and reliability of devices can be exercised through the use of conformance and performance tests. Typical conformance and performance tests can include cycle testing using air, water, and steam, cycle testing against vacuum and positive pressure at various densities, varying pressure conditions, and cycle testing at ambient, cold, and elevated temperatures. Such tests can lack the precision that can be required for extremely find-scale force applications and their monitoring.

What are needed are systems and methods that can apply force precisely to a large range of devices, and monitor the reaction of the devices to the applied force. What are further needed are systems and methods that can coordinate force application across parts of a device, and/or across multiple devices. What are still further needed are systems and methods that can apply a range of forces simultaneously to multiple devices and/or multiple parts of a single or multiple devices, and/or sequentially to multiple devices and/or multiple parts of a single device or multiple devices.

SUMMARY

A method of the present teachings for applying a constant force to a device can include, but is not limited to including, setting a target position of a pin with respect to the device, setting a target force that the pin will apply to the device, moving the pin towards the device, stopping the movement of the pin when the first of a force exerted on the device by the pin substantially equals the target force, or a position of the pin substantially equals the target position happens, and modifying the position of the pin to maintain the force of the pin on the device at substantially constant.

A method of the present teachings for applying pressure to a device can include, but is not limited to including, pressurizing the device, setting a target position of a pin with respect to the device, setting a target force that the pin will apply to the device, moving the pin towards the device, stopping the movement of the pin when the first of a force exerted on the device by the pin substantially equals the target force, or a position of the pin substantially equals the target position happens, holding the position of the pin substantially constant, and monitoring the force over time.

A method for testing a device can include, but is not limited to including, setting a target first characteristic of a pressure actuator, the pressure actuator having an actual first characteristic, setting a target second characteristic of the pressure actuator, the pressure actuator having an actual second characteristic, adjusting the pressure actuator, the adjusting enabling the actual first characteristic to approach the target first characteristic, and the actual second characteristic to approach the target second characteristic, stopping the adjusting when the first of the actual first characteristic substantially equals the target first characteristic, or the actual second characteristic substantially equals the target second characteristic happens, adjusting the actual first characteristic to maintain the target second characteristic substantially constant, and testing the device by monitoring the actual first characteristic over time.

A system of the present teachings for applying force to a device can include, but is not limited to including, at least one platform, at least one device cage operably coupled with at least one platform, at least one device cover operably coupled with the at least one device cage, the device cage housing the device, at least one pressure actuator assembly substantially aligned with the device cage and operably coupled with the at least one platform, and at least one motion controller operably coupled with the at least one pressure actuator assembly, the at least one motion controller setting a target first characteristic of the at least one pressure actuator assembly, the pressure actuator assembly having an actual first characteristic, the at least one controller setting a target second characteristic of the at least one pressure actuator assembly, the at least one pressure actuator assembly having an actual second characteristic, the at least one motion controller adjusting the at least one pressure actuator assembly, the adjusting enabling the actual first characteristic to approach the target first characteristic, and the actual second characteristic to approach the target second characteristic and stopping the adjusting when the first of the actual first characteristic substantially equals the target first characteristic, or the actual second characteristic substantially equals the target second characteristic happens, the at least one motion controller adjusting the actual first characteristic to maintain the target second characteristic substantially constant.

The method of the present teachings for automatically adjusting actual characteristics to meet target characteristics can include, but is not limited to including, receiving a at least one target characteristic selection, arranging the at least one target characteristic into at least one first message, and transmitting the at least one first message to a motion controller. The method can also include generating, by the motion controller, at least one second message, the at least one second message including information required to adjust the at least one target characteristic, transmitting, by the motion controller, the at least one second message to at least one actuator node, and adjusting, by the at least one actuator node, at least one actual characteristic to meet the at least one target characteristic, if necessary. The method can optionally include checking, by the actuator node, the integrity of the at least one second message, and generating, by the actuator node, at least one third message including a status of the at least one second message.

The method of the present teachings for testing a device can include, but is not limited to including, setting a target position of a pin with respect to the device, and setting a target force being applied by the pin to the device. The pin can have an actual position and actual force. The method can include moving the pin towards the target position, stopping the movement of the pin when either the actual force exerted on the device by the pin substantially equals the target force, or the actual position of the pin substantially equals the target position. The method can include testing the device by comparing either the actual force or the actual position with at least one benchmark value to determine if the device meets pre-selected criteria at the target position or under the target force.

The method can optionally include monitoring the actual position over time, monitoring the actual force over time, modifying the position of the pin to maintain the force of the pin on the device at substantially constant, holding the actual position of the pin substantially constant, pressurizing the device, and testing the pressurized device by monitoring the actual force over time.

The method of the present teachings for testing a device can include, but is not limited to including, setting a target first characteristic of a pressure actuator, setting a target second characteristic of the pressure actuator, and adjusting the pressure actuator. The pressure actuator having an actual first characteristic and an actual second characteristic. The adjusting can include enabling the actual first characteristic to approach the target first characteristic, and enabling the actual second characteristic to approach the target second characteristic. The method can include stopping the adjusting when the first of the actual first characteristic substantially equals the target first characteristic, or the actual second characteristic substantially equals the target second characteristic happens. The method can include adjusting the actual first characteristic to maintain the target second characteristic substantially constant, and testing the device by monitoring the actual first characteristic over time.

The system of the present teachings for testing a device can include, but is not limited to including, at least one platform, at least one holder mount operably coupled with the platform, at least one device holder operably coupled with the holder mount, at least one device cover operably coupled with the holder mount, and at least one device cage insertably coupled with the at least one device holder. The device cage can house the device. The system can include at least one pressure actuator assembly substantially aligned with the device cage at pre-selected test points, and at least one controller setting a target first characteristic of the at least one pressure actuator assembly. The at least one pressure actuator assembly can include an actual first characteristic, and the at least one controller can set a target second characteristic of the at least one pressure actuator assembly. The at least one pressure actuator assembly can include an actual second characteristic, and the at least one controller can adjust the at least one pressure actuator assembly. The adjusting can enable the actual first characteristic to approach the target first characteristic, can enable the actual second characteristic to approach the target second characteristic, and can stop the adjusting when the first of the actual first characteristic substantially equals the target first characteristic, or when the actual second characteristic substantially equals the target second characteristic happens. The at least one controller can adjust the actual first characteristic to maintain the target second characteristic substantially constant. The at least one controller can test the device by monitoring the actual first characteristic over time.

The actual first characteristic can optionally include an actual force and the target first characteristic can optionally include a target force. The actual second characteristic can include actual position and the target first characteristic can include target position. The pressure actuator assembly can optionally include an actuator arm that can couple electronic and mechanical movement means to move and position a pin actuator. The pin actuator can provide the target force on the device. The pressure actuator assembly can optionally include a linear actuator moving the actuator arm towards the target position. The actuator arm can force the device based at least on commands provided by the at least one controller. The pressure actuator assembly can optionally include an actuator mount coupling the linear actuator with a controller housing enclosing the at least one controller. The actuator mount can optionally include fastening cavities coupling the actuator mount with a platform. The actuator mount can optionally include actuator mounting cavities accommodating at least one alignment peg. The pressure actuator assembly can optionally include a motor interface that can couple a motor to the linear actuator. The linear actuator can include operable coupling with a slide block. The slide block can include operable coupling with the actuator arm. The slide block can travel along the linear actuator, and can change the actual position of the actuator arm, moving the actuator arm towards the target position. The system can optionally include a communications means that can couple the pressure actuator assembly with the at least one controller.

The test system of the present teachings for testing at least one device can include, but is not limited to including, at least one force actuator and a processor that can access at least one description of the at least one device. The processor can create command information based at least on the at least one description, and the processor can receive feedback from the at least one force actuator. The test system can include a controller that can access the motion information. The controller can create at least one control command based on the command information. The controller can test the at least one device by controlling the at least one force actuator based on the at least one control command.

The controller can optionally include a group processor managing at least one group. Each group can include either an active or an inactive status. Each of the active groups can include at least one node object. The group processor can access one of the control commands for each of the node objects. The controller can optionally include a node processor that can update the at least one node object based on the command information, and at least one actuator driver that can relay the at least one control command between the updated at least one node object and at least one hardware device. The at least one actuator driver can communicate the at least one control command to the at least one hardware device through at least one hardware driver. The test system can optionally include a command interface that can provide the control information to the at least one node processor, and can receive sensor information from at least one sensor processor. The test system can optionally simultaneously control multiple of the at least one force actuators.

BRIEF DESCRIPTION OF THE DRAWINGS

The present teachings will be more readily understood by reference to the following description, taken with the accompanying drawings, in which:

FIG. 5C is a schematic diagram of the disposable base top/top gasket/membrane gasket of the exemplary device that can be subject to the applied force of the present teachings;

FIG. 25B-1 is a schematic block diagram of a second hardware configuration of the system of the present teachings;

FIG. 25B-2 is a schematic block diagram of a third hardware configuration of the system of the present teachings;

DETAILED DESCRIPTION

A configuration of the system and method for applying pressure to a device of the present teachings is discussed in detail herein in relation to testing of diaphragm valves, prosthetic arms, and other applications. Various types of applications may take advantage of the features of the present teachings.

Figure 1:
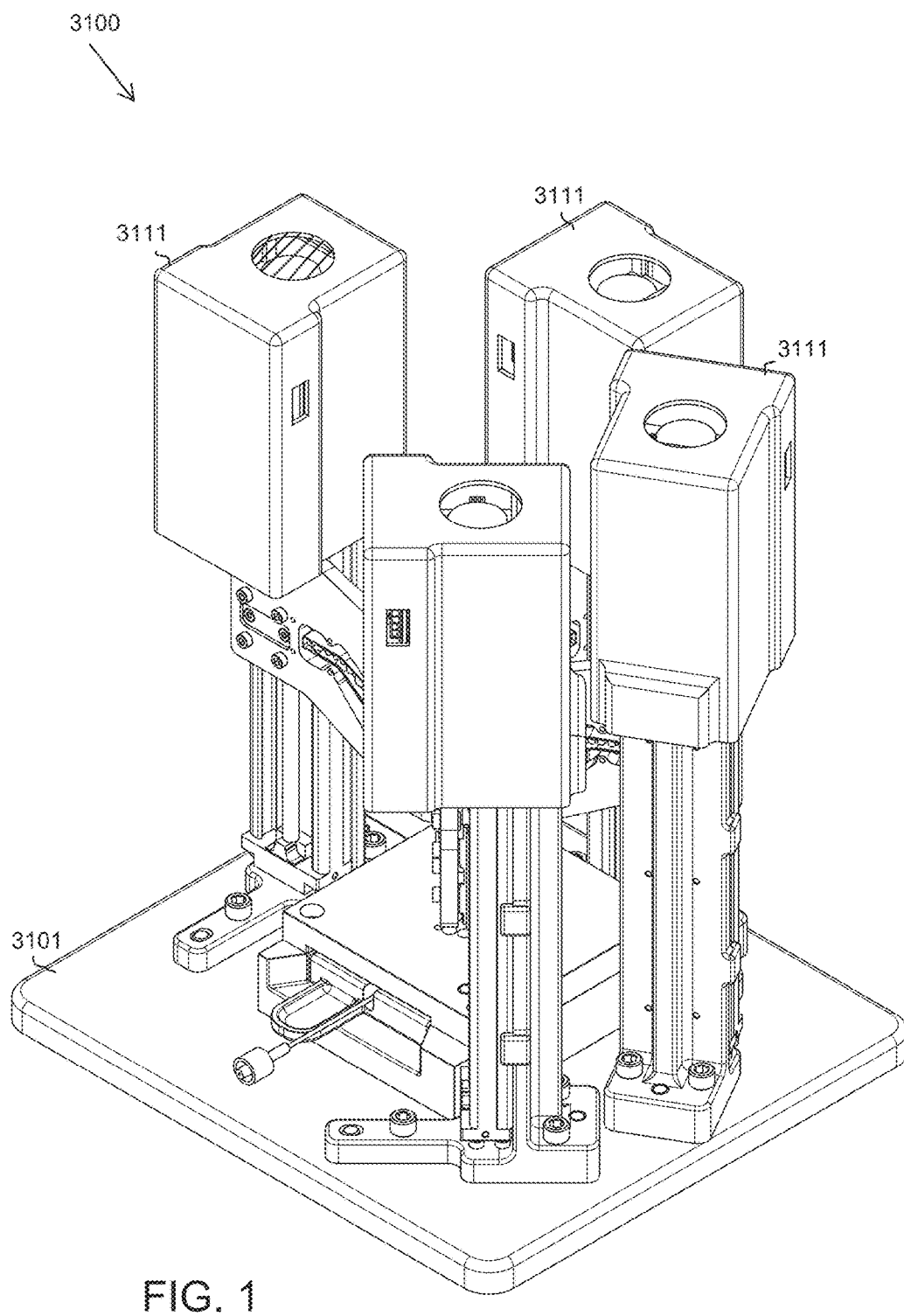
FIG. 1 is a schematic diagram of a side view of the force actuation system of the present teachings.
Figure 2:
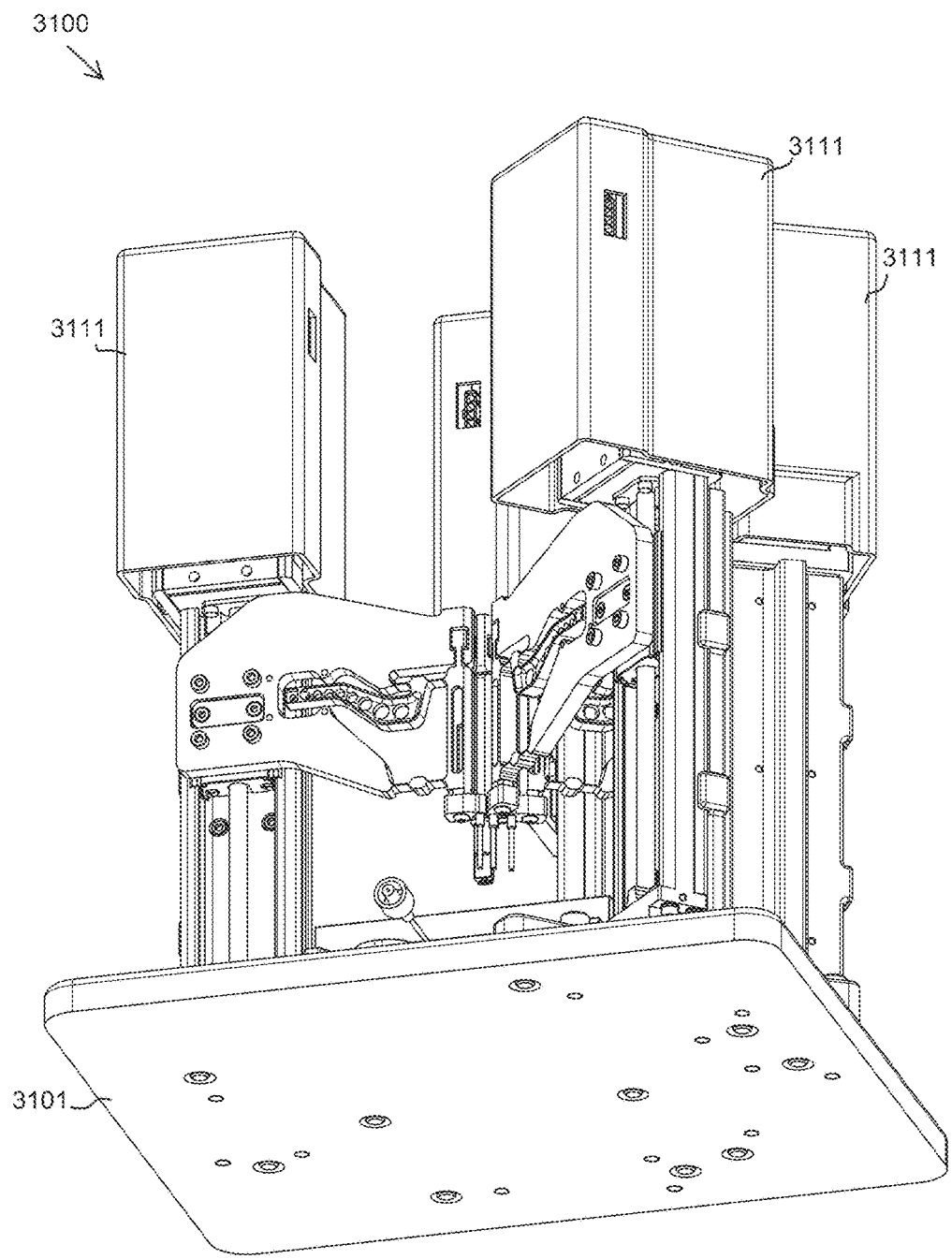
FIG. 2 is a schematic diagram of an under front view of the force actuation system of the present teachings.

Referring now to FIGS. 1 and 2, force actuation system 3100 for applying force to a device can accommodate the placement of a device with respect to the forcing mechanism, the controlled actuation of the forcing mechanism, and the monitoring of results. The forcing mechanism, also referred to herein as a pressure actuator, can be associated with actual and target characteristics such as, for example, actual and target forces. The target characteristics can be selected based at least on the device. The pressure actuator can be adjusted to enable the actual characteristics to approach the target characteristics, and the adjustment can be stopped when one of the actual characteristics substantially equals its counterpart target characteristic. Conversely, at least one characteristic, for example, force, can be held constant while the position of actuator arm 3111H (FIG. 19) changes. Force actuation system 3100 can include, but is not limited to including, at least one pressure actuator assembly 3111 that can be operably coupled with platform 3101. At least one pressure actuator assembly 3111 can provide the forcing mechanism, controlled actuation, and result monitoring. Force actuation system 3100 can accommodate a placement and alignment means for the device that can be operably coupled with at least one pressure actuator assembly 3111. In some configurations, multiple of at least one pressure actuator assembly 3111 can be provided that can force multiple parts of the device, and/or multiple devices sequentially and/or in parallel, depending on the application. For example, if a single device includes multiple membranes, multiple pressure actuator assemblies 3111 can be aligned with each of the multiple membranes. Pressure actuator assemblies 3111 can exercise the multiple membranes asynchronously or in parallel, for example, to exercise the entirety of the device versus the individual membranes. Pressure actuator assemblies 3111 can exercise individual of the multiple membranes completely or partially independently by, for example, controlling the timing of pin actuation. Force actuation system 3100 can apply force to many types and styles of devices. Actuator assembly 3111 can be positioned on platform 3101, and device cover 3107 can include cavities, that can together accommodate any number of device geometries.

Figure 3:
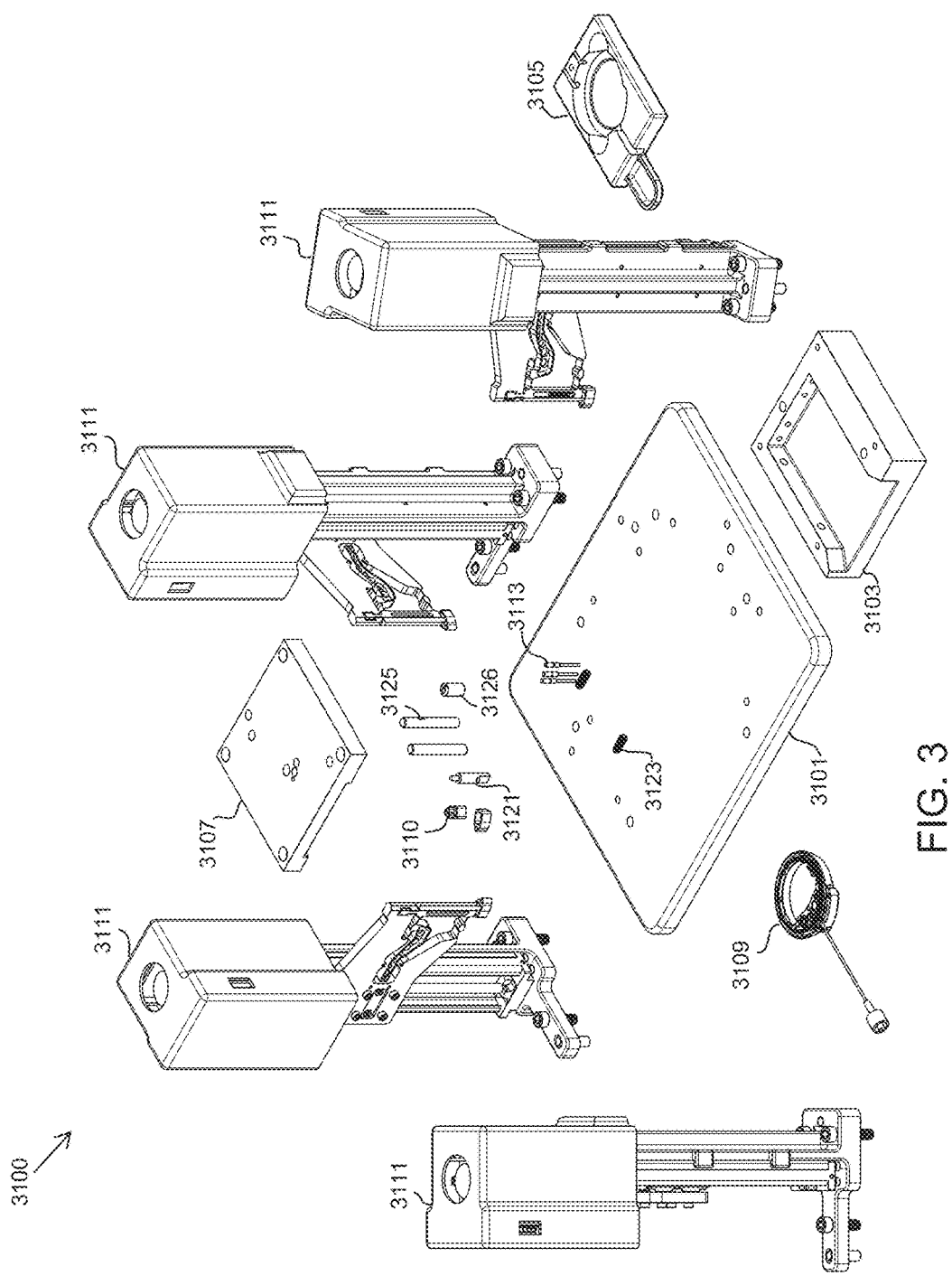
FIG. 3 is a schematic diagram of an exploded view of the force actuation system of the present teachings.

Referring now to FIG. 3, force actuation system 3100 can include, but is not limited to including, accommodations for device 3109. Each of these accommodations can be modified for a particular device. The description herein relates to a cassette, but force actuation system 3100 is not limited to applying force to the particular described cassette, or cassettes in general. Device accommodations can include, but are not limited to including, at least one holder mount 3103 operably coupled with platform 3101, at least one device holder 3105 operably coupled with holder mount 3103, and at least one device cover 3107 operably coupled with holder mount 3103. Force actuation system 3100 can include at least one pin actuator 3113 that can provide the forcing interface between at least one device 3109 and pressure actuator assembly 3111. At least one device 3109 can be insertably coupled with at least one device holder 3105. Force actuation system 3100 can include end effector offset 3110 that can couple pressure actuator assembly 3111 with at least one pin actuator 3113. Pressure actuator assembly 3111 can be coupled with platform 3101 using, for example, but not limited to at least one alignment peg 3125. Set screws 3123 and 3126 can provide side and top mounting and alignment of device holder 3105. Pressure seal 3121 can enable fluid-tight forcing.

Figure 4:
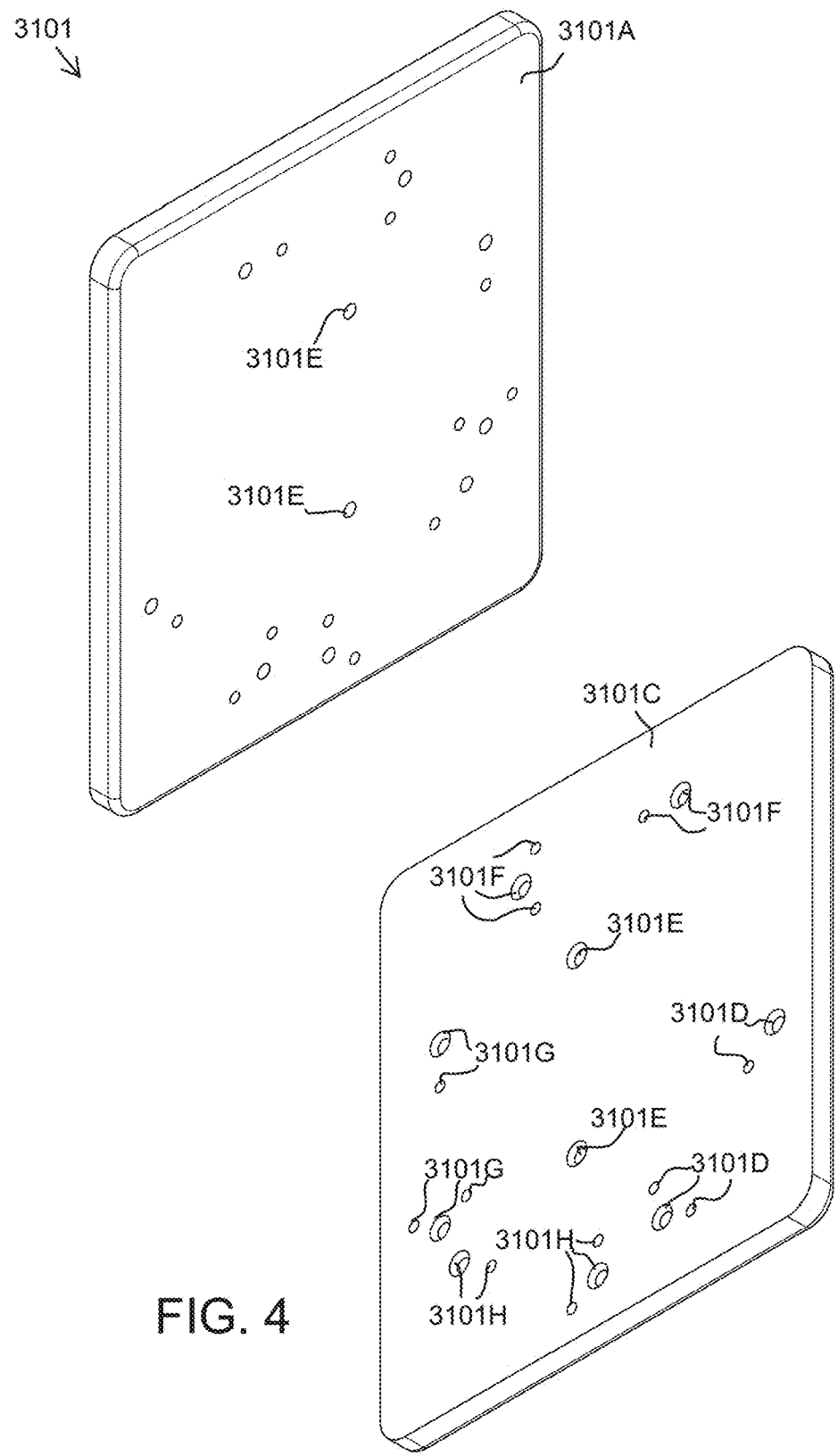
FIG. 4 is a schematic diagram of the platform of the present teachings.
Figure 9:
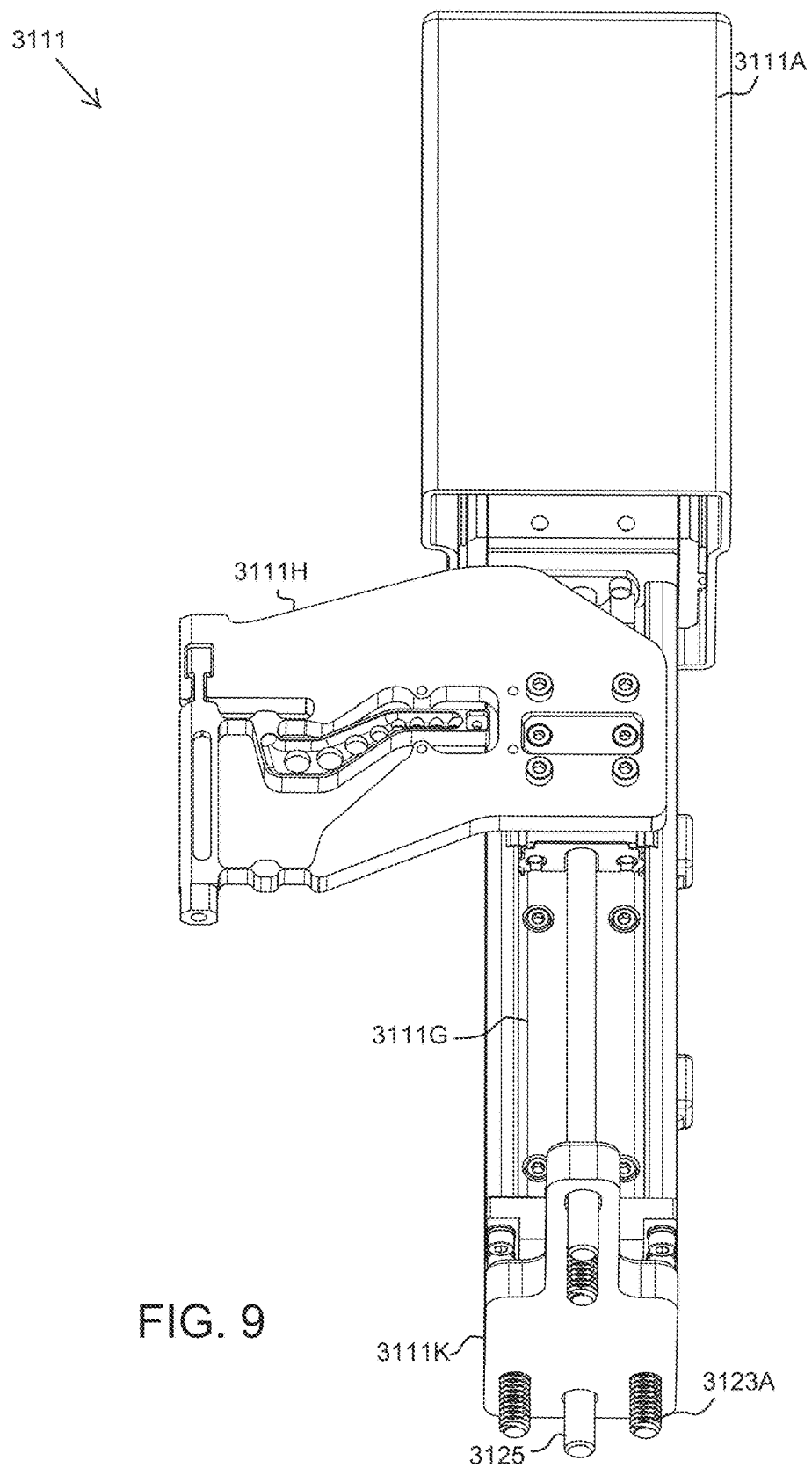
FIGS. 9 and 10 is a schematic diagram of first and second side views of the pressure actuator assembly of the present teachings.

Referring now primarily to FIG. 4, platform 3101 can stably support the elements of force actuation system 3100. Platform 3101 can be any size, and can include any number of mounting cavities in any configuration that can accommodate the placement the number of pressure actuator assemblies 3111 (FIG. 9) appropriate for the particular device to be forced. Platform 3101 can include, but is not limited to including, platform first side 3101A that can accommodate mounting of, for example, but not limited to, at least one holder mount 3103 (FIG. 5) and at least one pressure actuator assembly 3111 (FIG. 9). Platform 3101 can include platform second side 3101C that can accommodate, for example, four actuator mounting cavities 3101D/F/G/H and two platform mounting cavities 3101E. For example, a first of at least one pressure actuator assembly 3111 (FIG. 9) can be aligned with and mount at actuator mounting cavities 3101D, a second of at least one pressure actuator assembly 3111 (FIG. 9) can be aligned with and mount at actuator mounting cavities 3101F, a third of at least one pressure actuator assembly 3111 (FIG. 9) can be aligned with and mount at actuator mounting cavities 3101G, and a fourth of at least one pressure actuator assembly 3111 (FIG. 9) can be aligned with and mount at actuator mounting cavities 3101H. In some configurations, mounting cavities 3101D/E/F/G/H can optionally accommodate fastener flush mount. Actuator mounting cavities 3101D/F/G/H can each include, for example, but not limited to, five cavities that can include various sizes and shapes of cavities.

Figure 5:
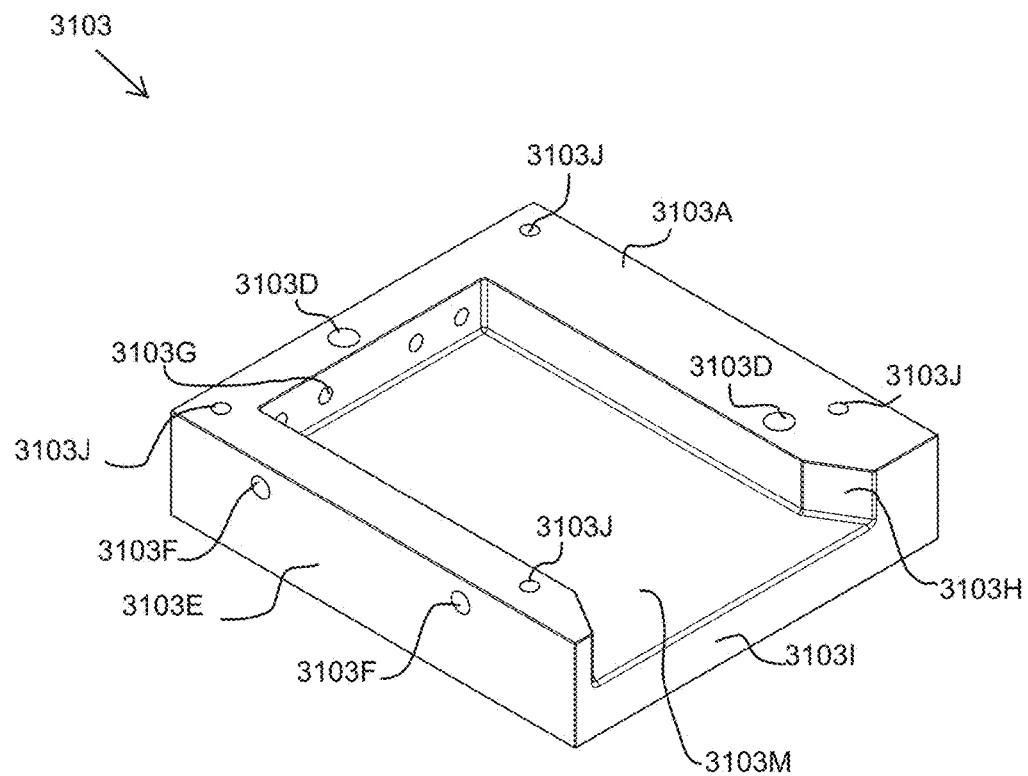
FIG. 5 is a schematic diagram of top and bottom views of the holder mount of the present teachings.
Figure 5:
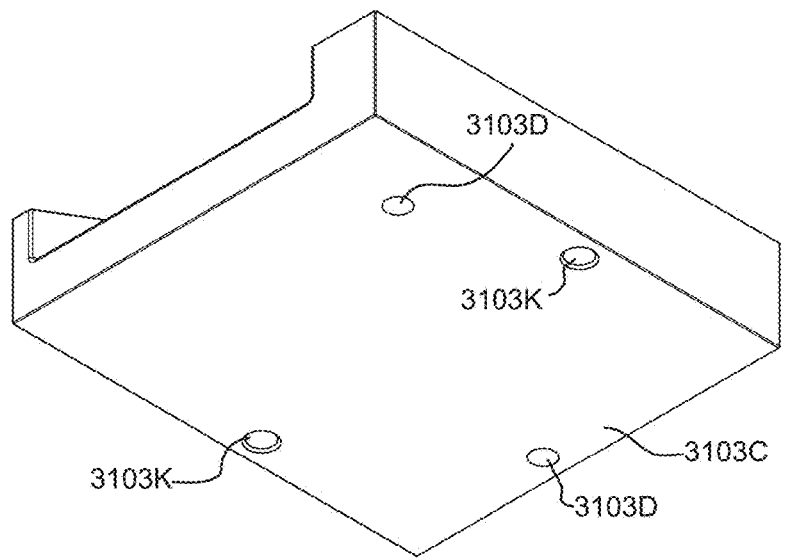
Figure 5A:
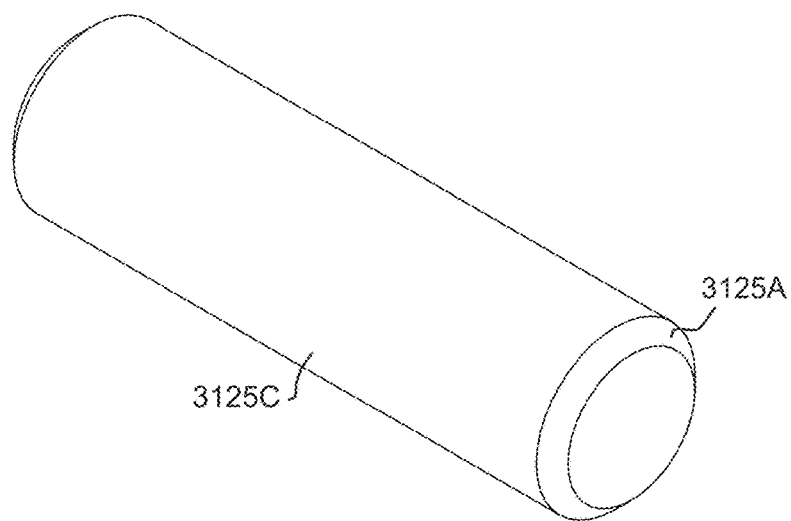
FIG. 5A is a schematic diagram of first and second views of the alignment peg of the present teachings.
Figure 5A:
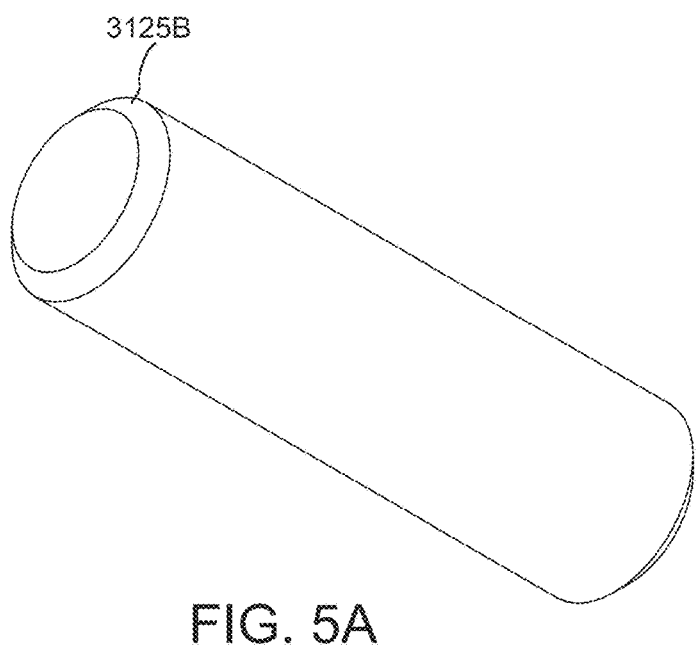
Figure 5B:
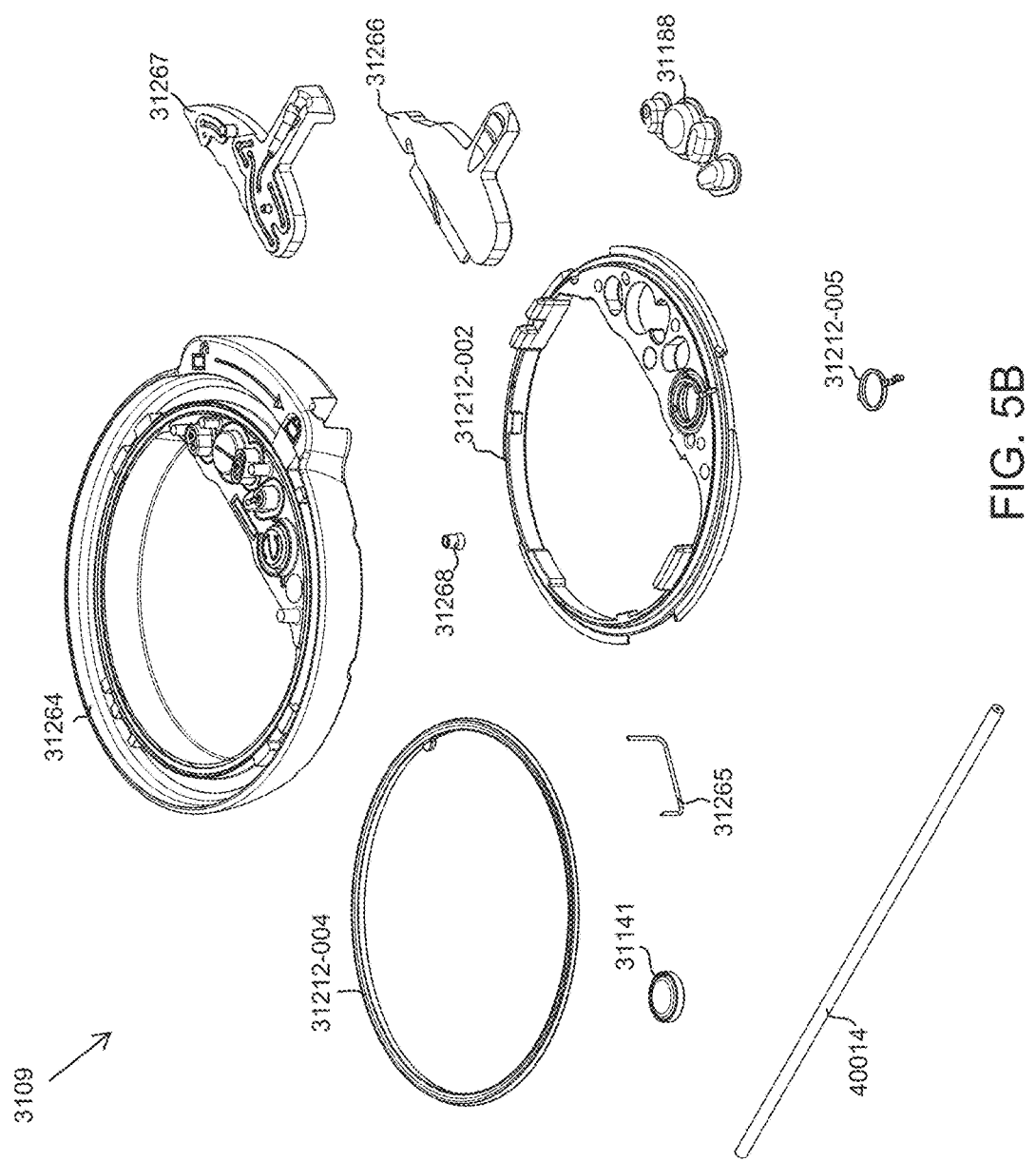
FIG. 5B is a schematic diagram of an exploded view of an exemplary device that the system of the present teachings can accommodate.
Figure 6:
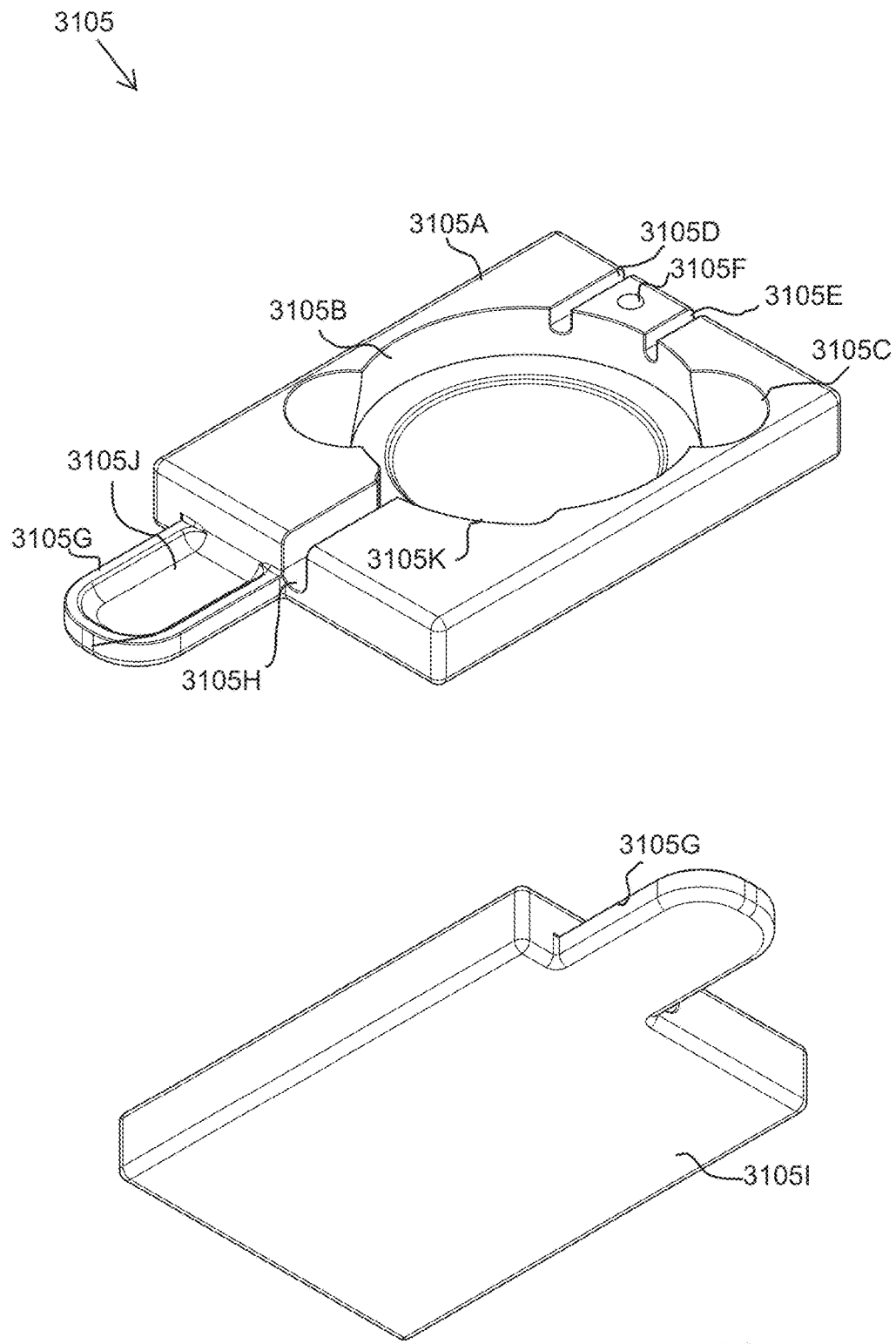
FIG. 6 is a schematic diagram of top and bottom views of the device cage of the present teachings.

Referring now primarily to FIG. 5, at least one holder mount 3103 can provide secure mounting and venting for the device to which pressure is to be applied, for example, but not limited to, device 3109 (FIG. 5B). Holder mount 3103 can be any size and shape, and can include any number of mounting cavities appropriate for a particular device to be forced. Holder mount 3103 described herein include features that can enable accurate forcing such as, for example, cavity configurations and set screw features. At least one holder mount 3103 can optionally accommodate, on holder mount first side 3103A, drop-on and/or slide-in mounting of device 3109 (FIG. 5B) in device holder cut-out 3103M. Holder mount first side 3103A can include holder mount first edge 3103E that can include edge mounting cavities 3103F that can accommodate operable coupling between at least one holder mount 3103 and at least one device cage 3105 (FIG. 6). Device holder cut-out 3103M can include cut-out mounting cavities 3103G that can accommodate further operable coupling between at least one holder mount 3103 and at least one device cage 3105 (FIG. 6), and can further provide venting for device 3109 (FIG. 5B). Holder mount first side 3103A can include lid mounting cavities 3103J that can accommodate placement and operable coupling between at least one lid 3107 (FIG. 7A) and at least one holder mount 3103. At least one holder mount 3103 can include holder mount third edge 3103I that can optionally include at least one cut-out 3103M. At least one cut-out 3103M can accommodate slide-in mounting of device cage 3105 (FIG. 6). At least one cut-out 3103M can be any shape and size, and the shape and size can depend, for example, but not limited to, on the shape and size of at least one device cage 3105 (FIG. 6). Holder mount third edge 3103I can optionally form an enclosure in which at least one cut-out 3103M can accommodate drop-in mounting of at least one device cage 3105 (FIG. 6). At least one cut-out 3103M can include at least one beveled edge 3103H that can facilitate placement of at least one device cage 3105 (FIG. 6). At least one holder mount 3103 can include, but is not limited to including, holder mount second side 3103C that can include at least one holder platform mounting cavity 3103K. At least one cavity 3103K can optionally accommodate flush mounting of fasteners. Holder platform mounting cavities 3103D can accommodate fasteners that can operably couple at least one holder mount 3103 with platform 3101 (FIG. 3). At least one alignment peg 3125 (FIG. 5A) can, for example, but not limited to, provide the operable coupling and alignment between at least one holder mount 3103 and platform 3101 (FIG. 3) at mounting cavities 3103K. At least one alignment peg 3125 (FIG. 5A) can also provide alignment and mounting features between at least one holder mount 3103 and at least one lid 3107 (FIG. 7A) using, for example, but not limited to at least one alignment peg 3125 (FIG. 5A) encased within at least one peg mounting cavity 3103D.

Referring now to FIG. 5A, alignment peg 3125 can include, for example, but not limited to, cylindrical body 3125C, first end 3125A, and second end 3125B. First end 3125A and second end 3125B can optionally include beveled edges.

Referring now primarily to FIG. 5B, exemplary device 3109 is described herein to illustrate the features of force actuation system 3100 (FIG. 1). Many other types and sizes of devices can be forced with force actuation system 3100 (FIG. 1). Exemplary device 3109 can include, but is not limited to including, a cassette, for example, a disposable housing assembly as described in detail in, for example, '646. The disposable housing assembly can include disposable base bottom 31264 operably coupled with disposable base top/top gasket/membrane gasket 31212-002/004/005. Membrane gasket 31212-005 can retain coated membrane 31141 in position in disposable base top 31212-002. Fluid, including air, can enter the cassette through a luer lock adapter, and composite tube 40014, and can further continue into the cassette through fluid path cover 31267. Fluid path cover 31267 can be operably connected to bent-u needle 31265. Bent-u needle 31265 can be held in place by needle gasket 31268 and can provide a channel for fluid flow from composite tube 40014 to fluid path membrane 31188. Disposable base needle cover 31266 can cover and protect fluid path cover 31267. An o-ring can secure the operable coupling between bent-u needle 31265 and disposable base top 31264.

Referring now primarily to FIG. 5C, fluid path membrane 31188 (FIG. 5B) can allow for pumping and flow of fluid. Disposable base top 31212-002 can include one or more openings 31212D that can expose at least a portion of fluid path membrane 31188 (FIG. 5B) for actuation by pin actuator 3113 (FIG. 8C). Openings 31212D can allow the fill volume to be controlled during filling of well 31264C.

Figure 5D:
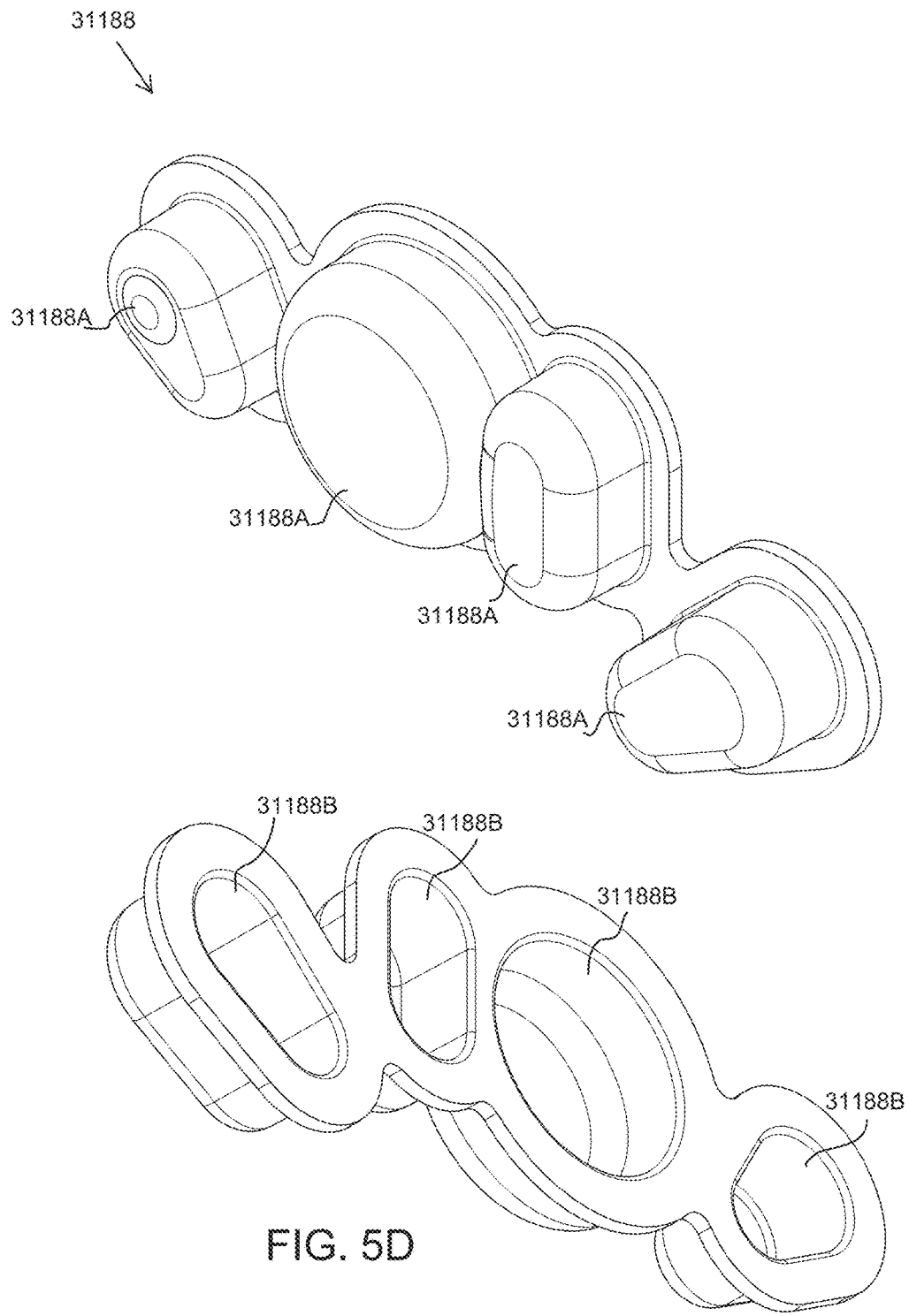
FIG. 5D is a schematic diagram of top and bottom views of the fluid path membrane of the exemplary device that can be subject to the applied force of the present teachings.

Referring now to FIG. 5D, the disposable housing assembly can include fluid path membrane 31188. Fluid path membrane 31188 can include at least partial disposal over volcano valves and a pumping recess included on/within disposable base bottom 31264 (FIG. 5B). Fluid path membrane 31188 may include a flexible material, e.g., which may be selectively engaged against volcano valves by pin actuator 3113 (FIG. 8C) at membranes 31188A to force the disposable housing assembly. Any of membranes 31188A can be forced simultaneously and/or individually by depressing at least one of membranes 31188A and monitoring the result. Depressed membranes 31188A can alter the shapes of valve cavities 31188B.

Figure 7A:
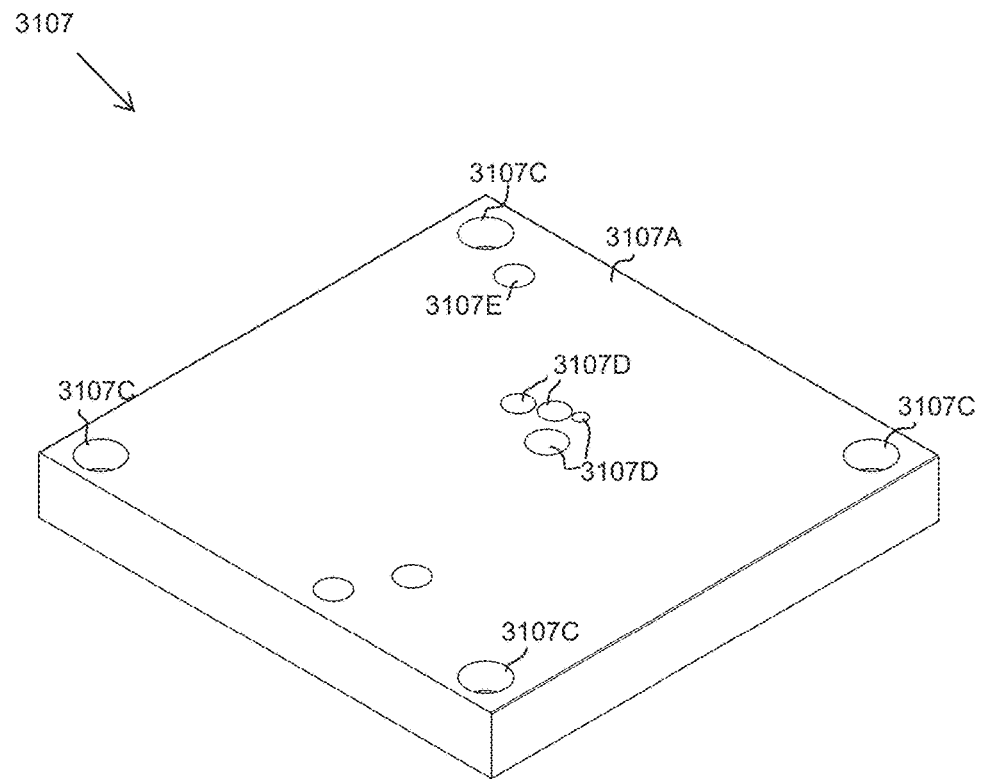
FIG. 7A is a schematic diagram of top and bottom views of the lid of the present teachings.
Figure 7A:
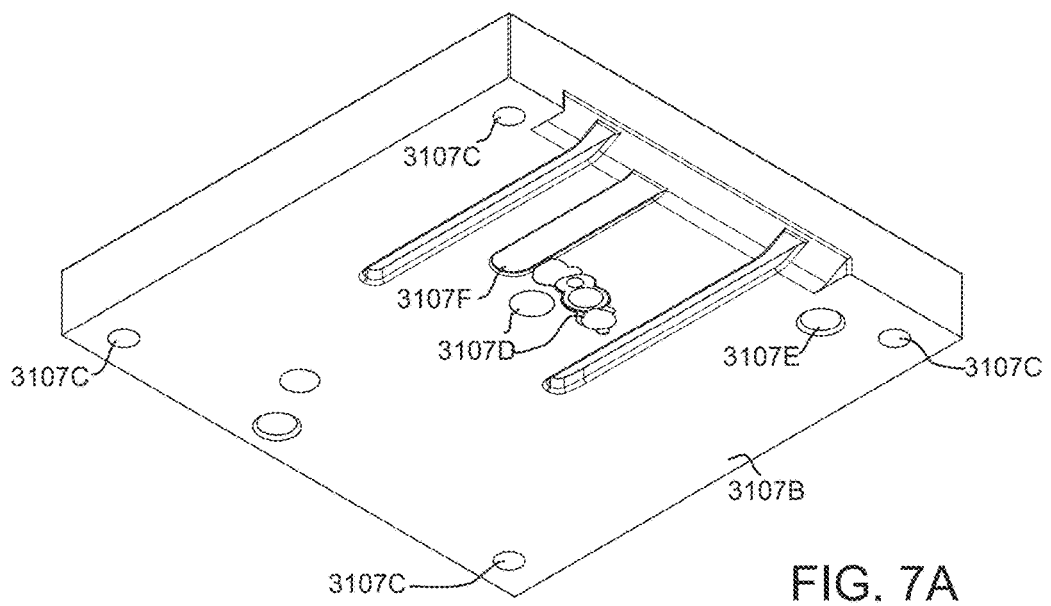

Referring now to FIG. 6, at least one device cage 3105 can accommodate, for example, device 3109 (FIG. 5B) that can include, but is not limited to including, an insulin pump cassette such as those described in U.S. Pat. No. 8,496,646 entitled Infusion Pump Assembly, issued on Jul. 30, 2013 ('646). At least one device cage 3105 can include, but is not limited to including, cage first side 3105A. Cage first side 3105A can include device well 3105B having at least one well ear 3105C that can accommodate, for example, removing of device 3109 (FIG. 5B), and having device positing indent 3105K that can accommodate, for example, positioning of device 3109 (FIG. 5B). At least one device cage 3105 can include at least one cage handle 3105G that can optionally include thumb rest 3105J. In some configurations, cage first side 3105A can include cavity 3105F that can accommodate, for example, but not limited to, flexible-tipped set screw 3126 (FIG. 7B) that can provide alignment and fastening of at least one device cage 3105 to at least one lid 3107 (FIG. 7A). Cage first side 3105A can include tube well 3105H that can accommodate composite tube 40014 (FIG. 5B), for example. Wells 3105D and 3105E can accommodate venting and mounting features, for example. At least one device cage 3105 can include cage second side 3105I that can, for example, include a smoothed surface that can accommodate insertion and removal of at least one device cage 3105 from at least one holder mount 3103 (FIG. 5).

Referring now to FIG. 7A, at least one lid 3107 can include at least one cavity 3107D configured to accommodate forcing of any device. At least one lid 3107 can provide a cover for device 3109 (FIG. 5B) and can include operable coupling with device holder 3103 (FIG. 5) using flexible-tip set screw 3126 (FIG. 5A). At least one lid 3107 can include lid first side 3107A and lid second side 3107B. Lid first side 3107A can provide an interface with pressure actuator assembly 3111 (FIG. 9), and can include at least one device interface cavity 3107D and device cage cavities 3107C. At least one device cage cavity 3107C can operably couple with at least one lid mounting cavity 3103) (FIG. 5) through at least one type of fastener that can include, but is not limited to including, bolts, screws, hook-and-eye, and glue. At least one device interface cavity 3107D can accommodate, but is not limited to accommodating, at least one pin actuator 3113 (FIG. 8C). Coupling cavity 3107E can operably couple with at least one holder mounting cavity 3103D (FIG. 5). Lid second side 3107B can optionally include cavities 3107F/G/H/J that can accommodate, for example, protrusions from a particular device.

Figure 7B:
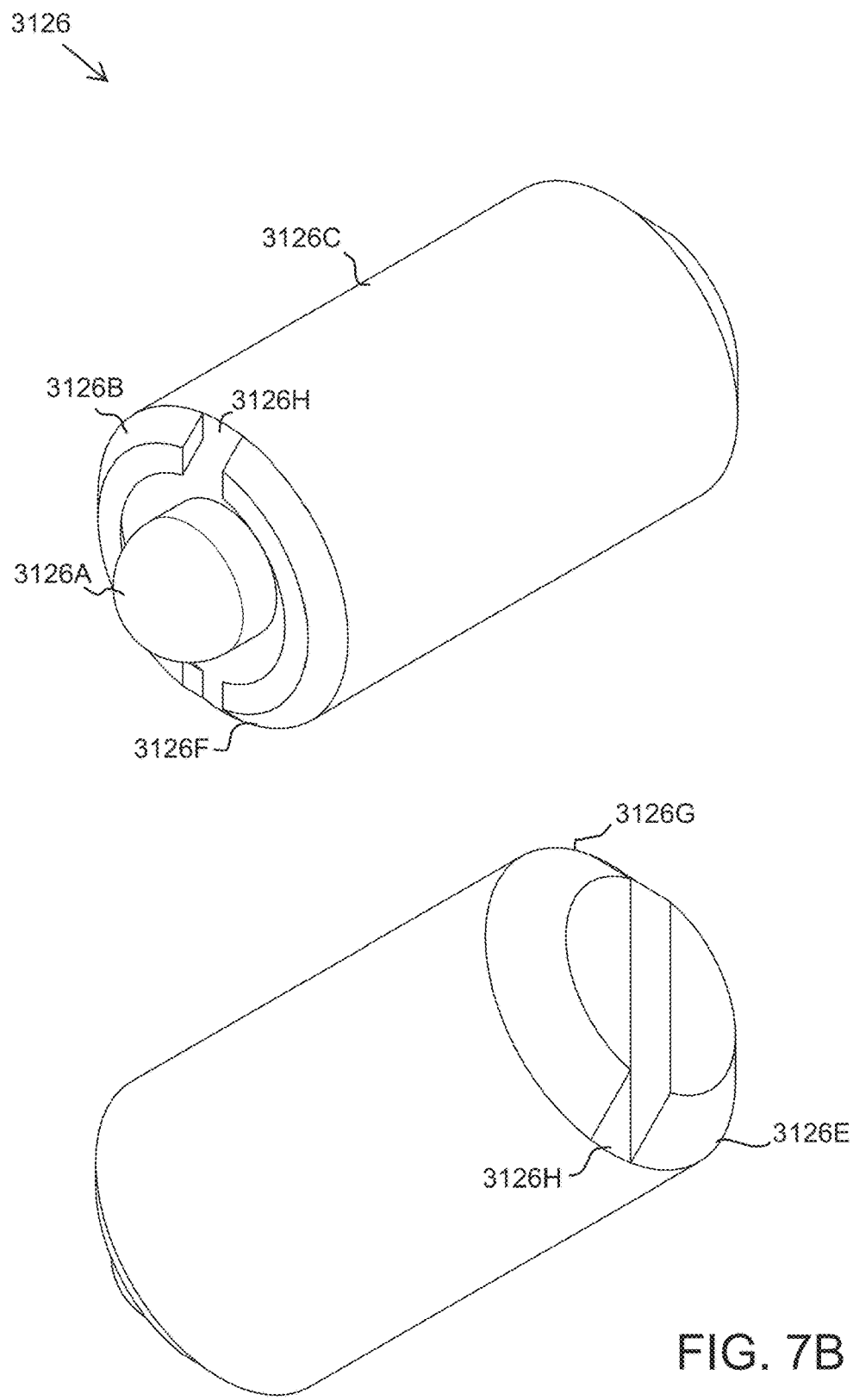
FIG. 7B is a schematic diagram of first and second views of the flexible tip set screw of the present teachings.

Referring now to FIG. 7B, flexible-tip set screw 3126 can operably couple at least one lid 3107 (FIG. 7A) to device cage 3105 (FIG. 6) at indent 3105F (FIG. 6). Flexible-tip set screw 3126 can include, but is not limited to including, cylindrical body 3126C that can include, but is not limited to including, threading, and can include body first end 3126F and body second end 3126G. Body first end 3126F can include flexible tip 3126A that can enable snap-in placement and accurate alignment of device cage 3105 (FIG. 6). Body first end 3126F can include beveled edges 3126B. Body second end 3126G can include beveled edge 3126E, and can optionally include driver head cavity 3126H that can accommodate, for example, but not limited to, a flat head screw driver. Body second end 3126G can include any type of screw head such as, for example, but not limited to, Philips, Allen, and/or a combination of head types.

Figure 8A:
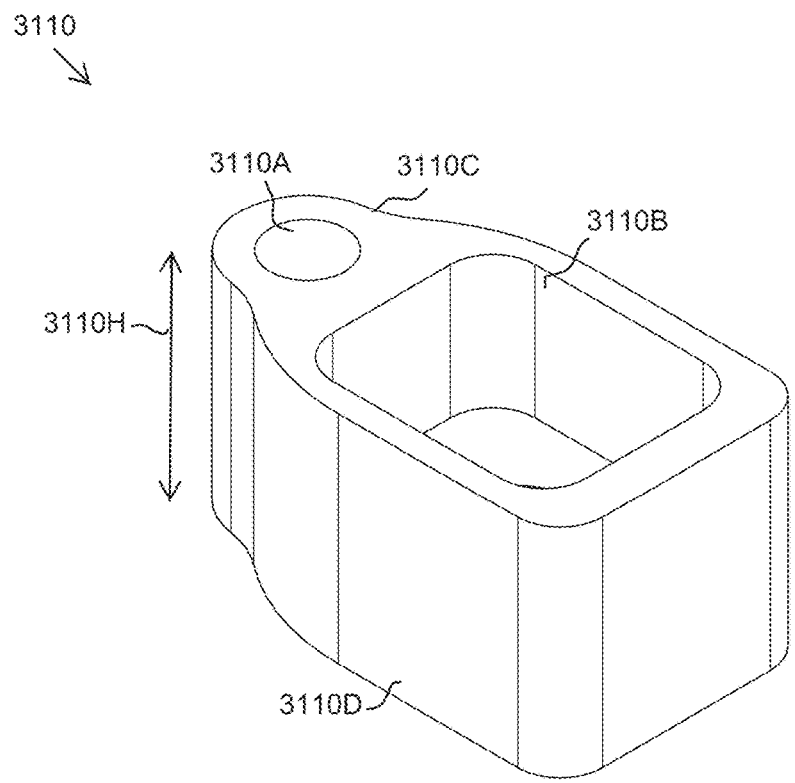
FIG. 8A is a schematic diagram of first and second views of the end effector of the present teacgs.
Figure 8A:
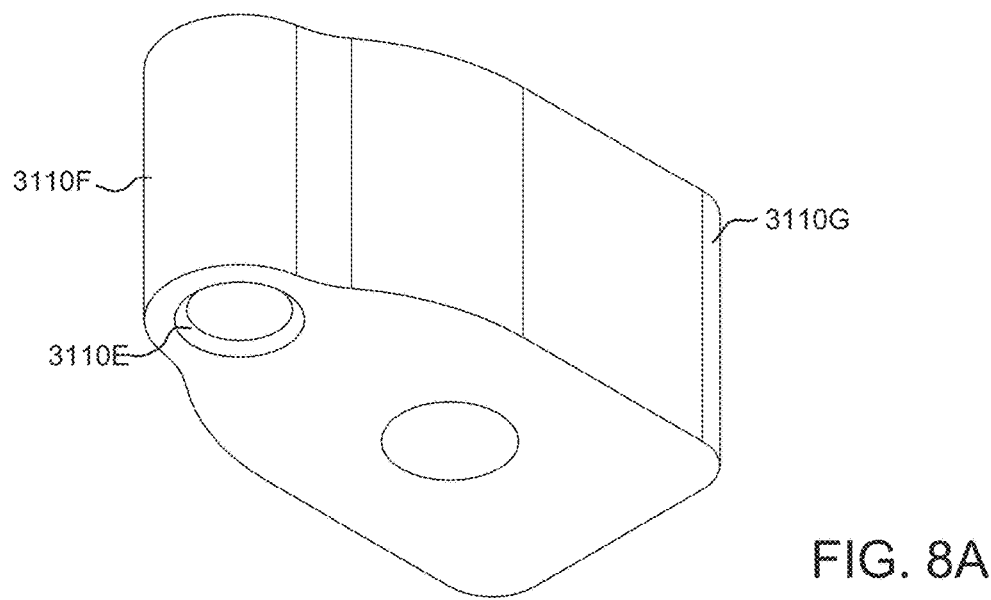
Figure 8B:
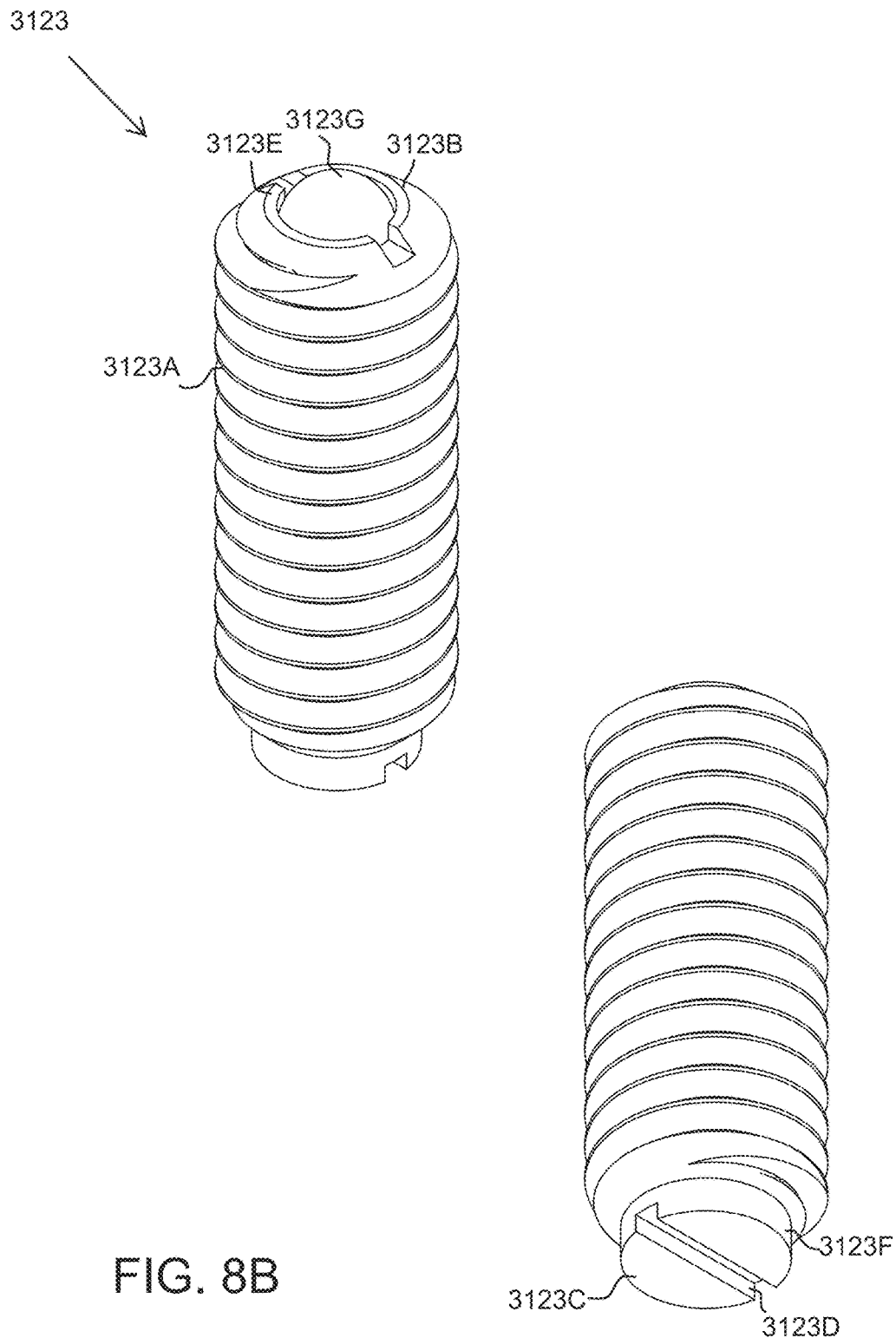
FIG. 8B is a schematic diagram of first and second views of the flexible tip set screw of the present teachings.
Figure 8C:
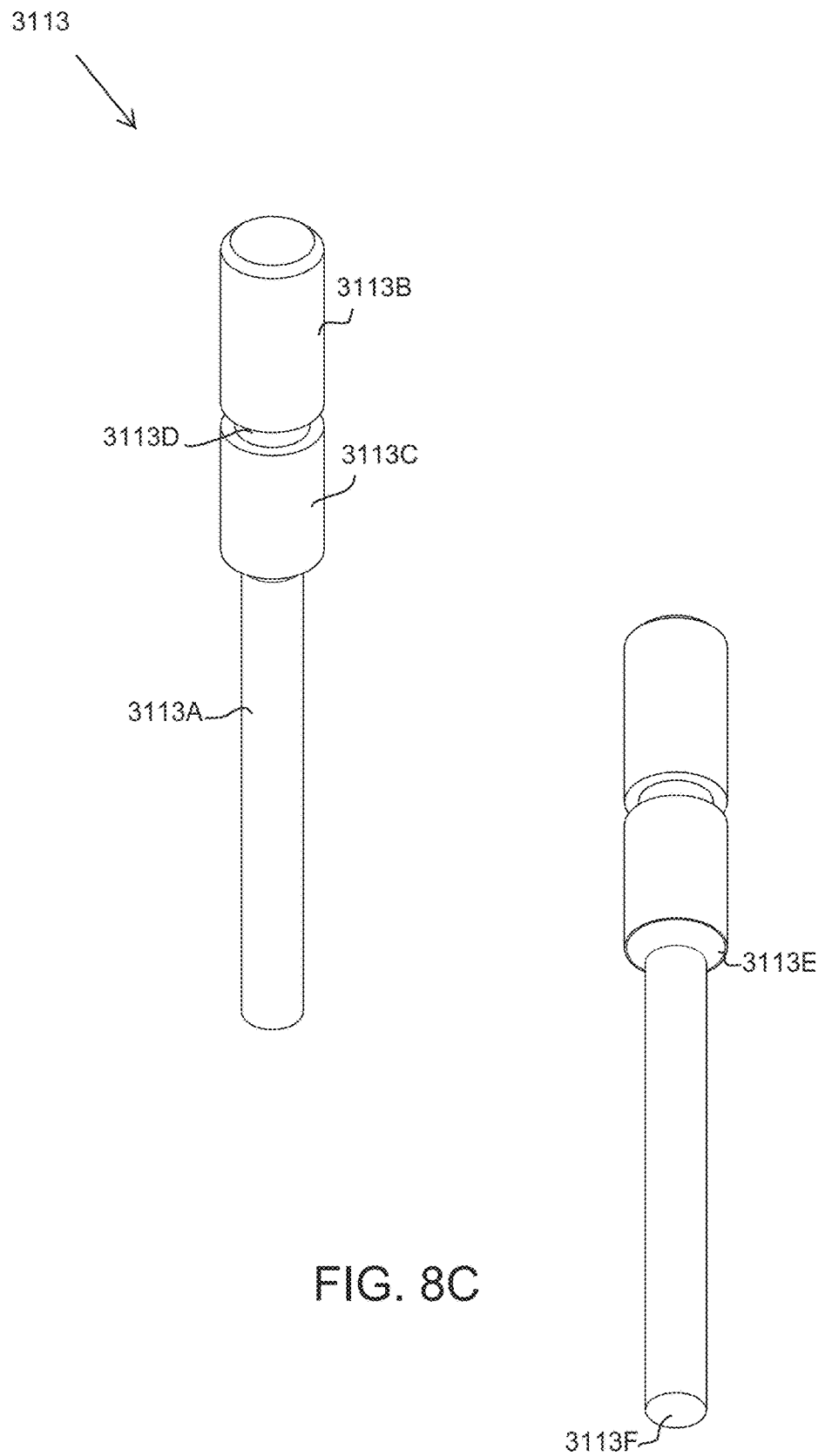
FIG. 8C is a schematic diagram of first and second views of the pin actuator of the present teachings.
Figure 8D:
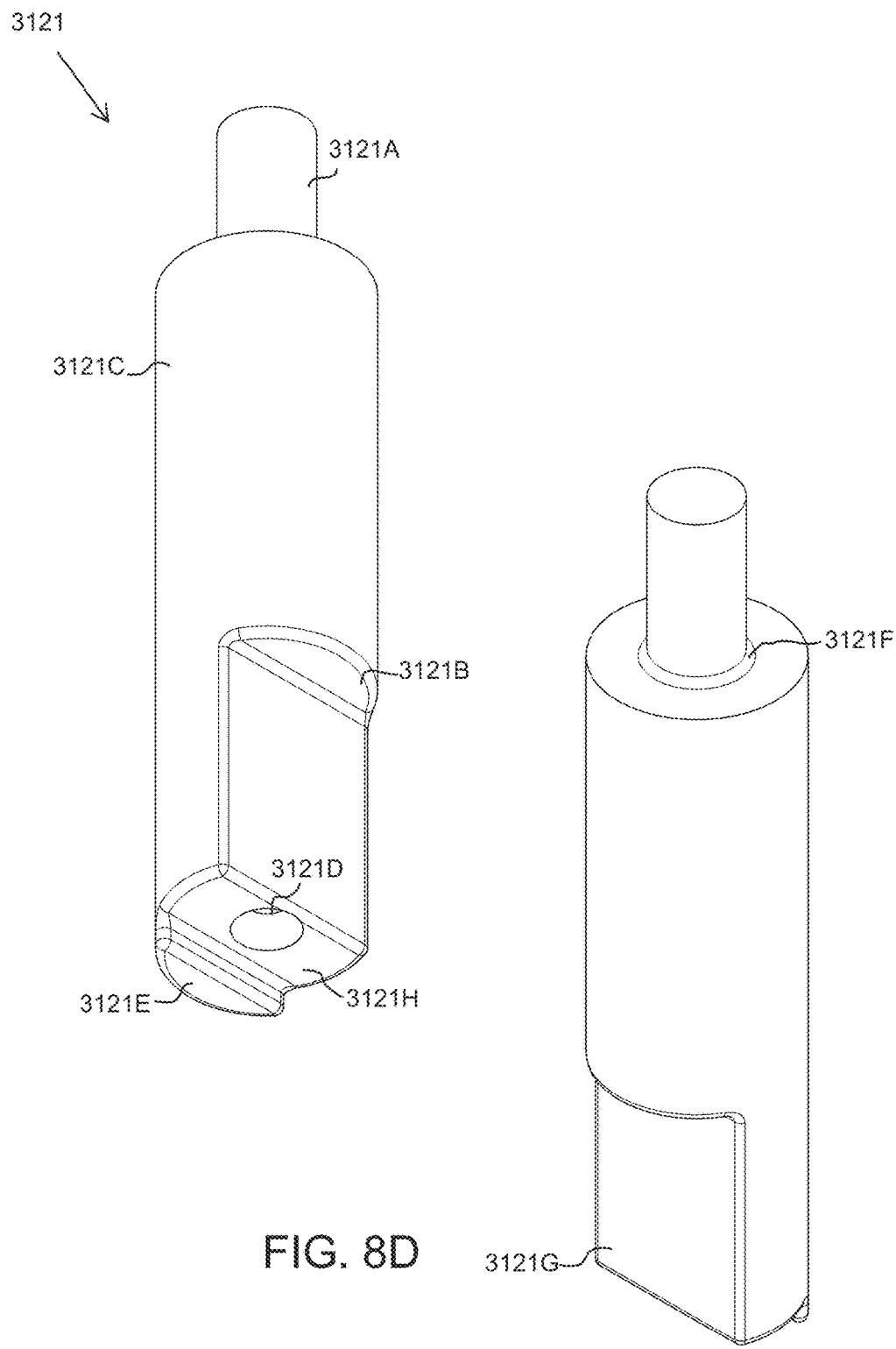
FIG. 8D is a schematic diagram of first and second views of the fluid shutoff actuator of the present teachings.

Referring now to FIG. 8A, end effector offset 3110 can provide an interface between actuator assembly 3111 (FIG. 3) and pin actuator 3113 (FIG. 8C) and/or fluid shutoff actuator 3121 (FIG. 8D). End effector offset 3110 can include, but is not limited to including, arm end cavity 3110B that can house arm end 3111H11 (FIG. 19) and, optionally, fluid shutoff actuator 3121 (FIG. 8D). End effector offset 3110 can include pin actuator cavity 3110A that can house pin actuator 3113 (FIG. 8C). In some configurations, pin actuator cavity 3110A can include beveled edges 3110E for flush mounting. In some configurations, end effector offset 3110 can include first portion 3110C that can be a different size from second portion 3110D. The different portion sizes can form a taper. In some configurations, first portion 3110C can include shaped end 3110F that can be, for example, but not limited to, rounded. In some configurations, end effector offset 3110 can include beveled edges 3110G that can, for example, reduce the overall weight of force actuation system 3100 (FIG. 1). End effector offset 3110 can include depth 3110H that can vary according to the sizes of arm end 3111H1 (FIG. 19) and pin actuator 3113 (FIG. 8C), or for any other reason.

Referring now to FIG. 8B, flexible tip set screw 3123 can provide snap-in fastening and alignment between device holder mount 3103 (FIG. 5) and device cage 3105 (FIG. 6). Set screw 3123 can include threads 3123A that can be any direction, density, diameter, thread count, and length. Set screw 3123 can include screw first end 3123B and screw second end 3123C. Screw first end 3123B can include screwdriver interface 3123E and flexible tip 3123G. Flexible tip 3123G can enable snap-in mounting and alignment of device cage 3105 (FIG. 6) through cavities 3103F (FIG. 5) Screw second end 3123C can include screwdriver interface 3123D that can accommodate, but is not limited to accommodating, flat head, Philips head, and/or Allen wrench screwdrivers. Screw second end 3123C can include protrusion 3123F that can extend set screw 3123 and optionally facilitate access to screwdriver interface 3123D.

Referring now to FIG. 8C, pin actuator 3113 can press upon device 3109 (FIG. 5B) to perform forcing on device 3109 (FIG. 5B). Pin actuator 3113 can be controlled by actuator assembly 3111 (FIG. 9) and can provide pressure on device 3109 (FIG. 5B) at pin head 3113F. Pin actuator 3113 can include, but is not limited to including, first connector stop 3113B and second connector stop 3113C surrounding connector catch area 3113D that, together, can operably couple pin actuator 3113 with end effector offset 3110 (FIG. 8A). Second connector stop 3113C can be terminated with end bulge 3113E that can provide, for example, but not limited to, connective support to pin 3113A. Pin 3113A can be any shape and size, and can be constructed from any type of material suitable for the forcing being performed. Pin actuator can be any length and thickness suitable for the forcing being performed.

Figure 19:
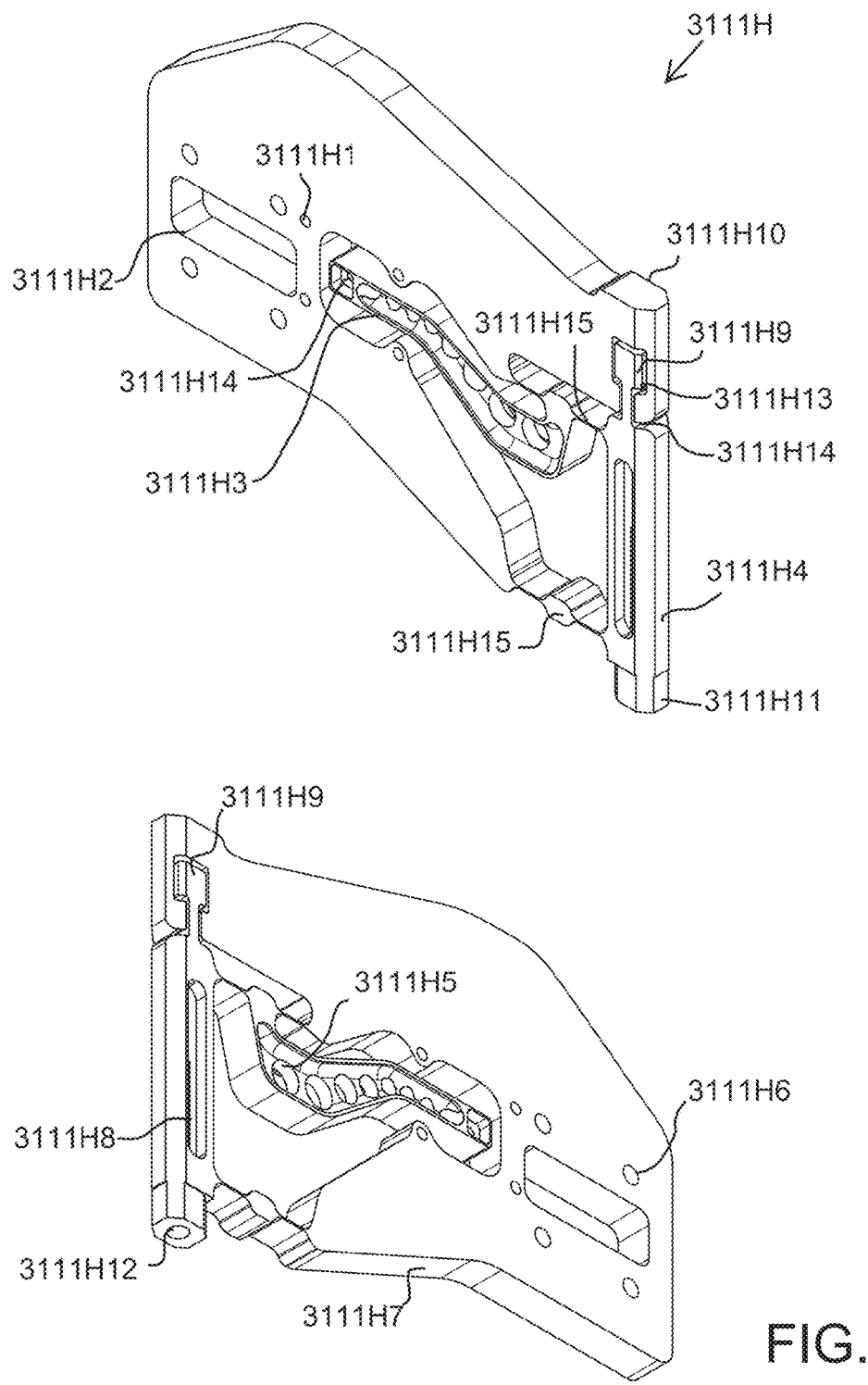
FIG. 19 is a schematic diagram of first and second views of the actuator arm of the present teachings.

Referring now to FIG. 8D, fluid shutoff actuator 3121 can shut down fluid flow from/to bent-u needle 31265 (FIG. 8I) at first fluid pathway 31265D (FIG. 8I). Fluid shutoff actuator 3121 can include, but is not limited to including, body 3121C that can include, but is not limited to including, a substantially non-textured cylindrical surface. Body 3121C can optionally include a textured surface and a non-cylindrical shape. Fluid shutoff actuator 3121 can include overhang 3121B that can provide a stopping mechanism that can disable further movement towards device 3109 (FIG. 5B) if necessary. Body cut-out 3121G can streamline fluid shutoff actuator 3121 to fit various-sized openings in lid 3107 (FIG. 7A), and can accommodate the shape of device 3109 (FIG. 5B). Fluid shutoff actuator 3121 can include peg fitting 3121A that can operably couple fluid shutoff actuator 3121 with arm 3111H (FIG. 19) at cavity 3111H12 (FIG. 19). Peg fitting 3121A can include connective support 3121F that can enhance the coupling between body 3121C and peg fitting 3121A. Cutoff base 3121H can include cavity 3121D that can enable operable coupling between fluid shutoff actuator 3121 and a pressurizing device such as, for example, pin actuator 3113 (FIG. 8C). Finger 3121E can provide a pressure point to inhibit fluid flow from first fluid pathway 31265D (FIG. 8I).

Figure 10:
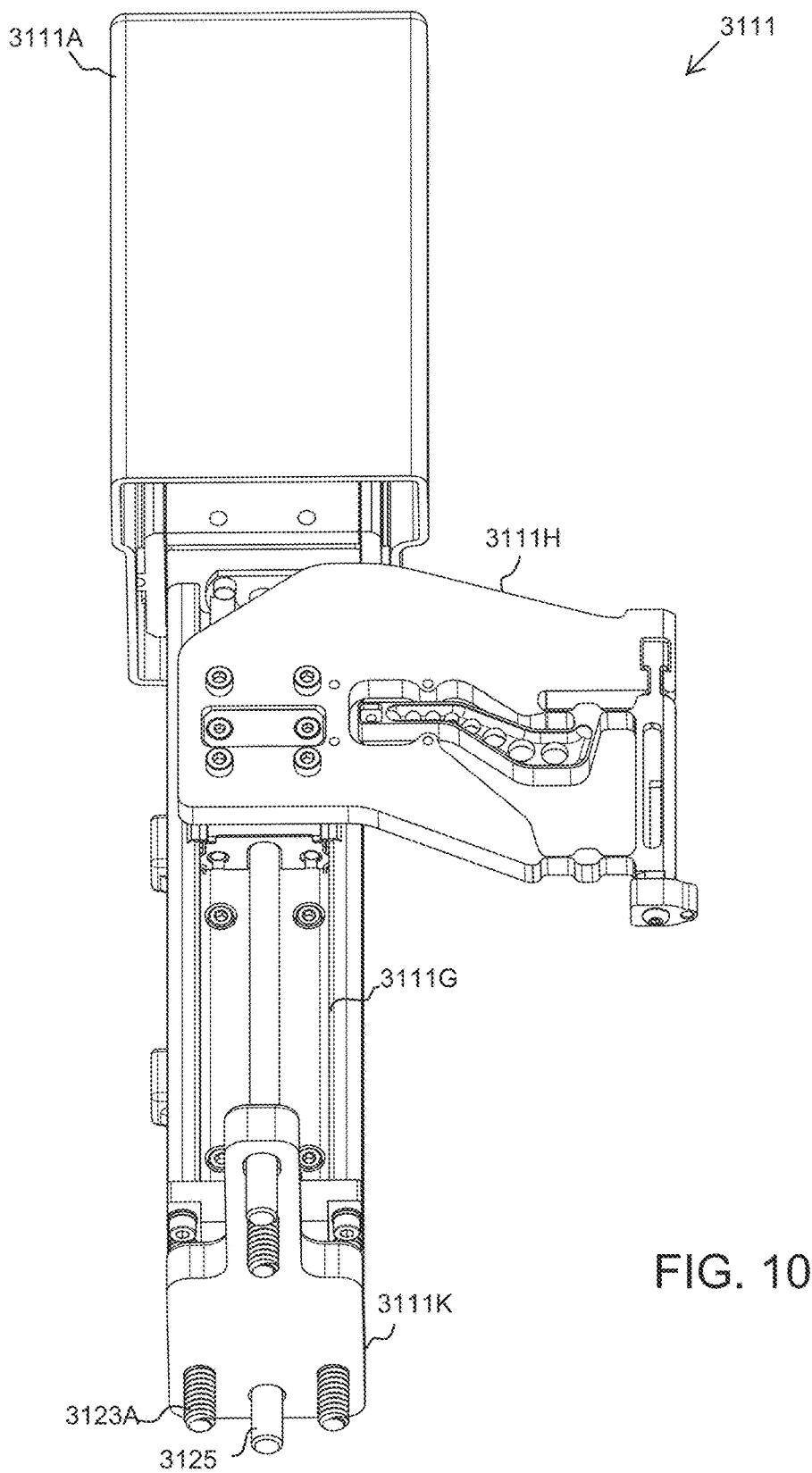

Referring now to FIGS. 9 and 10, at least one pressure actuator assembly 3111 can enable applying pressure to device 3109 (FIG. 5B) by controlling pin actuator 3113 (FIG. 8C) according to dynamic pressurizing instructions, and can monitor the results of the pressuring by sensing forces and/or linear displacement encountered during the pressurizing. At least one pressure actuator assembly 3111 can include controller housing 3111A than can house and protect controller printed circuit board 3111D (FIG. 15) and motor 3111C (FIG. 20) (within motor housing 3111B (FIG. 14)). Pressure actuator assembly 3111 can include actuator arm 3111H that can couple electronic and mechanical movement means to move and position pin actuator 3113 (FIG. 8C). Pressure actuator assembly 3111 can include linear actuator 3111G that can force actuator arm 3111H into a position appropriate for forcing device 3109 (FIG. 5B) or another type of device, as directed by controller 3111D1 (FIG. 15), and actuator mount 3111K that can couple linear actuator with controller housing 3111A. Actuator mount 3111K can include fastening cavities that can couple actuator mount 3111K with platform 3101 (FIG. 4) at actuator mounting cavities 3101D/F/G/H (FIG. 4) using, for example, fasteners 3123A and/or alignment peg 3125.

Figure 11:
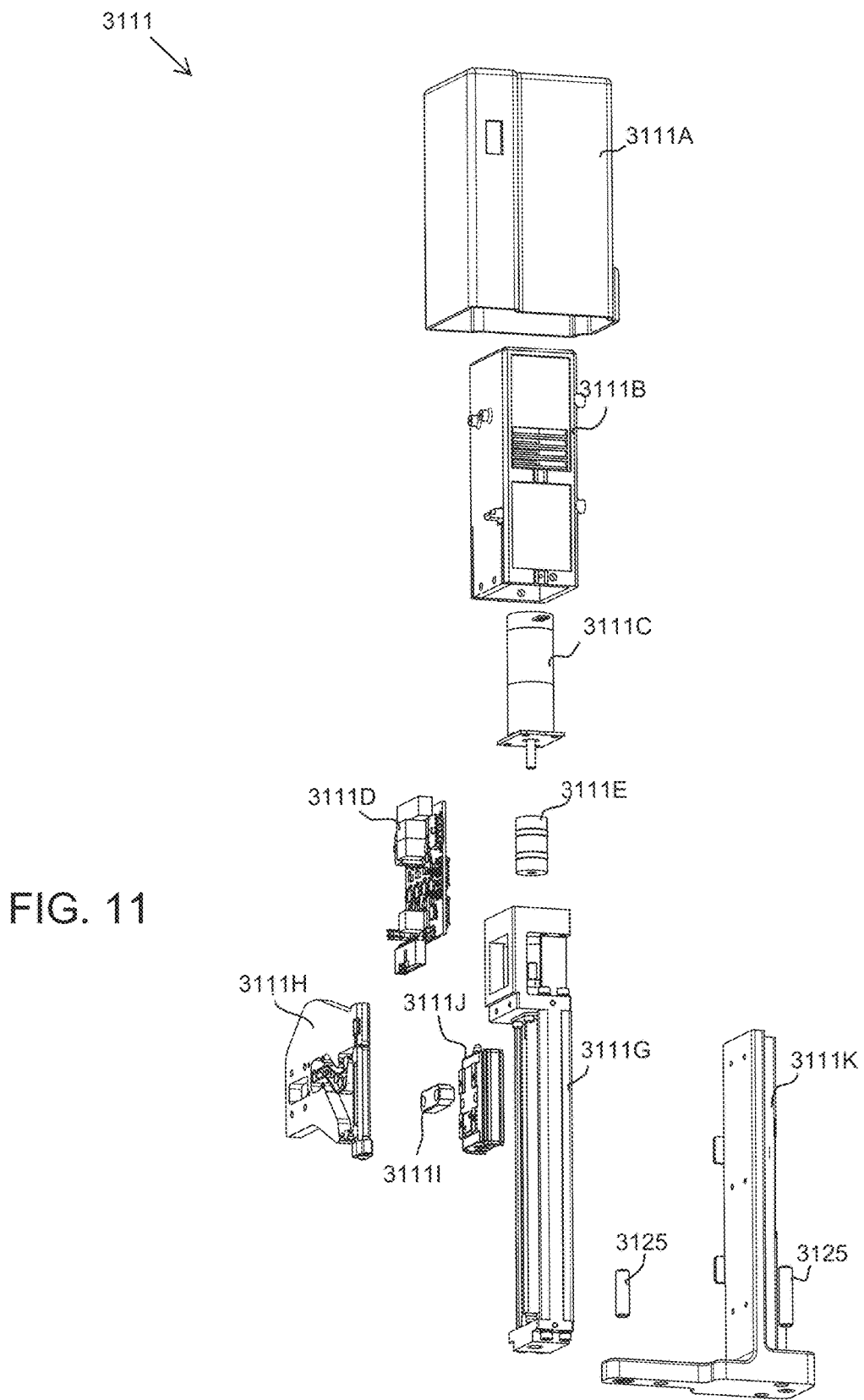
FIG. 11 is a schematic diagram of an exploded view of the pressure actuator assembly of the present teachings.
Figure 20:
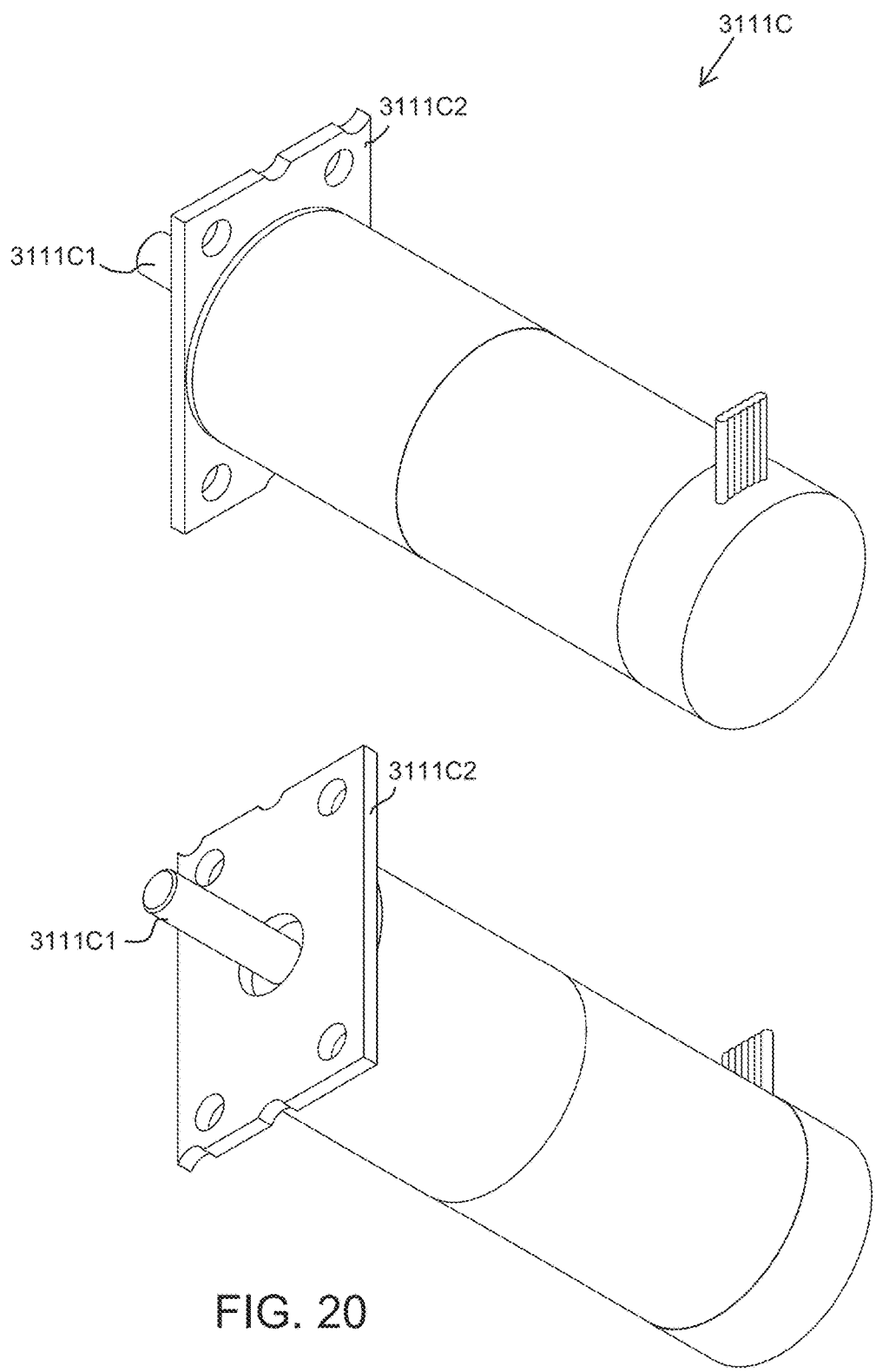
FIG. 20 is a schematic diagram of first and second views of the motor of the present teachings.
Figure 21:
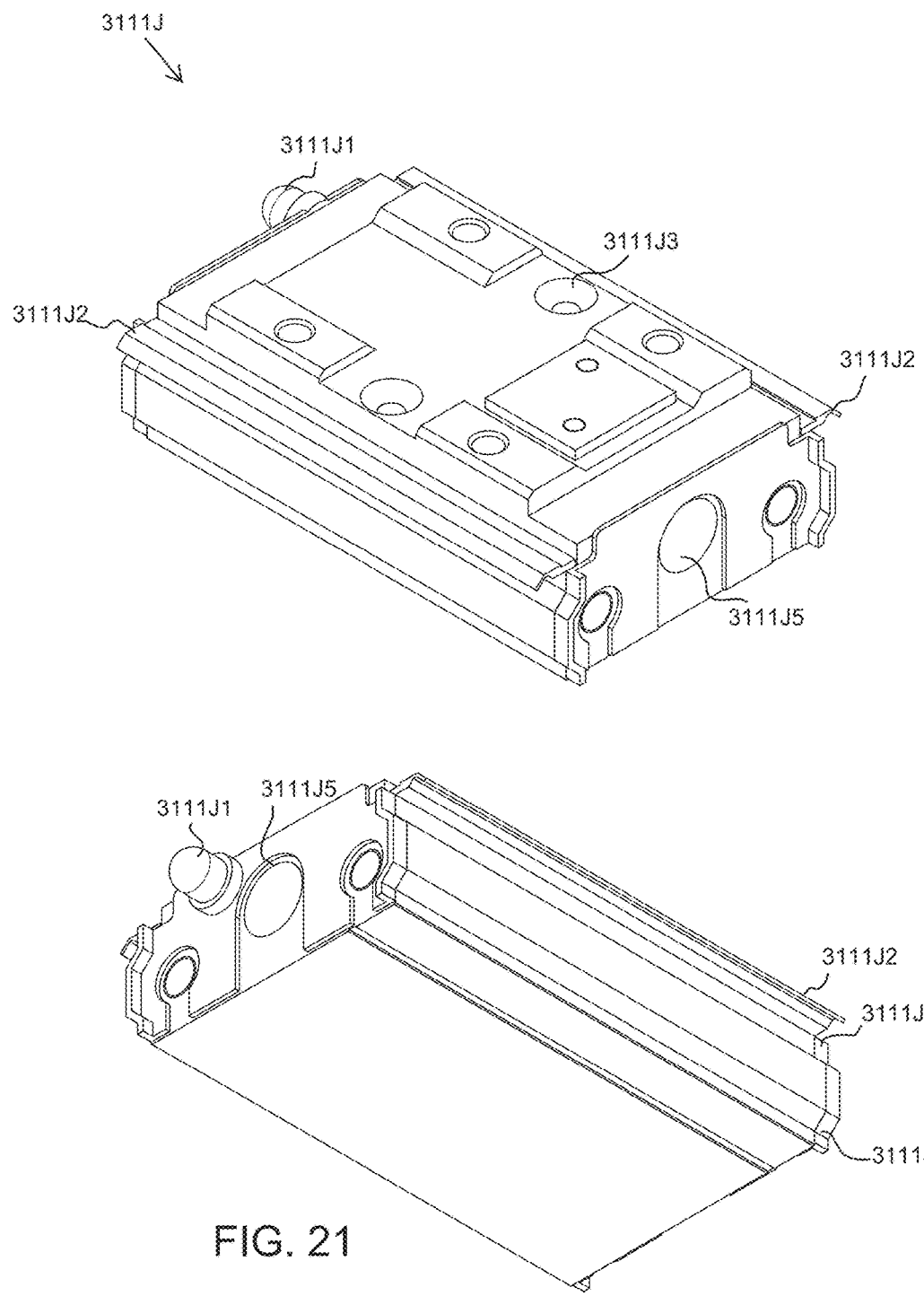
FIG. 21 is a schematic diagram of first and second views of the slide block of the present teachings.
Figure 22:
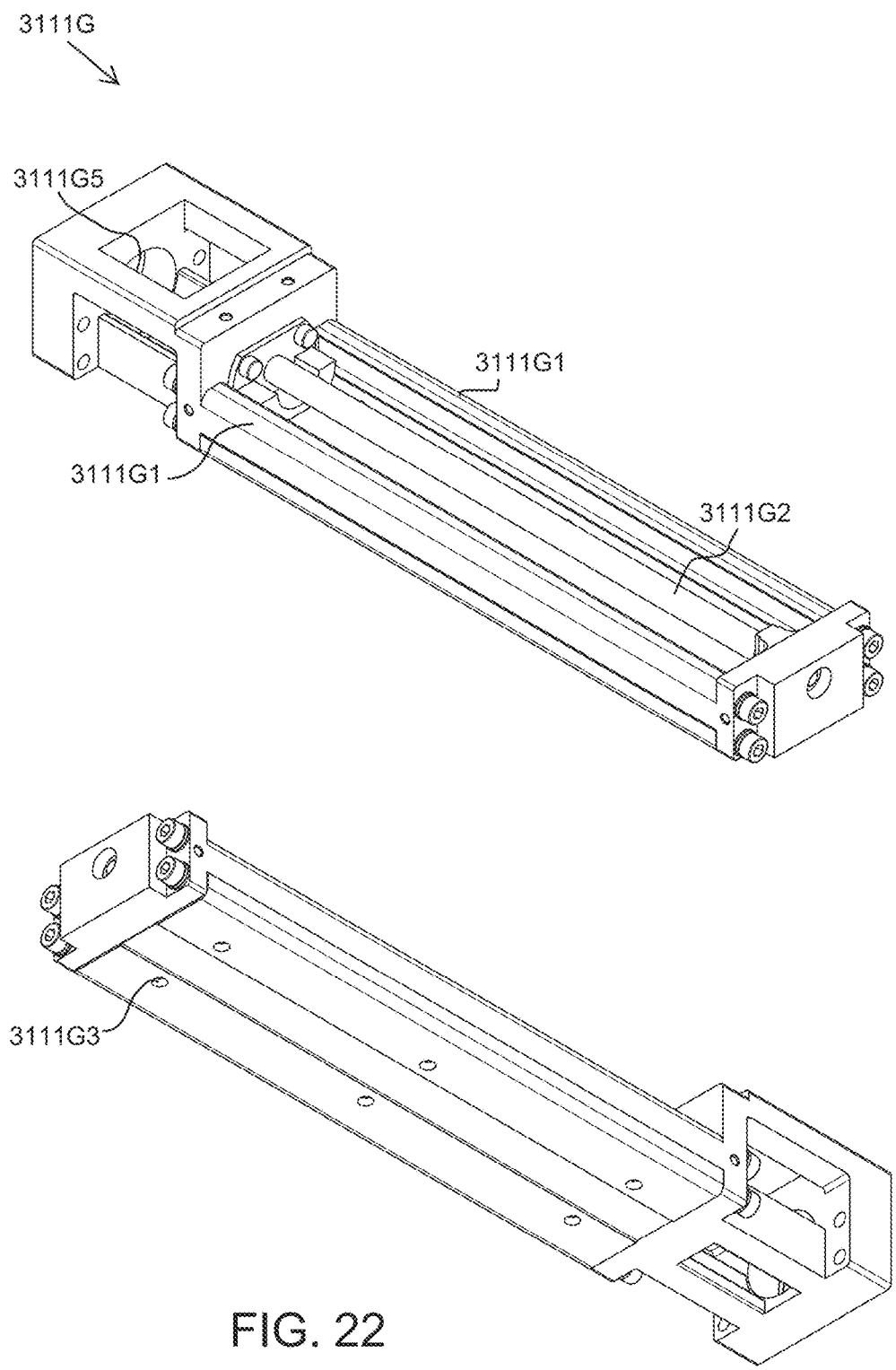
FIG. 22 is a schematic diagram of first and second views of the linear actuator of the present teachings.

Referring now to FIG. 11, pressure actuator assembly 3111 can include motor/PCB housing 3111B (FIG. 14), motor 3111C (FIG. 20), controller PCB 3111D (FIG. 15), and encoder PCB (not shown). Motor interface 3111E (FIG. 23) can couple motor 3111C (FIG. 20) to linear actuator 3111G (FIG. 22). Linear actuator 3111G (FIG. 22) can be operably coupled with slide block 3111J (FIG. 21). Arm adapter 3111I can operably couple actuator arm 3111H (FIG. 19) with slide block 3111J (FIG. 21).

Figure 12:
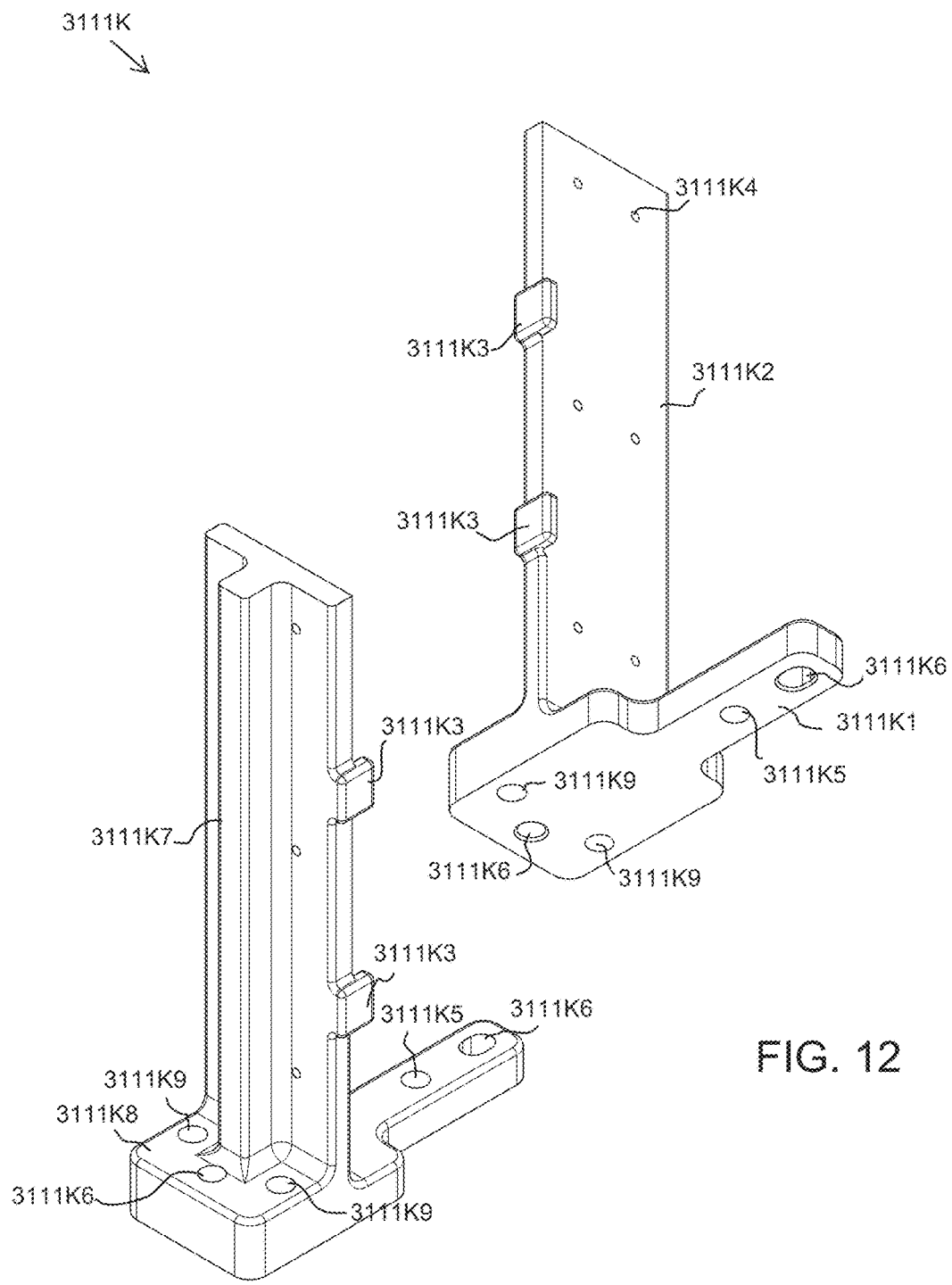
FIG. 12 is a schematic diagram of first and second views of the actuator mount of the present teachings.

Referring now to FIG. 12, actuator mount 3111K can include, but is not limited to including, mount first side 3111K2 and mounting face 3111K1. Mount first side 3111K2 can include at least one linear actuator mounting cavity 3111K4 that can be used to fasten linear actuator 3111G (FIG. 22) to actuator mount 3111K. Linear actuator mounting features 3111K3 can enable accurate and stable placement of linear actuator 3111G (FIG. 22). Actuator mount 3111K can include at least one stability feature 3111K7 that can enable actuator mount 3111K to rigidly support linear actuator 3111G (FIG. 22). Actuator mount 3111K can be aligned and stably positioned on platform 3101 (FIG. 4) by alignment pegs 3125 (FIG. 5A) in peg cavities 3111K6. Actuator mount 3111K can be securely fastened to platform 3101 (FIG. 4) by any attachment means such as, for example, but not limited to, glue, screws, bolts, and/or hook-and-eye. In some configurations, the attachment means can be screws and/or bolts through cavities 3111K5/3111K9.

Figure 13:
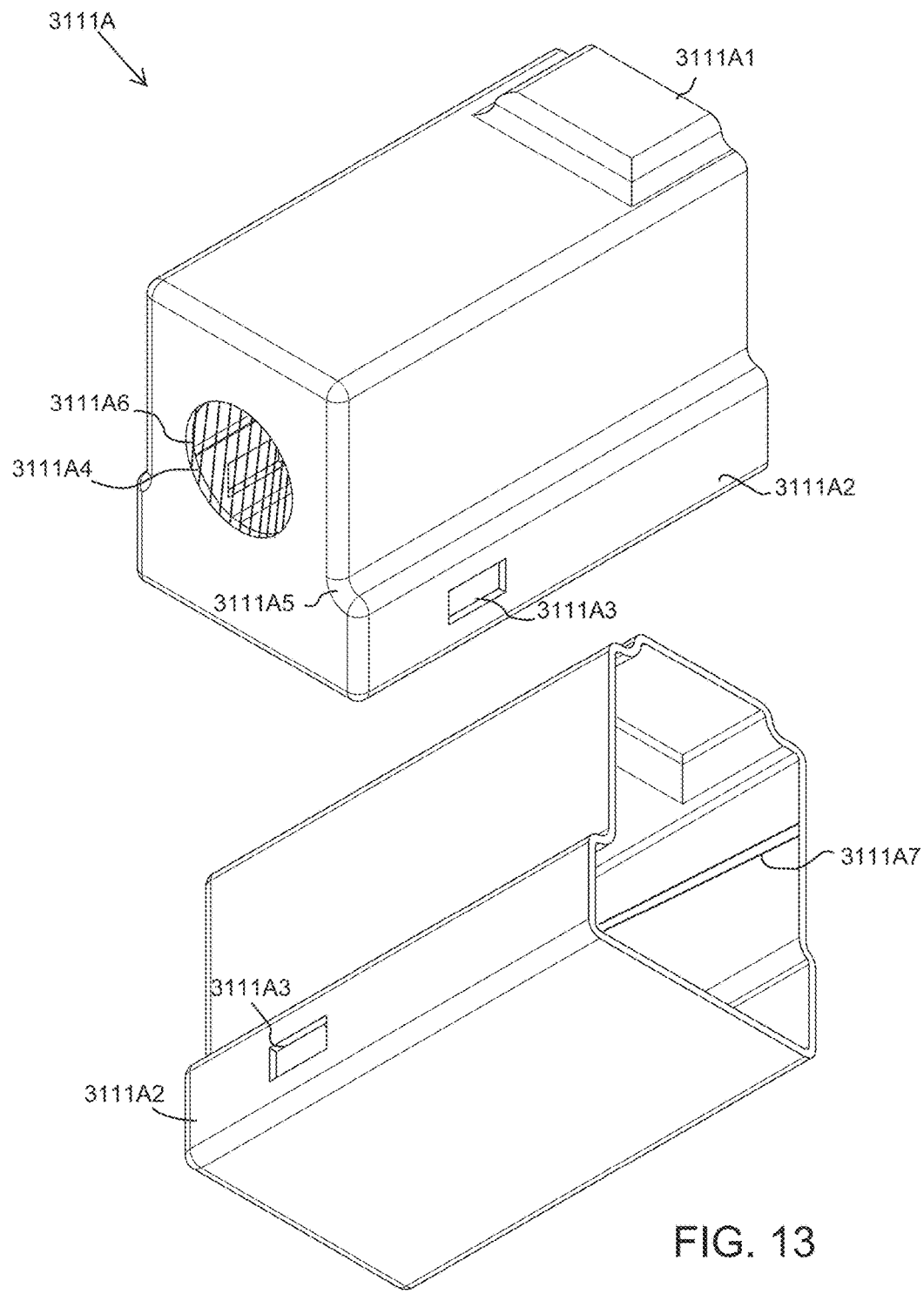
FIG. 13 is a schematic diagram of first and second views of the motor/PCB housing cover of the present teachings.

Referring now to FIG. 13, motor/PCB housing cover 3111A can include connector bump out 3111A1 that can provide a space for connectors and wiring between motor 3111C (FIG. 20) and encoder PCB (not shown). Motor/PCB housing cover 3111A can include CANbus cavity 3111A3 that can enable CANbus/power wiring to pass between CAN/power connectors 3111D2 (FIG. 15) and external communications/power supply (not shown). Motor vent cavity 3111A4, that can include, but is not limited to including, louvers 3111A6, can enable ventilation to motor 3111C (FIG. 20). Bump out 3111A2 can widen motor/PCB housing cover 3111A to accommodate the geography of controller PCB 3111D (FIG. 15). Filet edge 3111A5 can streamline the profile of motor/PCB housing cover 3111A to manage overall weight and maintain strength and stability of force actuation system 3100 (FIG. 1). Ridge feature 3111A7 can accommodate alignment while inserting/removing motor/PCB housing 3111B (FIG. 14).

Figure 14:
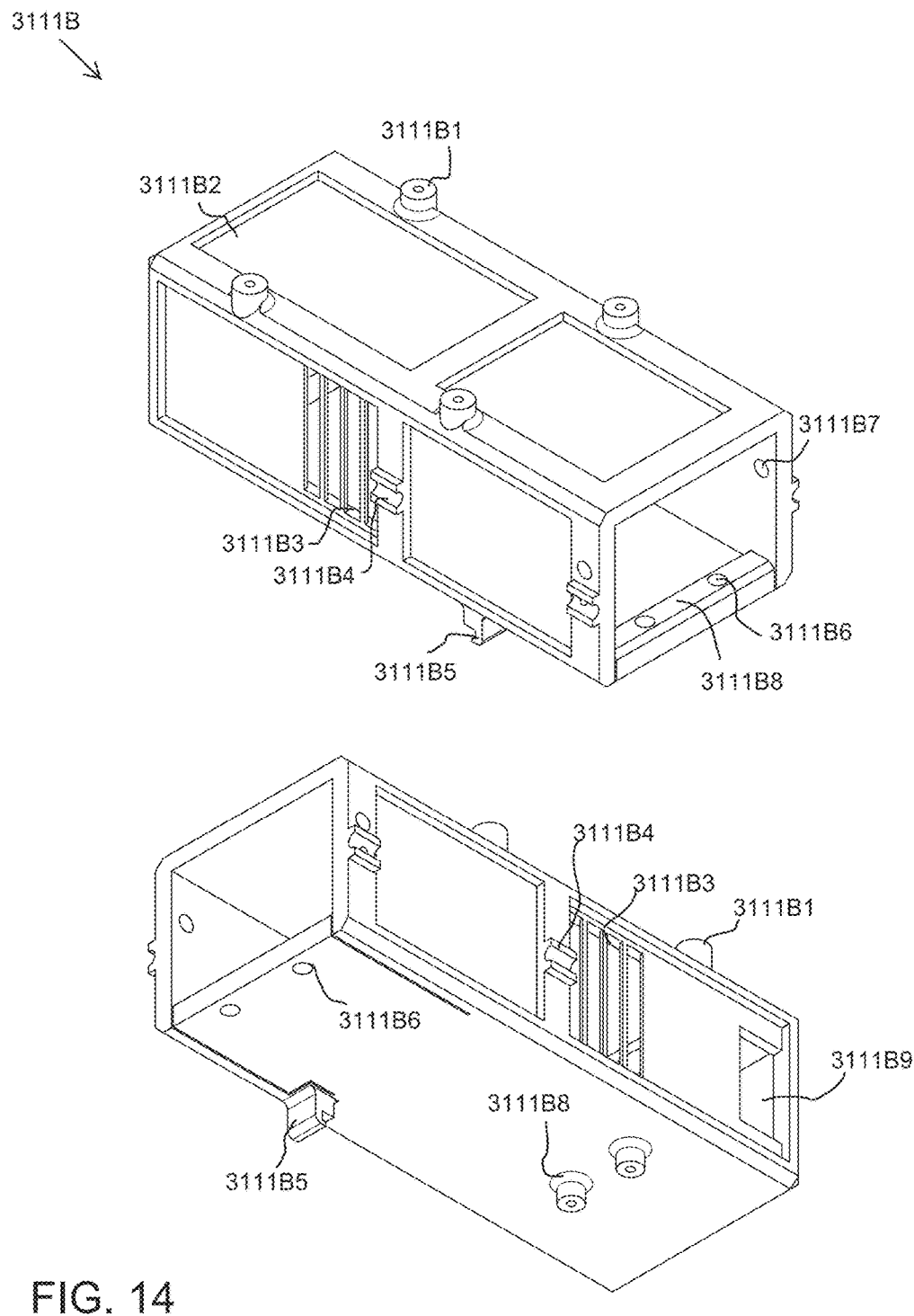
FIG. 14 is a schematic diagram of first and second views of the motor/PCB housing of the present teachings.
Figure 15:
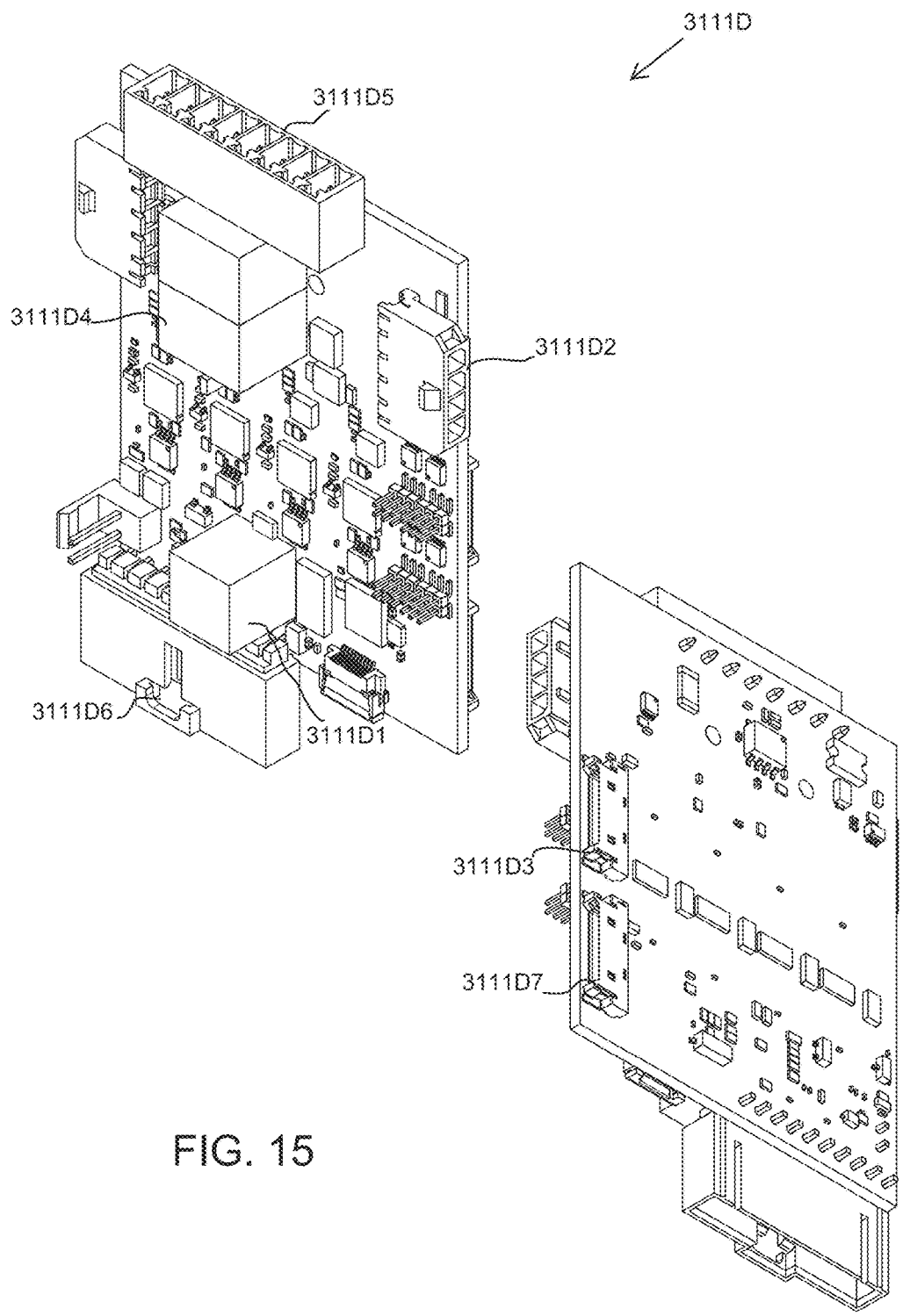
FIG. 15 is a schematic diagram of first and second views of the controller PCB of the present teachings.

Referring now to FIG. 14, motor/PCB housing 3111B can include at least one mounting feature 3111B1 that can enable mounting of encoder PCB (not shown). Housing 3111B can include at least one indent 3111B2 that can enable air flow around encoder PCB (not shown), and can manage overall weight. Motor 3111C (FIG. 20) can be vented through motor vents 3111B3, and snap-on features 3111B4 can enable secure mounting of housing 3111B within cover 3111A (FIG. 13). Motor coupling 3111E (FIG. 23) can snap into alignment across bridge 3111B8 and can be securely attached with fastening means through, for example, cavities 3111B6/3111B7. Fastening means can include, but are not limited to including, screws, bolts, glue, and hook-and-eye. Controller PCB 3111D (FIG. 15) can be mounted to housing 3111B at controller mounting points 3111B8, and can rest upon lip 3111B5. Motor 3111C (FIG. 20) and motor coupling 3111E (FIG. 23) can be housed within housing 3111B.

Referring now to FIG. 15, controller printed circuit board (PCB) 3111D can provide commands to control force actuation system 3100 (FIG. 1) and can receive sensor input that can inform the commands. Controller PCB 3111D can include, but is not limited to including, CPU 3111D1, at least one capacitor 3111D4, and several connectors to off-board devices. For example, controller PCB 3111D can include CAN/power connectors 3111D2 that can connect controller PCB 3111D to power and external communications devices. Controller PCB 3111D can include quad encoder power connector 3111D6 that can enable power for the encoder PCB (not shown) for motor 3111C (FIG. 20) and controller PCB 3111D. Controller PCB 3111D can include Hall sensor connector 3111D7 that can enable signal exchange between Hall sensor PCB (not shown) mounted on actuator arm 3111H (FIG. 19) and controller PCB 3111D, and quad encoder PCB connector 3111D3 that can enable signal exchange between quad encoder (not shown) and controller PCB 3111D. Any configuration of Hall sensor connector 3111D7 and quad encoder PCB connector 3111D3 is possible. Controller PCB 3111D can include motor connectors 3111D5 that can enable signal exchange between motor 3111C (FIG. 20) and controller PCB 3111D.

Figure 16:
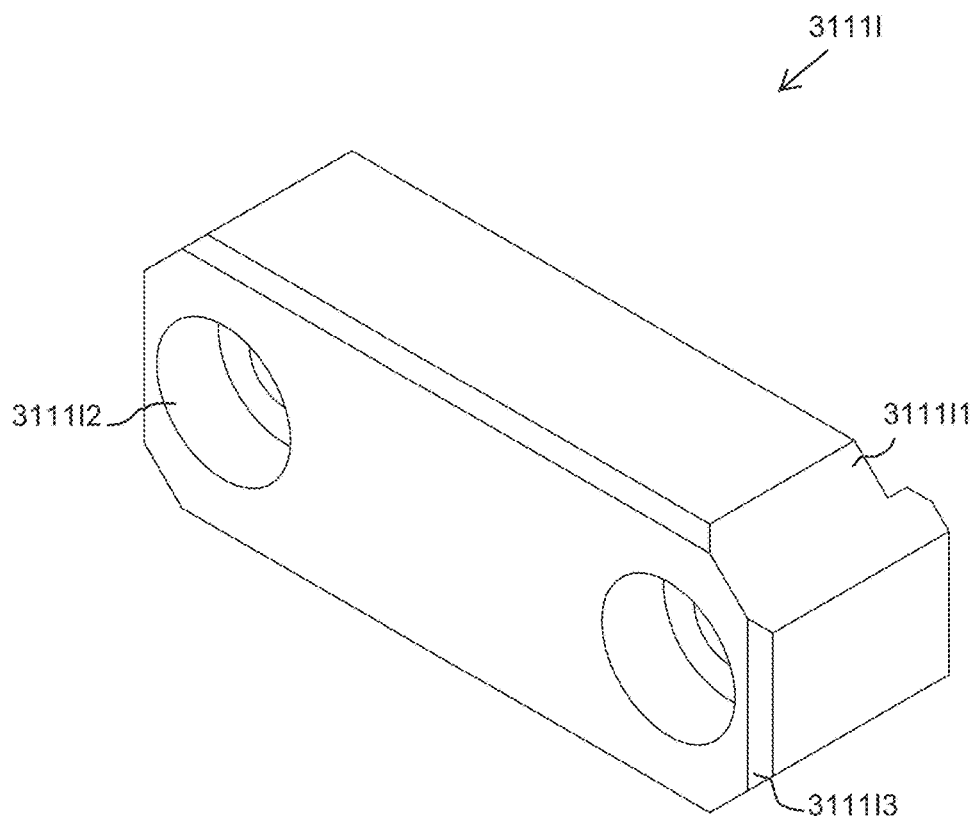
FIG. 16 is a schematic diagram of first and second views of the arm adapter of the present teachings.
Figure 16:
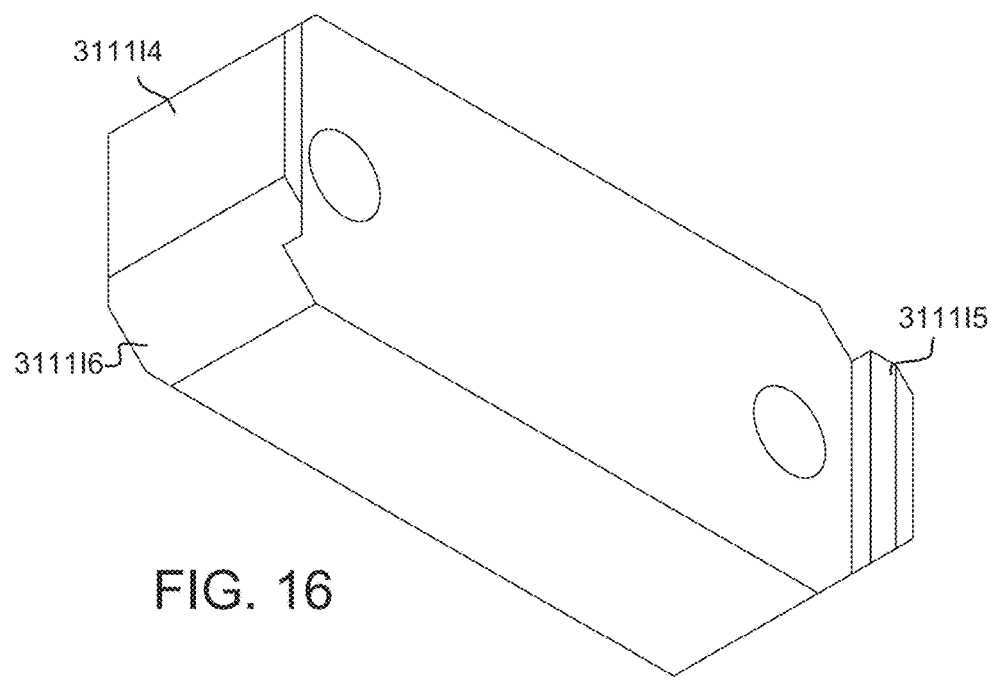

Referring now to FIG. 16, arm adapter 3111I can enable alignment between linear actuator 3111G (FIG. 22) and actuator arm 3111H (FIG. 19). Arm adapter 3111I can include, but is not limited to including, at least one mounting cavity 3111I2 that can accept fastening means such as, for example, but not limited to, screws and/or bolts that can attach arm adapter 3111I to slide block 3111J (FIG. 21). Arm adapter 3111I can include vertical and horizontal alignment features 3111I1/3111I3/3111I4/3111I5/3111I6, and can be sized to fit in arm cavity 3111H2 (FIG. 19) in actuator arm 3111H (FIG. 19), enabling stable alignment between linear actuator 3111G (FIG. 22) and actuator arm 3111H (FIG. 19).

Figure 17:
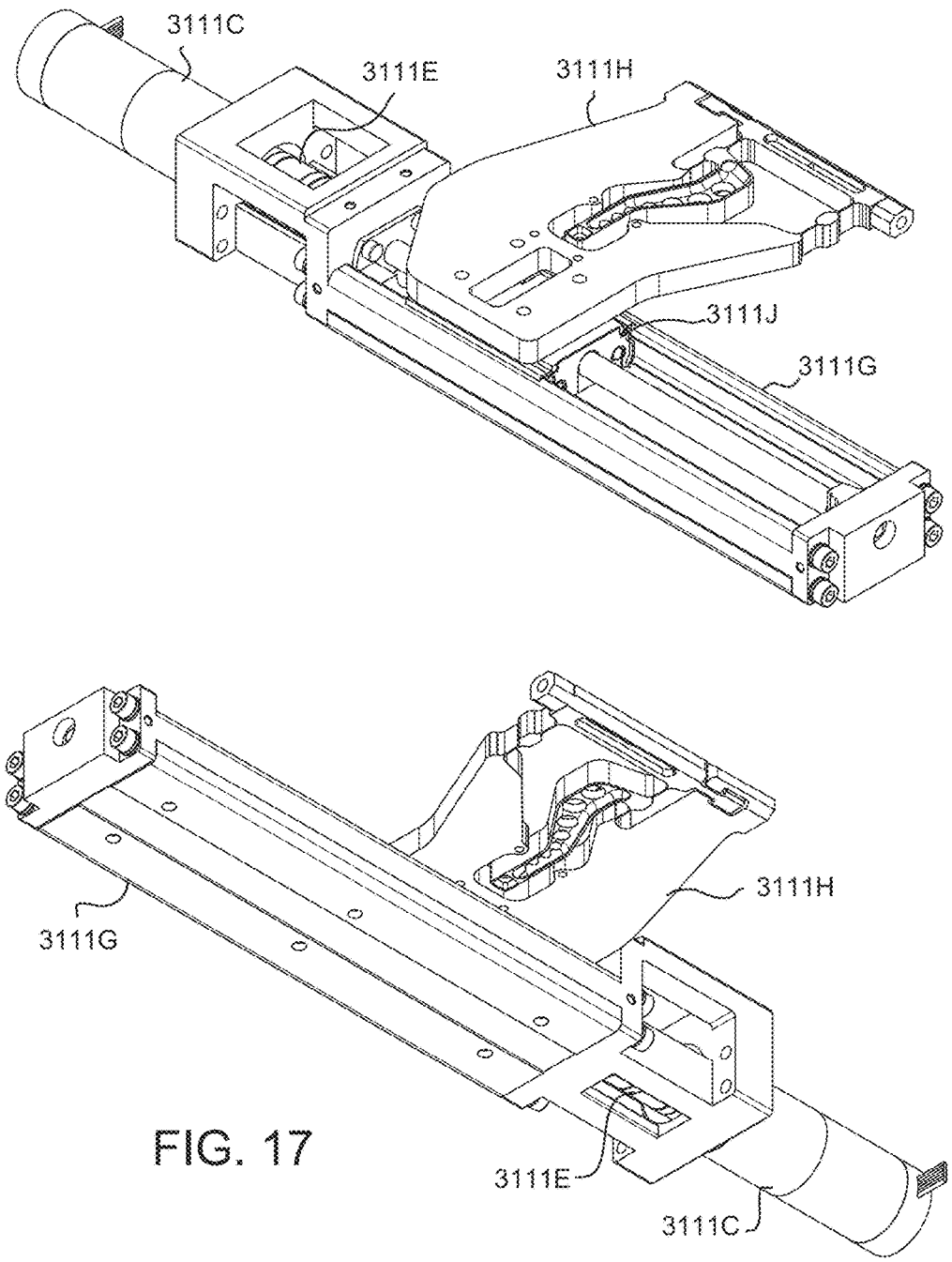
FIG. 17 is a schematic diagram of first and second views of the linear actuator/actuator arm assembly of the present teachings.
Figure 18:
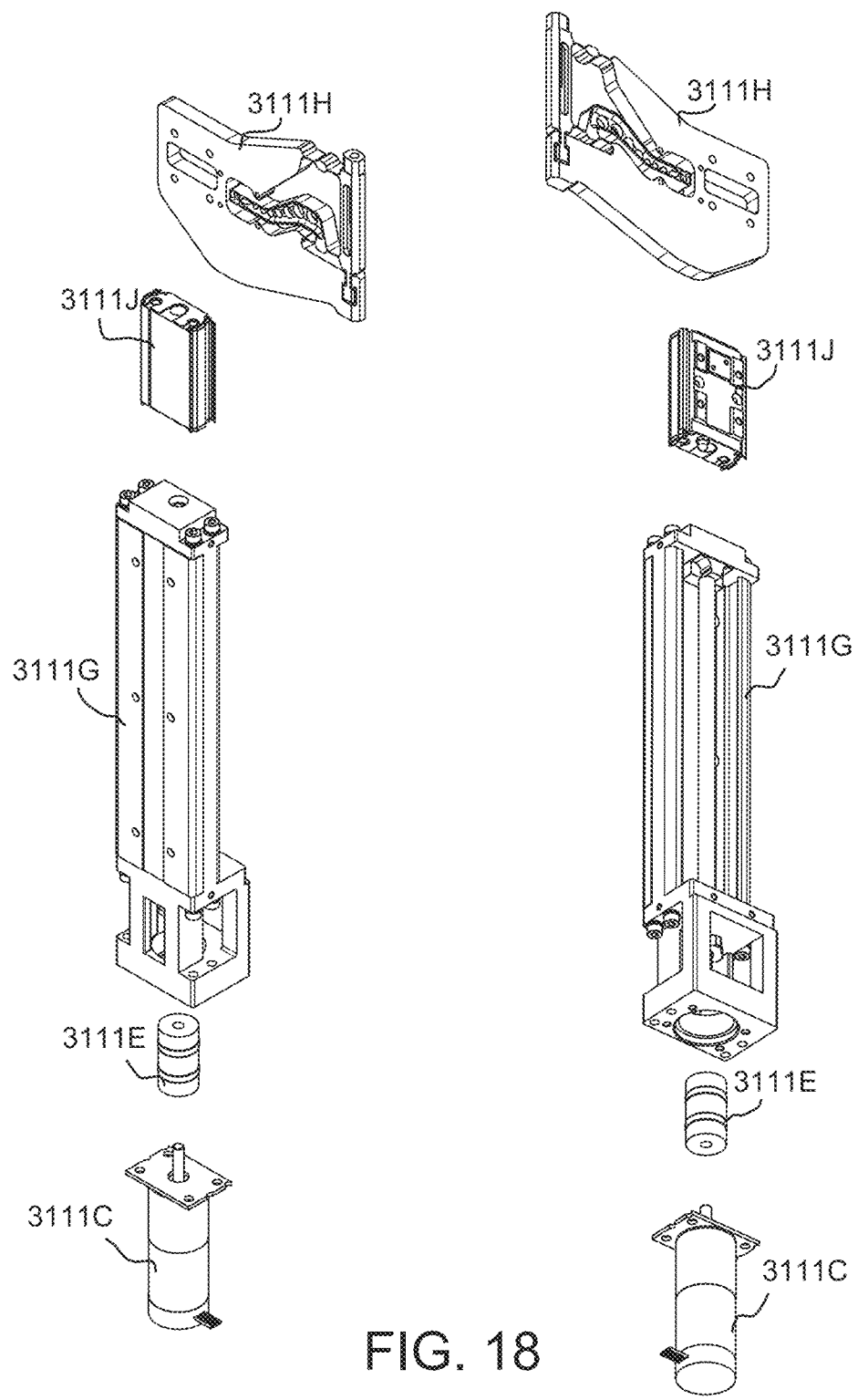
FIG. 18 is a schematic diagram of an exploded view of the linear actuator/actuator arm assembly of the present teachings.

Referring now to FIGS. 17 and 18, linear actuator/actuator arm assembly can include, but is not limited to including, actuator arm 3111H that can be connected to slide block 3111J. Slide block 3111J can be operably coupled with linear actuator 3111G. Linear actuator/actuator arm assembly can be driven by motor 3111C that can be operably coupled with linear actuator 3111G through motor coupling 3111E.

Referring now to FIG. 19, after actuator arm 3111H encounters device 3109 (FIG. 5B), actuator arm 3111H can receive a constant force from pin actuator 3113 (FIG. 8C) that can receive the force from device 3109 (FIG. 5B). Actuator arm 3111H can be displaced based on the force supplied by device 3109 (FIG. 5B), and the displacement can determine the amount of force received. Actuator arm 3111H can include, but is not limited to, pivot member 3111H3 that can change position with the change in force and can return to a neutral position through action of springs 3111H15. Displacement of force member 3111H4 can be determined by gaps 3111H13/3111H14 that can be formed by the movement of displacement block 3111H9. Displacement block 3111H9 can include a hard stop after a certain amount of displacement/force. Actuator arm 3111H can include mounting member 3111H11 that can be operably coupled with end effector offset (FIG. 8A) in cavity 3110B (FIG. 8A), and can enable mounting of fluid shutoff actuator 3121 (FIG. 8D) at peg fitting 3121A (FIG. 8D). In some configurations, cavity 3111H12 can accommodate a fastener such as a screw or bolt. A sensor that can detect displacement of pivot member 3111H3 can be mounted at cavity 3111H14, and electronics to receive data from the sensor can be mounted at mounting cavities 3111H1. Cavities 3111H5/3111H8, as well as shaped edged 3111H7, can enable overall weight and part placement management. A Hall sensor magnet (not shown) can be mounted at, for example, fastener cavities 3111H1, with possible associated Hall sensor PCB at cavity 3111H2 mounted at fastener cavities 3111H6.

Referring now to FIG. 20, motor 3111C can include, but is not limited to including, a DC motor, brushless or brushed, having, for example, an ironless rotor and aluminum nickel cobalt magnets. Motor 3111C can include, for example, MAXON® A-max motors.

Referring now to FIG. 21, slide block 3111J can include at least one fastener cavity 3111J3 that can accommodate mounting of arm adapter 3111I (FIG. 16) onto slide block 3111J. Slide block guides 3111J4 and slide block rail fittings 3111J4/3111J5 can ride on actuator rails 3111G1 (FIG. 22), and actuator bumper 3111J1 can inhibit progress of slide block 3111J when bumper 3111J1 encounters an obstacle. Slide block 3111J can accommodate lead or ball/lead screw 3111G2 (FIG. 22) in cavity 3111J5.

Figure 23:
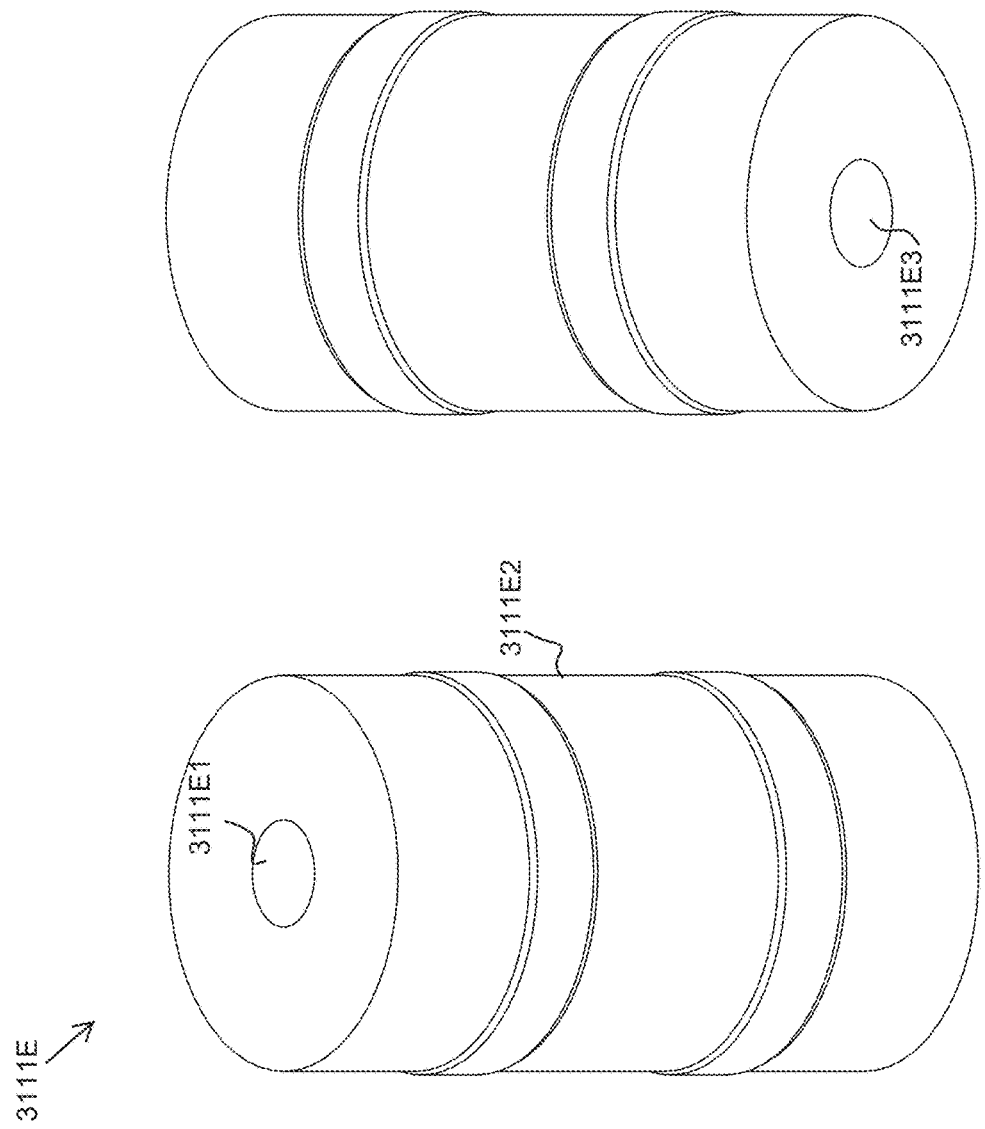
FIG. 23 is a schematic diagram of first and second views of the motor coupling of the present teachings.

Referring now to FIG. 22, linear actuator 3111G can include motor cavity 3111G5 that can accommodate motor coupling 3111E (FIG. 23). Motor 3111C (FIG. 20) can drive ball/lead screw 3111G2 and thus propel slide block 3111J (FIG. 21), actuator arm 3111H (FIG. 19), and ultimately pin actuator 3113 (FIG. 8C). Linear actuator can include rails 3111G1 upon which slide block 3111J (FIG. 21) can ride. Linear actuator can include mounting cavities 3111G3 that can enable operable coupling of linear actuator 3111G to actuator mount 3111K (FIG. 12).

Referring now to FIG. 23, motor coupling 3111E can operably couple linear actuator 3111G (FIG. 22) with motor 3111C (FIG. 20) to transmit power between them. Motor coupling 3111E can include a clamping mechanism such as, for example, but not limited to, bellows and/or beam. Motor coupling 3111E can include commercially-available devices such as, for example, but not limited to, LOVEJOY® couplings. Motor coupling 3111E can optionally include a clutch that can limit torque. Motor coupling 3111E can also include flexible and jaw couplings. Motor coupling 3111E can optionally compensate for lateral, axial, and angular misalignments. Motor couplings 3111E can optionally include no backlash and require no maintenance. Motor coupling 3111E can include, but is not limited to including, body 3111E2 that can, for example, include a cylindrical shape. Motor coupling 3111E can include motor mount cavity 3111E1 and linear actuator mount cavity 3111E3.

Figure 24:
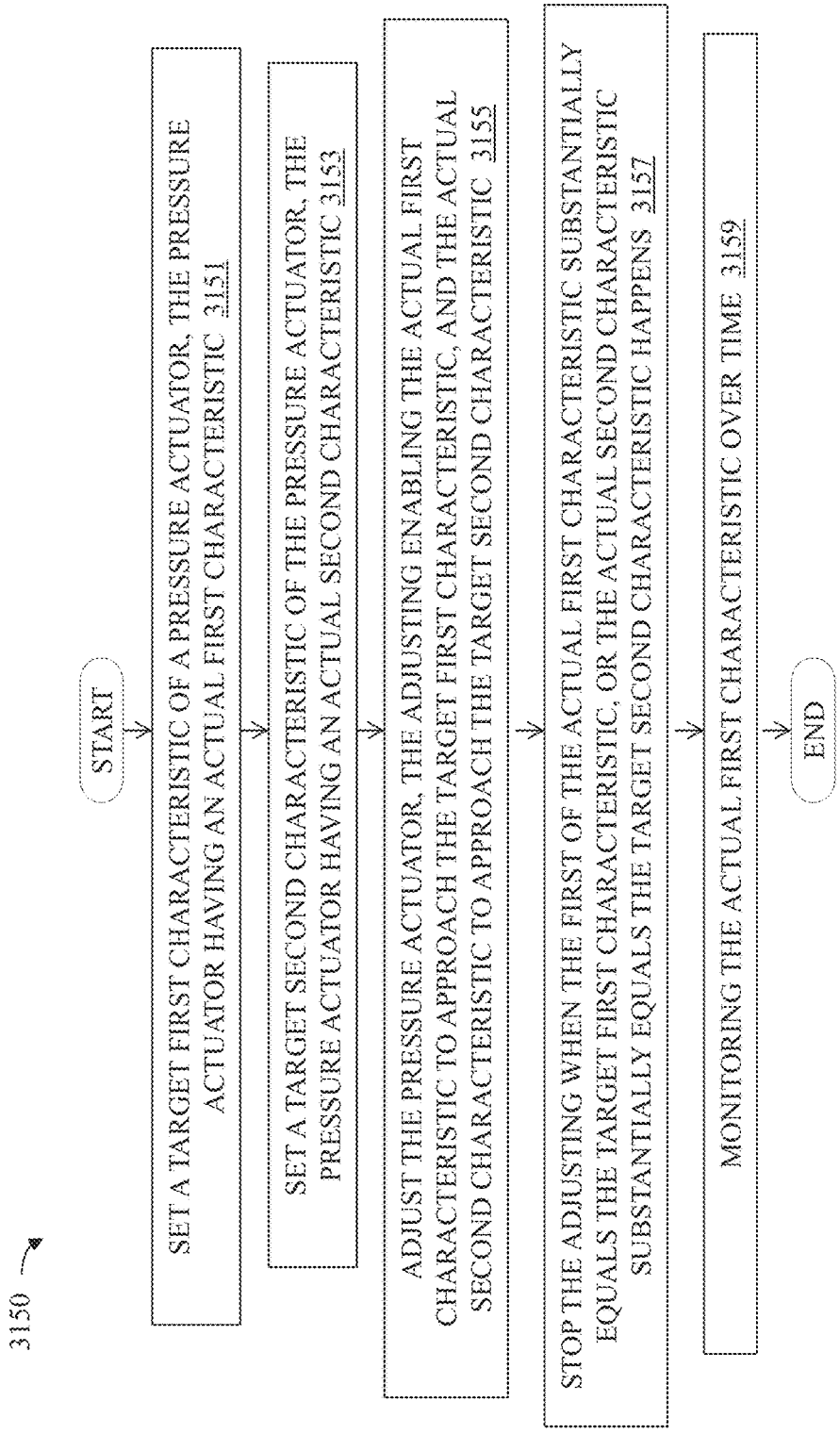
FIG. 24 is a flowchart of the method for applying force of the present teachings.

Referring now primarily to FIG. 24, method 3150 for activating/applying force to a device can include, but is not limited to including, setting 3151 a target first characteristic of a pressure actuator, the pressure actuator having an actual first characteristic, setting 3153 a target second characteristic of the pressure actuator, the pressure actuator having an actual second characteristic, and adjusting 3155 the pressure actuator, the adjusting enabling the actual first characteristic to approach the target first characteristic, and the actual second characteristic to approach the target second characteristic. Method 3150 can include stopping 3157 the adjusting when the first of the actual first characteristic substantially equals the target first characteristic, or the actual second characteristic substantially equals the target second characteristic happens, and monitoring 3161 the actual first characteristic over time. In some configurations, a test can be executed in which the force can be held constant by modifying the position of actuator arm 3111H (FIG. 19).

Figure 25:
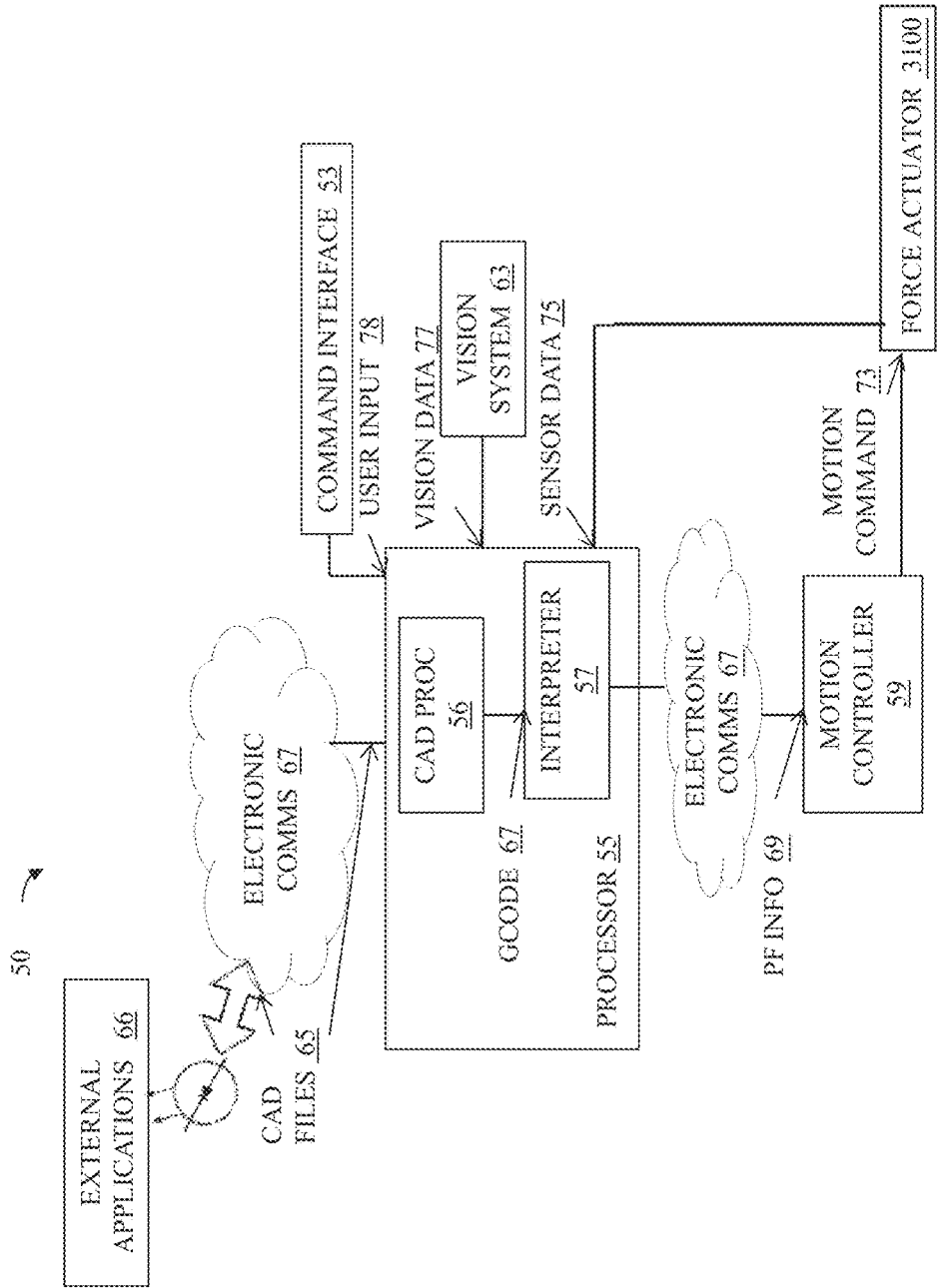
FIG. 25 is a schematic block diagram of the force activation system of the present teachings.

Referring now to FIG. 25, force actuator system 50 can include, but is not limited to including, force actuator 3100, processor 55, receiving computer aided design (CAD) files 65 and other information through, for example, but not limited to, electronic communications from external applications 66, and motion controller 59. Processor 55 can provide commands to motion controller 59 that can test the structures designed and provided in CAD files 65. Processor 55 can also receive, for example, vision data 77 from vision system 63, hardware/sensor data 75, and user input 78, and can calculate Gcode 67 based at least on a combination of one or more of CAD files 65, vision data 77, user input 78, hardware data 75, and other information. Interpreter 57 can interpret Gcode 67 and provide position and force (PF) information 69 to motion controller 59. Motion controller 59 can compute at least one motion command 73 based at least on PF information 69, and can provide at least one motion command 73 to force actuator 3100. Force actuator 3100 can control at least one pin actuator 3113 (FIG. 8C) based on at least one motion command 73.

Continuing to refer to FIG. 25, command interface 53 can enable user input 78 that can be used to manually command and/or to assist in automatically commanding force actuator 3100. Command interface 53 can include, but is not limited to including, options for adjusting the type of motion controller 59, the available electronic communications 67, and whether or not electronic communications 67 with external applications 66 is connected. Options can be adjusted through command interface 53. The values of the axes controlled by motion controller 59 can be shown and jogged using command interface 53. The jog function can enable free movement of force actuator 3100 to accommodate maintenance and repair of force actuator 3100.

Continuing to refer to FIG. 25, interpreter 57 can receive Gcode 67 from CAD processor 56, and can transform Gcode 67 into PF information 69 that can be used by motion controller 59 to create motion commands 73 for force actuator 3100. Interpreter 57 can interface with motion controller 59 through any kind of electronic communications 67 including, but not limited to, direct wiring, Ethernet, and USB.

Figure 25A:
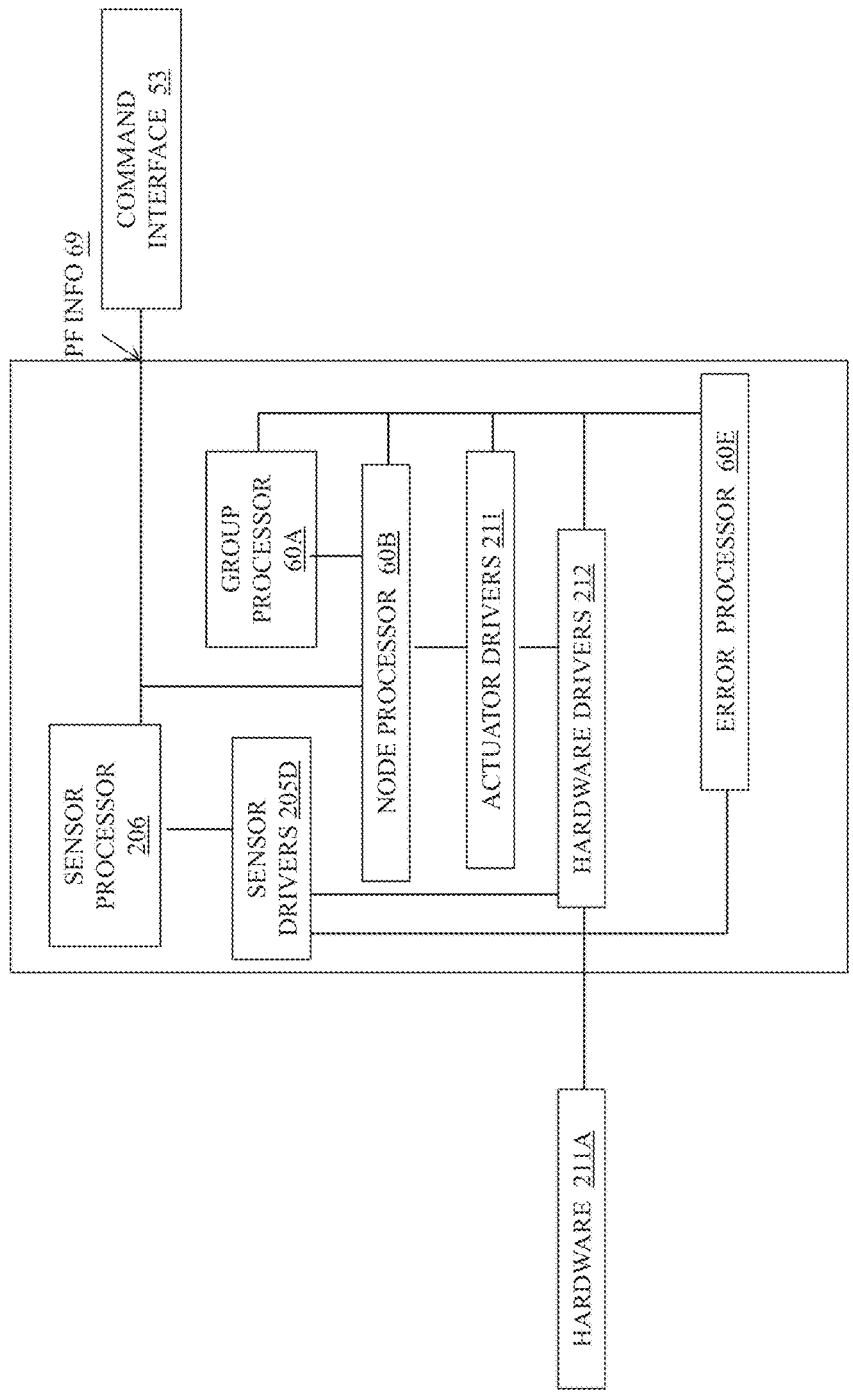
FIG. 25A is a schematic block diagram of the motion controller architecture of the present teachings.

Referring now primarily to FIG. 25A, controller code can control an arbitrary number of actuators such as are incorporated in actuator assembly 3111 (FIG. 9) in any desirable configuration. Each actuator can be controlled, for example, by one or more of several configurable control types, and can be linked to one or more sensors. Configurable control types can include, but are not limited to including, passive pass-through commands, PID control loop, and configurable PID loops for multiple inputs. Motion controller 59 can enable configuration of nested control loops. In some configurations, motion controller 59 can include, but is not limited to including, group processor 60A, node processor 60B, sensor object 205C, sensor drivers 205D, actuator drivers 211, hardware drivers 212, and error processor 60E. Group processor 60A can control, through node processor 60B, nodes to which actuators can be associated. Actuators can be grouped to accomplish coordinated and/or synchronized motion, and can be controlled, by actuator drivers 211, locally and/or remotely through networks that can communicate using, for example, but not limited to, standard CANbus and/or EtherCAT protocols. Actuators can control, for example, rotational and/or linear motion, and can be of various types, for example, but not limited to, binary valves, pneumatic compressors, small block valves (described in, for example, U.S. patent application Ser. No. 14/327,206, entitled Valve Apparatus and System), and heated elements. Sensor object 205C can control sensors that can sense, for example, but not limited to, motor position, linear position, pressure, gyroscopic signals, accelerometer signals, and temperature. Sensors can include primary sensors that can feed into a control loop and secondary sensors that can provide feed forward information. Motion controller 59 can include options for multiple sensor inputs, and sensor limits can be used by motion controller 59 to, for example, raise warnings and/or stop motion. Types of hardware drivers 212 can include, but are not limited to including local drivers, CAN drivers, motor drivers manufactured by, for example, AMC® and/or Maxon®, and sell block (described in, for example, U.S. patent application Ser. No. 14/967,093 entitled Modular Valve Apparatus and System).

Figure 25B:
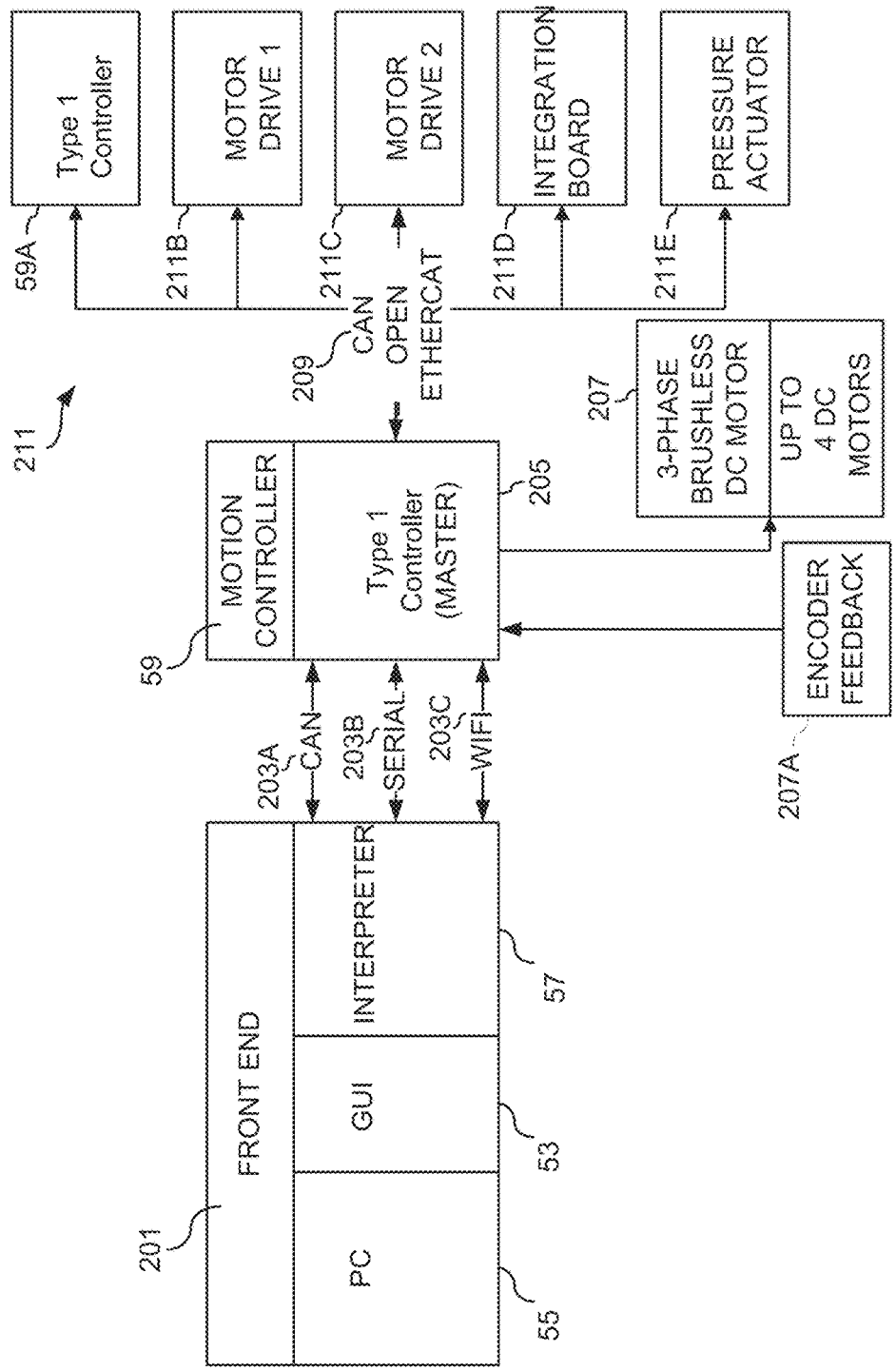
FIG. 25B is a schematic block diagram of a first hardware configuration of the system of the present teachings.
Figures 1, 25B:
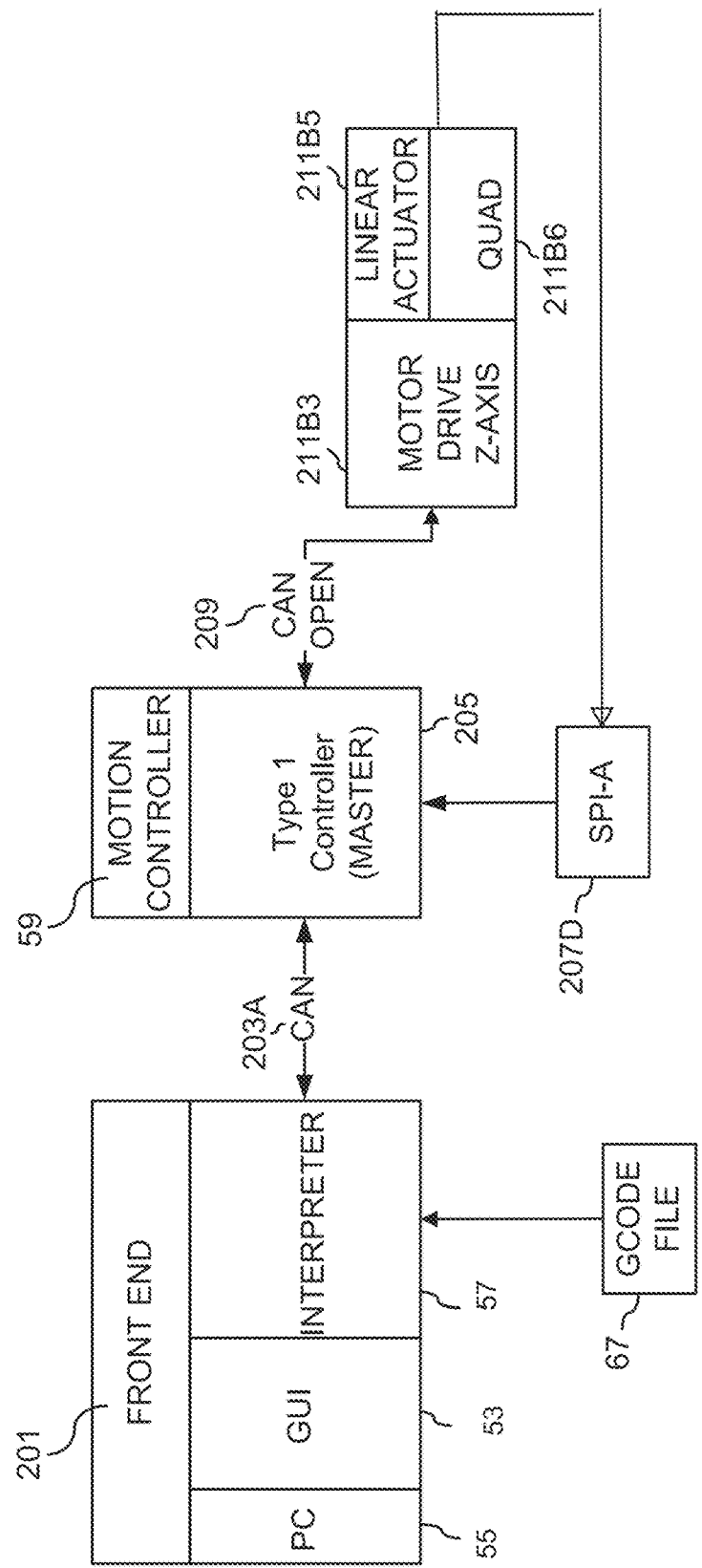
Figures 2, 25B:
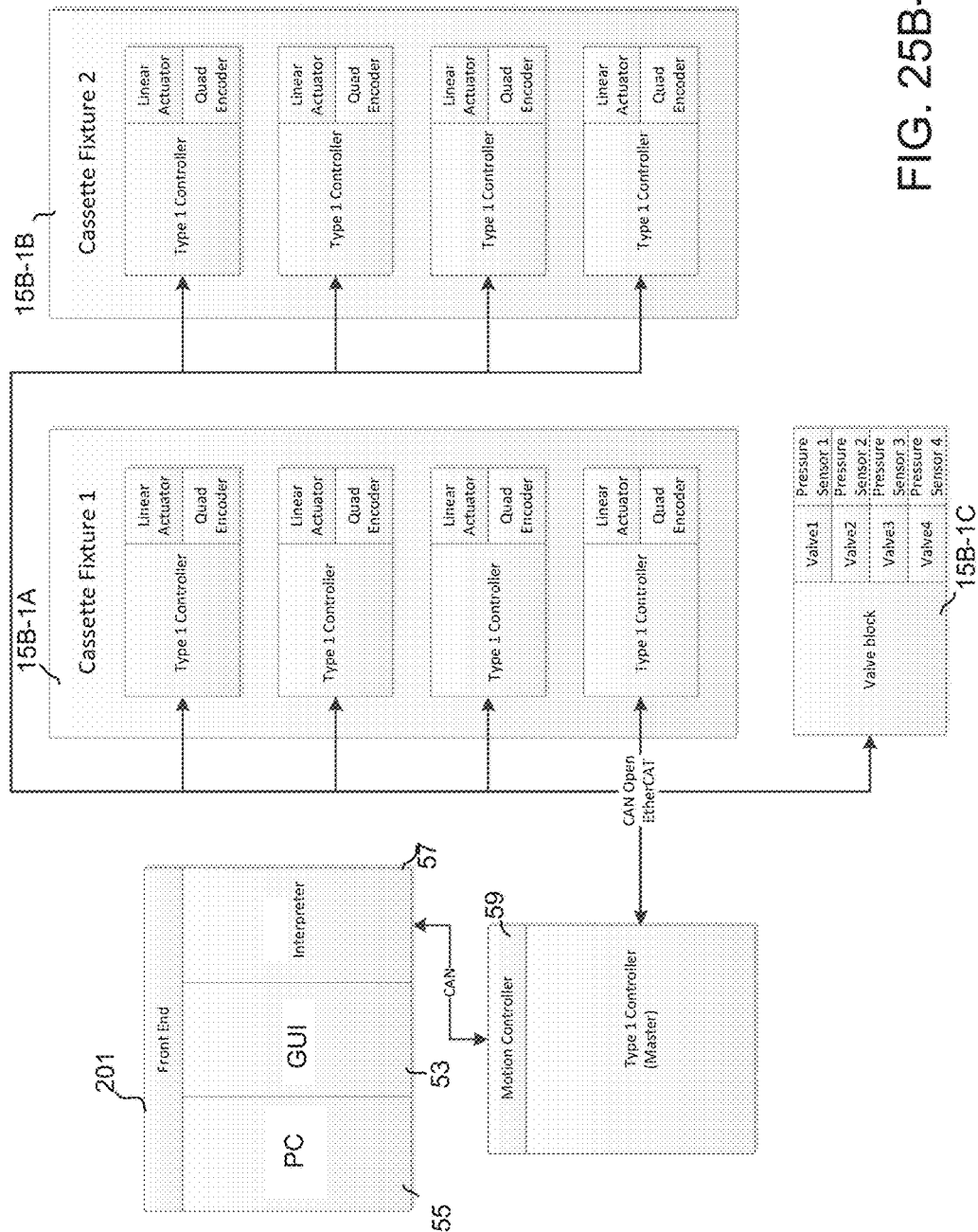

Referring now primarily to FIG. 25B, in some configurations, front end 201 can include, but is not limited to including, computer aided design (CAD) processor 55, command interface 53, and interpreter 57. Command interface 53 can include, for example, but is not limited to including, a graphical user interface. Processor 55 can include, for example, but is not limited to including, a Raspberry Pi LYNX processor that can receive CAD files 65 (FIG. 25) and create Gcode 67 (FIG. 25) based on CAD files 65 (FIG. 25). Interpreter 57 can compute, possibly in near real-time, PF information 69 (FIG. 25) from Gcode 67 (FIG. 25). PF information 69 (FIG. 25) can be provided, possibly in near real-time, to motion controller 59 through, for example, but not limited to, CANbus 203A and/or serial communications 203B and/or wifi 203C.

Figure 25C:
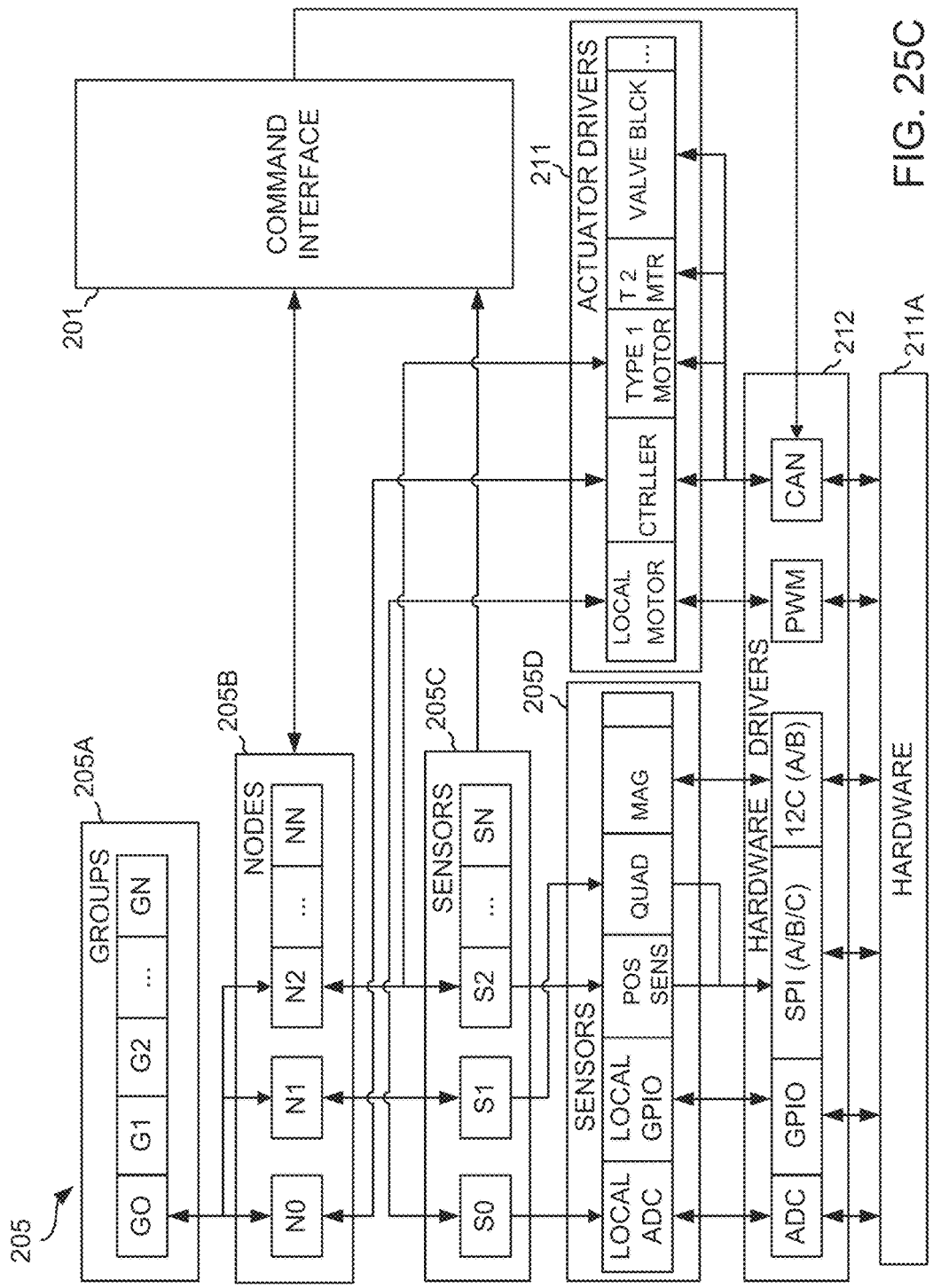
FIG. 25C is a schematic block diagram of details of the motion controller architecture of the present teachings.

Continuing to refer to FIGS. 25B and 25B-1, motion controller 59 can send, across, for example, but not limited to, CANopen/EtherCAT 209, an associated output signal to any of a number of hardware devices 211A (FIG. 25C). If hardware device 211A (FIG. 25C) is, for example, first motor drive 211B, then first motor drive 211B can provide motor control signals through CANopen/EtherCAT 209 to motion controller 59. Motion controller 59 can provide the signals to at least one hardware device 211A (FIG. 25C), such as, for example, but not limited to, at least one brushless DC motor drive 211B/211C, and/or another type 1 controller 59A, and/or integration board 211D, and/or pressure actuator 211E. In some configurations, motion controller 59 can drive at least four motors, for example, but not limited to, 3-phase brushless DC motors 207. In some configurations, closed loop control can provide for position feedback information 207A from an encoder. Motor drives 211B/211C can include, but are not limited to including, motor drives manufactured by MAXON®, ADVANCED MOTION CONTROLS®, and/or ELMO®. Motion controller 59 can receive commands generated by front end 201 and can coordinate hardware devices 211A (FIG. 25C) in real-time. In some configurations, communications between the motor and motion controller 59 can be conducted over serial peripheral interface 207D. In some configurations, motor drive z-axis 211B3 can cause linear actuator 211B5 to move and can cause quad 211B6 to provide feedback to motion controller 59. Motion controller 59 can include, but is not limited to including, any type of motion controller indicated herein by the terminology "type 1 controller" 205.

Referring now to FIG. 25B-2, motion controller 59 can control other motion controllers 59 to perform force actuation simultaneously on various features of a device undergoing force testing, and various devices. In some configurations, force actuation can occur simultaneously on, for example, cassette fixture 1 15B-1A and cassette fixture 2 15B-1B that can be supported in the test by valve block 15B-1C, that can also be controlled by motion controller 59.

Referring now primarily to FIG. 25C, group processor 60A (FIG. 25A) can manage N groups 205A. Each of N groups 205A can include a status that can include, but is not limited to including, the states of active and inactive. Each of the active of N groups 205A can include M node objects 205B. Both N and M can range from one to a value that can be limited by any possible hardware resource limitations. Group processor 60A (FIG. 25A) can include a queue of commands that can include input from command interface 53 (FIG. 25A) and other sources that can include automatic sources. The queue of commands can include a group of commands for each of M node objects 205B of each of N groups 205A. The commands can be, for example, but not limited to, grouped sequentially. In some configurations, node objects 205B can be tightly coordinated, for example, but not limited to, in the case of 3-axis linear motion. When node objects 205B are tightly coordinated, feedback from each of nodes can be used to determine the command to its sibling nodes. In some configurations, node objects 205B can be synchronized. When node objects 205B are synchronized, feedback from a first of node objects 205B may not influence others of node objects 205B. Node processor 60B (FIG. 25A) can manage node objects 205B that can represent, for example, but not limited to, actuator types described herein.

Continuing to refer primarily to FIG. 25C, sensor processor 206 (FIG. 25A), can manage at least one sensor object 205C such as, for example, but not limited to, analog-to-digital converters, general purpose input/output, accelerometer such as for example LMS303 manufactured by STMicroelectronics®, linear position sensor such as, for example, but not limited to, AS5410 manufactured by AMS®, and network input such as, for example, but not limited to, input received through CANbus and EtherCAT protocols. Each sensor object 205C has up to L values. Each can be uniquely configured, for example, but not limited to, for raw value in counts, scaled value, sensor gain, and optional filters. Each sensor object 205C can include a timestamp that can indicate the age of the sensor data. For network input, sensor object 205C can set up a CAN filter to select messages of the appropriate CAN ID and save data associated with the selected message. Update frequency for each sensor object 205C can be configurable, and can be, for example less than the control update frequency. For example, a sensor may sample at 100 Hz while the control loop cycle may be 1 kHz. At least one motion controller 59 (FIG. 25A) can acquire sensor data, update communications information, and periodically process sensor data, update group data, and update node data. Sensor drivers 205D can enable sensor processor 206 (FIG. 1) to communicate with sensor hardware 211A through use of hardware drivers 212. Each of sensor drivers 205D can have knowledge of the communications interface for a specific sensor object. A single instance of each of sensor drivers 205D can be used by many sensor objects 205C.

Continuing to refer to FIG. 25C, sensor data acquisition can include updating communications interfaces such as SPI, I2C, and analog to digital convert (ADC) in parallel with constantly acquired sensor data. Incoming information can be queued and can be interrupt-driven. Available sensor data can be processed regularly, for example, when the system tick time (systick) generates an interrupt request. Actuators drivers 211 can be used by nodes 205B to communicate with at least one hardware type. Each of actuator drivers 211 can include knowledge of a communications interface for a specific type of actuator according to, for example, but not limited to, its make and model. Types of actuator drivers 211 can include, but are not limited to including, hardware driver 212, local and/or network motor drivers, another motion controller 59, and a modular valve apparatus. A single instance of each of actuator drivers 211 can be used by many of nodes 205B. For example, single group 205A can manage four nodes 205B, each of nodes 205B being associated with single sensor object 205C each. Single sensor driver 205D, can include, but is not limited to including, a driver for a quadrature encoder. Single actuator driver 205E, can include, but is not limited including, a driver for a brushless DC motor, for example, but not limited to, a MAXON® network motor driver. Hardware 211A can include a quadrature encoder and the motor/motor drive on the CANbus interface. The quadrature encoder can communicate with sensor driver 205D through hardware drivers 205F and the serial peripheral interface (SPI) communications protocol, for example. The motor can communicate with actuator driver 205E through hardware drivers 205F and the CANbus communications protocol, for example.

Figure 25D:
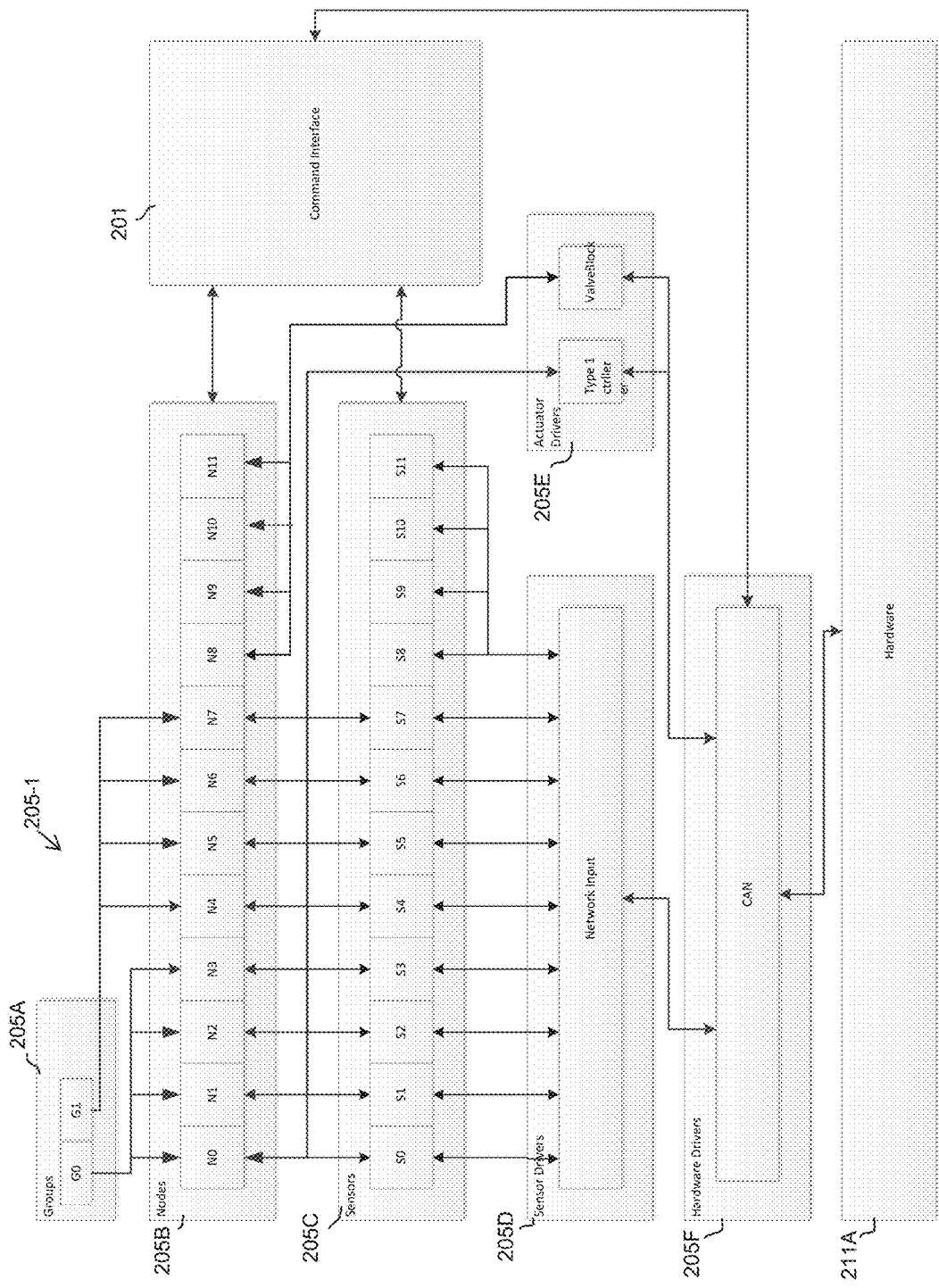
FIG. 25D is a schematic block diagram of a second configuration of the motion controller architecture of the present teachings.

Referring now to FIG. 25D, second configuration motion controller 205-1 can include, but is not limited to including, groups 205A each managing four node objects 205B, each of node objects 205B being associated with a single sensor object 205C. Nodes N8-N11 can operate independently from any of groups 205A. Nodes 205B and sensors 205C can operably communicate with command interface 201, which can communicate with hardware drivers 205F through a CANbus interface. Hardware drivers 205F can operably communicate with hardware 211A through, for example, the CANbus interface. Nodes 205B can also operably communicate with actuator drivers 205E, which scan operably communicate with hardware drivers 205F through the CANbus interface. Second configuration motion controller 205-1 can include sensor drivers 205D, that can operably communicate with sensors 205C through a network, which in turn facilitates operable communications between sensor drivers 205D and hardware drivers 205F through the CANbus interface. Actuator drivers 205E can include, for example, but not limited to, another motion controller driver and a valve block driver.

Figure 25E:
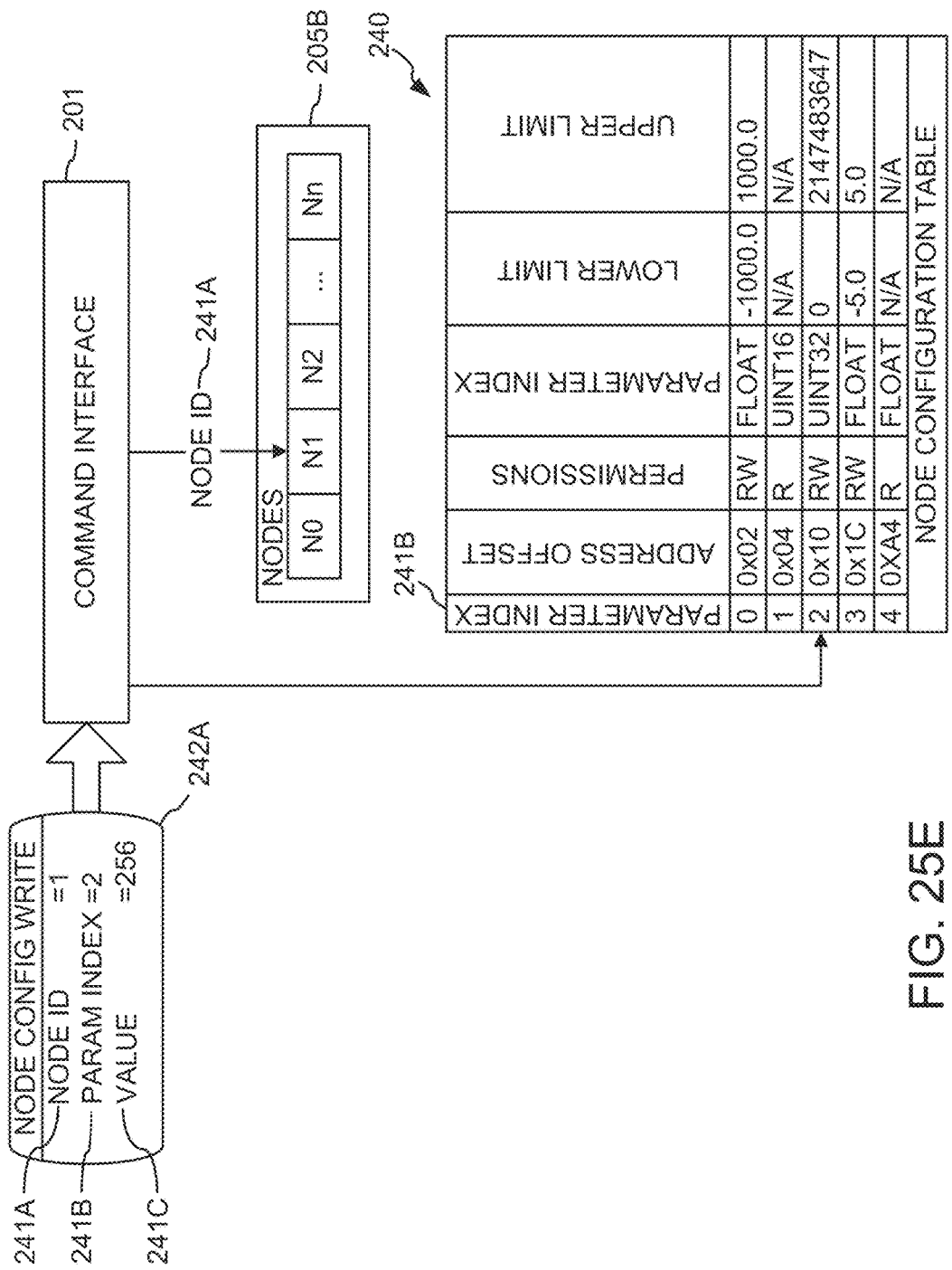
FIG. 25E is a schematic block diagram of the node configuration table of the motion controller architecture of the present teachings.

Referring now to FIG. 25E, node configuration table 240 can enable node objects 205B to be configured, for example, through request 242A to command interface 201. Request 242A can include, but is not limited to including, node object ID 241A, parameter index 241B, and parameter value 241C. Information about parameters associated with node object 205B can include, but is not limited to including, address offset, permissions, parameter type, and value limits.

Figure 25F:
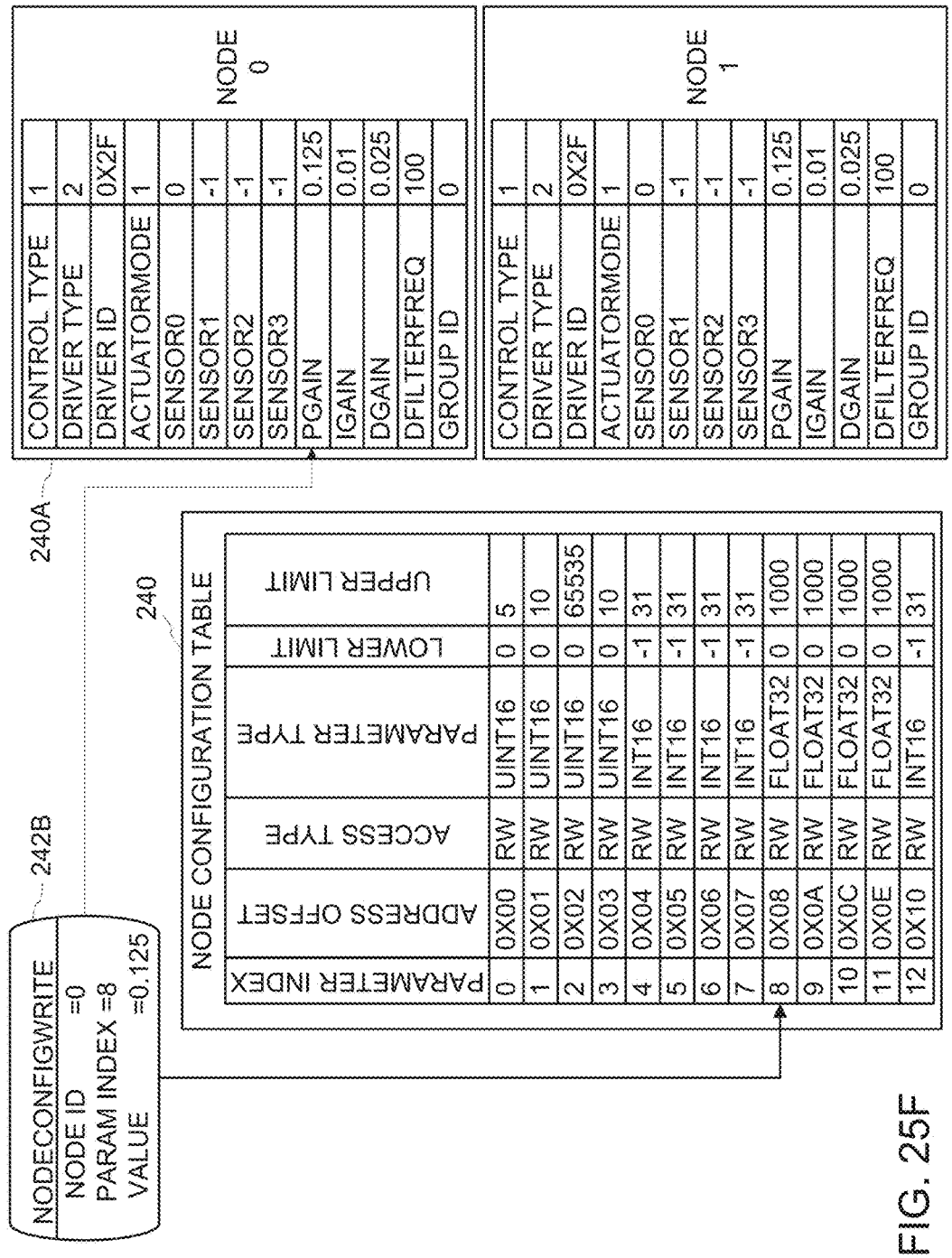
FIGS. 25F and 25G are schematic block diagrams of details of the node configuration table of the motion controller architecture of the present teachings.
Figure 25G:
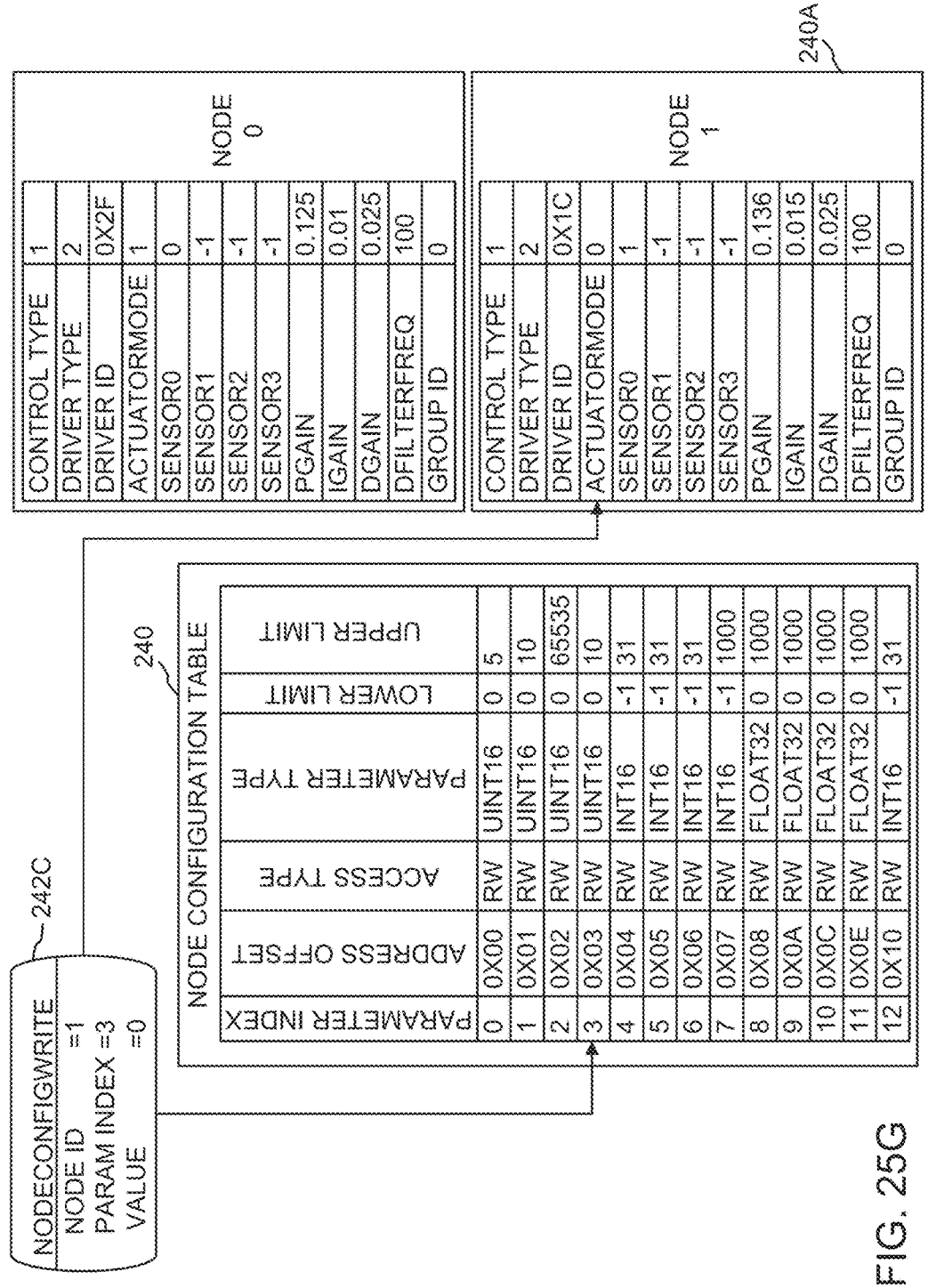

Referring now primarily to FIGS. 25F and 25G, node processor 60B (FIG. 25A) can process requests 242A (FIG. 25E), 242B (FIG. 25F), and 242C (FIG. 25G) and can update a value for a requested parameter in node configuration table 241B, the parameter being described in node parameter table 240A. Exemplary node parameters can include, but are not limited to including, control type, driver type, driver ID, actuator mode, sensors, gains, filter frequency, and group ID. Which node parameters appear in node parameter table 240A can depend upon the type of device that is represented by node parameter table 240A.

Figure 25H:
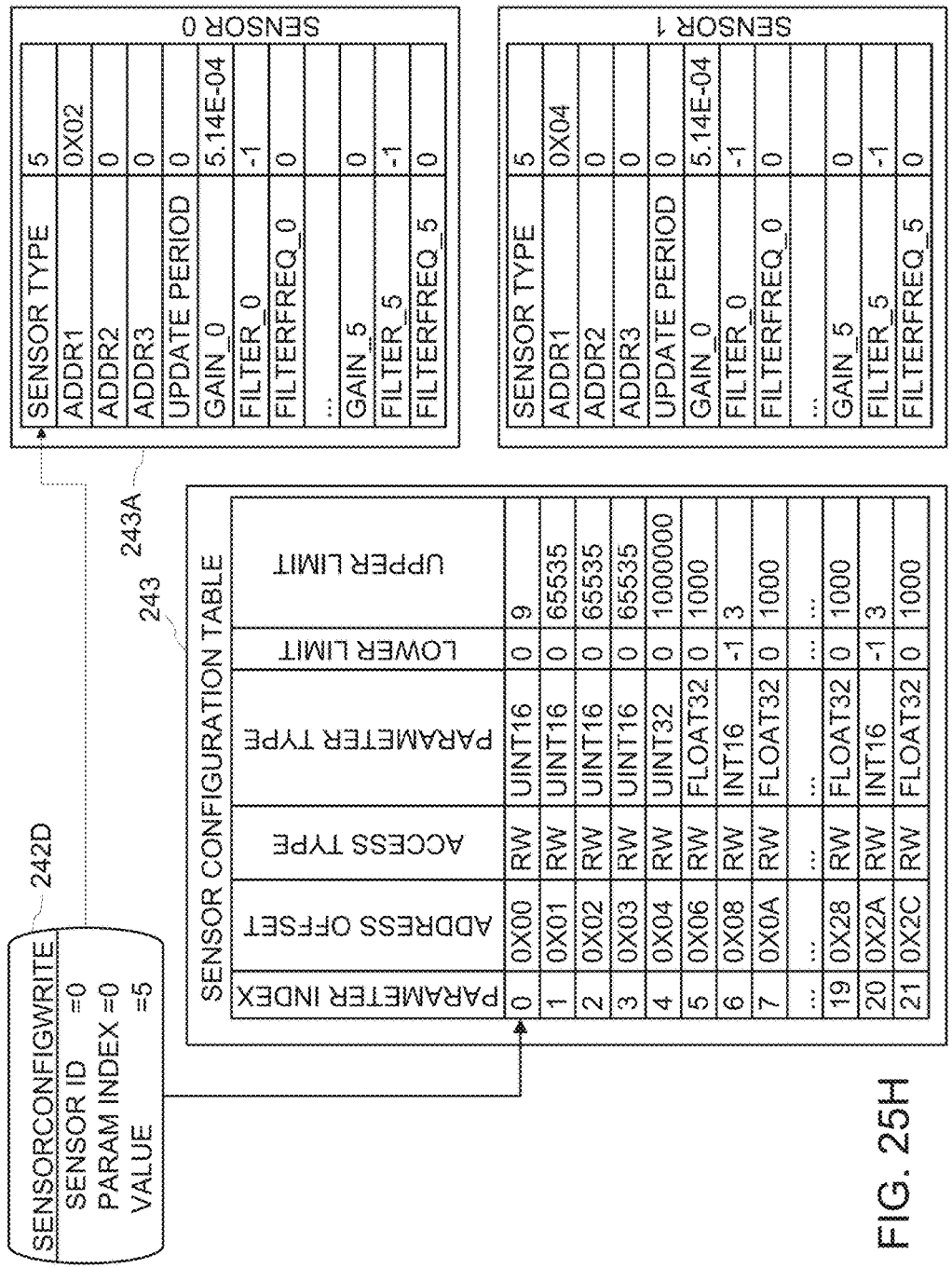
FIGS. 25H and 25I are schematic block diagrams of details of the sensor configuration table of the motion controller architecture of the present teachings.
Figure 25I:
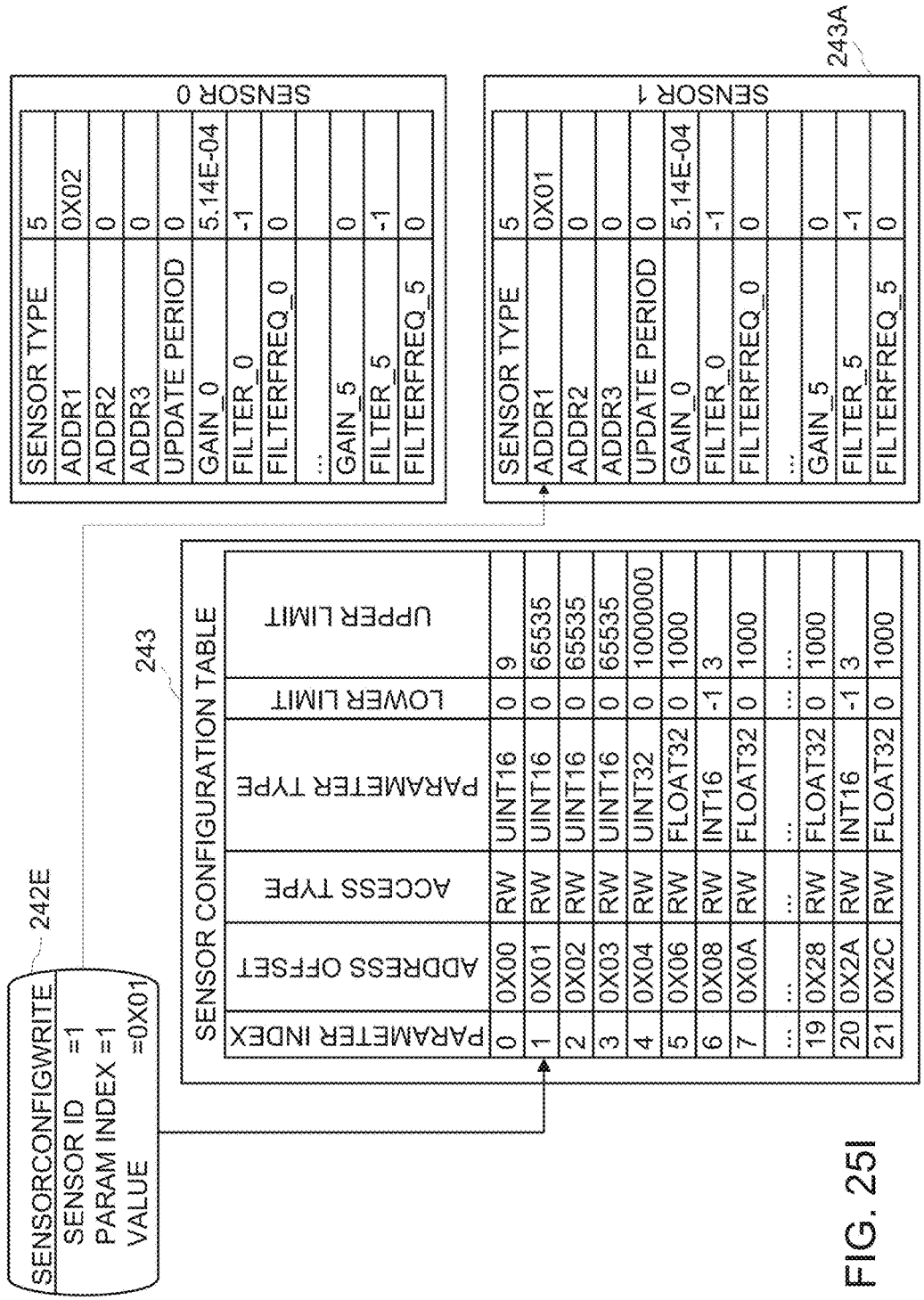

Referring now primarily to FIGS. 25H and 25I, sensor processor 206 (FIG. 25A) can process requests 242D (FIG. 25H) and 242E (FIG. 25I) and can update a value for a requested parameter in sensor configuration table 243, the parameter being described in sensor parameter table 243A. Exemplary sensor parameters can include, but are not limited to including, sensor type, addresses, update period, and the repeated triad gain, filter, and filter frequency. Which sensor parameters appear in sensor parameter table 243A can depend upon the type of sensor that is represented by sensor parameter table 243A. The same configuration scheme can be used to configure any objects, such as, for example, groups, errors, and processors.

Figure 25J:
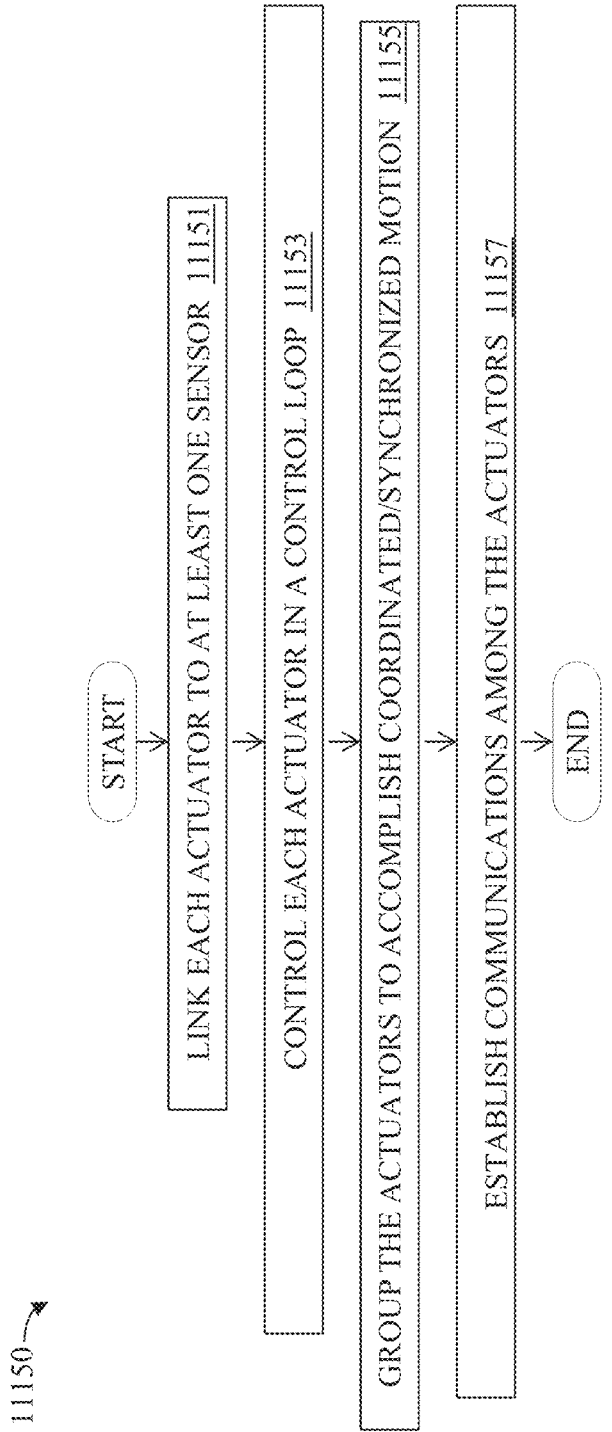
FIG. 25J is a flowchart of the method of use of the motion controller architecture of the present teachings.

Referring now to FIG. 25J, method 11150 for controlling at least one actuator in any configuration can include, but is not limited to including, linking 11151 each of the at least one actuator to at least one sensor, controlling 11153 each of the at least one actuator in a loop, grouping 11155 the at least one actuator to accomplish coordinated/synchronized motion, and establishing 11157 communications among the at least one actuator. Communications can optionally include, but are not limited to including, network communications enabled by standard CAN and EtherCAT protocols. The at least one actuator can optionally enable rotational and/or linear motion, and can include, but is not limited to including, binary valves, pneumatic compressors, modular valves, and heating elements. The at least one sensor can optionally include, but is not limited to including, motor encoder, linear position, pressure sensor, gyroscope, accelerometer, and temperature sensor.

Configurations of the present teachings are directed to computer systems for accomplishing the methods discussed in the description herein, and to computer readable media containing programs for accomplishing these methods. The raw data and results can be stored for future retrieval and processing, printed, displayed, transferred to another computer, and/or transferred elsewhere. Communications links can be wired or wireless, for example, using cellular communication systems, military communications systems, and satellite communications systems. Parts of force actuation system 3100 (FIG. 1), for example, can operate on a computer having a variable number of CPUs. Other alternative computer platforms can be used.

The present configuration is also directed to software for accomplishing the methods discussed herein, and computer readable media storing software for accomplishing these methods. The various modules described herein can be accomplished on the same CPU, or can be accomplished on a different computer. In compliance with the statute, the present configuration has been described in language more or less specific as to structural and methodical features. It is to be understood, however, that the present configuration is not limited to the specific features shown and described, since the means herein disclosed comprise preferred forms of putting the present configuration into effect.

Methods 3150 (FIG. 24) and 11150 (FIG. 25J), can be, in whole or in part, implemented electronically. Signals representing actions taken by elements of force actuation system 3100 (FIG. 1) and other disclosed configurations can travel over at least one live communications network. Control and data information can be electronically executed and stored on at least one computer-readable medium. The systems can be implemented to execute on at least one computer node in at least one live communications network. Common forms of at least one computer-readable medium can include, for example, but not be limited to, a floppy disk, a flexible disk, a hard disk, magnetic tape, or any other magnetic medium, a compact disk read only memory or any other optical medium, punched cards, paper tape, or any other physical medium with patterns of holes, a random access memory, a programmable read only memory, and erasable programmable read only memory (EPROM), a Flash EPROM, or any other memory chip or cartridge, or any other medium from which a computer can read. Further, the at least one computer readable medium can contain graphs in any form, subject to appropriate licenses where necessary, including, but not limited to, Graphic Interchange Format (GIF), Joint Photographic Experts Group (JPEG), Portable Network Graphics (PNG), Scalable Vector Graphics (SVG), and Tagged Image File Format (TIFF).

While the present teachings have been described above in terms of specific configurations, it is to be understood that they are not limited to these disclosed configurations. Many modifications and other configurations will come to mind to those skilled in the art to which this pertains, and which are intended to be and are covered by both this disclosure and the appended claims. It is intended that the scope of the present teachings should be determined by proper interpretation and construction of the appended claims and their legal equivalents, as understood by those of skill in the art relying upon the disclosure in this specification and the attached drawings.

The invention claimed is:

1. A method for testing a device comprising:
providing a pressure actuator aligned with the device, the pressure actuator controlled by a controller;
setting, by the controller, a target first characteristic of the pressure actuator with respect to the device, the pressure actuator having an actual first characteristic with respect to the device;
setting, by the controller, a target second characteristic of the pressure actuator with respect to the device, the pressure actuator having an actual second characteristic with respect to the device;
adjusting, by the controller, the pressure actuator, the adjusting enabling the actual first characteristic to approach the target first characteristic, and the adjusting enabling the actual second characteristic to approach the target second characteristic;
stopping, by the controller, the adjusting when the first of the actual first characteristic substantially equals the target first characteristic, or the actual second characteristic substantially equals the target second characteristic happens;
adjusting, by the controller, the actual first characteristic to maintain the target second characteristic substantially constant; and
testing the device by monitoring, by the controller, the actual first characteristic over time.

2. A system for testing a device comprising:
at least one platform;
at least one holder mount operably coupled with the platform;
at least one device holder operably coupled with the holder mount;
at least one device cover operably coupled with the holder mount;
at least one device cage insertably coupled with the at least one device holder, the device cage housing the device;
at least one pressure actuator assembly substantially aligned with the device cage at pre-selected test points; and
at least one controller setting a target first characteristic of the at least one pressure actuator assembly, the at least one pressure actuator assembly having an actual first characteristic, the at least one controller setting a target second characteristic of the at least one pressure actuator assembly, the at least one pressure actuator assembly having an actual second characteristic, the at least one controller adjusting the at least one pressure actuator assembly, the adjusting enabling the actual first characteristic to approach the target first characteristic, and the actual second characteristic to approach the target second characteristic, and stopping the adjusting when the first of the actual first characteristic substantially equals the target first characteristic, or the actual second characteristic substantially equals the target second characteristic happens, the at least one controller adjusting the actual first characteristic to maintain the target second characteristic substantially constant, and testing the device by monitoring the actual first characteristic over time.

3. The system as in claim 2 wherein the actual first characteristic comprises an actual force and the target first characteristic comprises a target force.

4. The system as in claim 3 wherein the actual second characteristic comprises an actual position and the target first characteristic comprises a target position.

5. The system as in claim 3 wherein the pressure actuator assembly comprises:
an actuator arm coupling electronic and mechanical movement means to move and position a pin actuator, the pin actuator providing the target force on the device.

6. The system as in claim 4 wherein the pressure actuator assembly comprises:
a linear actuator moving the actuator arm towards the target position, the actuator arm forcing the device based at least on commands provided by the at least one controller.

7. The system as in claim 4 wherein the pressure actuator assembly comprises:
an actuator mount coupling the linear actuator with a controller housing enclosing the controller.

8. The system as in claim 5 wherein the actuator mount comprises:
fastening cavities coupling the actuator mount with a platform.

9. The system as in claim 5 wherein the actuator mount comprises:
actuator mounting cavities accommodating at least one alignment peg.

10. The system as in claim 4 wherein the pressure actuator assembly comprises:
a motor interface coupling a motor to the linear actuator, the linear actuator being operably coupled with a slide block, the slide block being operably coupled with the actuator arm, the slide block traveling along the linear actuator, the slide block changing the actual position of the actuator arm, the slide block moving the actuator arm towards the target position.

11. The system as in claim 2 further comprising:
a communications means coupling the pressure actuator assembly with the controller.

12. A method for leak testing a device comprising:
providing a pressure actuator aligned with the device, the pressure actuator controlled by a controller;
setting, by the controller, a target position of a pin with respect to the device, the pin having an actual position;
setting, by the controller, a target force being applied by the pin to the device, the pin having an actual force;
moving, by the pressure actuator as commanded by the controller, the pin towards the target position;
stopping, by the pressure actuator as commanded by the controller, the movement of the pin when either the actual force exerted on the device by the pin substantially equals the target force, or the actual position of the pin substantially equals the target position, whichever happens first; and
testing by the controller, the device by comparing either the actual force or the actual position with at least one benchmark value to determine if the device meets pre-selected criteria at the target position or under the target force.

13. The method as in claim 12 further comprising:
monitoring by the controller, the actual position over time.

14. The method as in claim 12 further comprising:
monitoring by the controller, the actual force over time.

15. The method as in claim 12 further comprising:
modifying, by the pressure actuator as commanded by the controller, the position of the pin to maintain the force of the pin on the device at substantially constant.

16. The method as in claim 12 further comprising:
holding, by the pressure actuator as commanded by the controller, the actual position of the pin substantially constant;
pressurizing, by the pressure actuator as commanded by the controller, the device; and
testing, by the pressure actuator as commanded by the controller, the pressurized device by monitoring the actual force over time.

17. The system as in claim 2 further comprising:
a processor accessing at least one description of the at least one device, the processor creating command information based at least on the at least one description, the processor receiving feedback from the at least one pressure actuator assembly; and
a controller accessing the motion information, the controller creating at least one control command based on the command information, the controller testing the at least one device by controlling the at least one pressure actuator assembly based on the at least one control command.

18. The system as in claim 17 wherein the controller comprises:
a group processor managing at least one group, each of the at least one group being either active or inactive, each of the active of the at least one group including at least one node object, the group processor accessing one of the at least one control commands for each of the at least one node objects;
a node processor updating the at least one node object based on the command information; and
at least one actuator driver relaying the at least one control command between the updated at least one node object and at least one hardware device, the at least one actuator driver communicating the at least one control command to the at least one hardware device through at least one hardware driver.

19. The system as in claim 18 further comprising:
a command interface providing the control information to the at least one node processor and receiving sensor information from at least one sensor processor.

20. The system as in claim 2 further comprising:
simultaneously controlling a plurality of the at least one pressure actuator assemblies.

* * * * *